(12) United States Patent
Hansen et al.

(10) Patent No.: US 8,415,119 B2
(45) Date of Patent: Apr. 9, 2013

(54) METHOD FOR INCREASING EXPRESSION YIELD OF A PROTEIN OF INTEREST

(75) Inventors: Mogens Trier Hansen, Bagsvaerd (DK); Birthe Marie Ravn, Bagsvaerd (DK); Leonardo De Maria, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 12/867,612

(22) PCT Filed: Feb. 20, 2009

(86) PCT No.: PCT/EP2009/052056
§ 371 (c)(1),
(2), (4) Date: Aug. 13, 2010

(87) PCT Pub. No.: WO2009/106488
PCT Pub. Date: Sep. 3, 2009

(65) Prior Publication Data
US 2011/0003333 A1    Jan. 6, 2011

Related U.S. Application Data

(60) Provisional application No. 61/031,206, filed on Feb. 25, 2008.

(30) Foreign Application Priority Data

Feb. 25, 2008  (EP) ..................................... 08151903

(51) Int. Cl.
*C12P 21/02* (2006.01)
*C07K 14/00* (2006.01)
(52) U.S. Cl. .................. 435/69.1; 435/243; 435/254.11; 435/254.2; 536/23.1
(58) Field of Classification Search ........................ None
See application file for complete search history.

(56) References Cited

FOREIGN PATENT DOCUMENTS

| WO | WO 99/60136 | 11/1999 |
|---|---|---|
| WO | WO 01/23592 | 4/2001 |
| WO | WO 01/72783 | 10/2001 |
| WO | WO 2007/123489 | 11/2007 |

OTHER PUBLICATIONS

Giga-Hama (Schizosaccharomyces pombe minimum genome factory, Appl Biochem. Biotechnol. Mar. 2007; 46 (Pt 3):147-55).*
Wang et al. Bioprocessing strategies to improve heterologous protein production in filamentous fungal fermentations Biotechnology Advances 23 (2005) 115-129. (Research review paper).*
Rutkowski and Kaufmann, "A trip to the ER: coping with stress", Trends in Cell Biology vol. 14, No. 1, pp. 20-28 (2004).
Bourges et al., "Regulation of gene expression during the vegetative incompatibility reaction in *Podospora anserine*: characterization of three induced genes", Genetics, vol. 150, No. 2, pp. 633-641 (1998).
Database EMBL Accession No. EY427561, "*Aspergillus oryzae* EST Library *Aspergillus oryzae* cDNA 5', mRNA sequence" (2008).
Database EMBL Accession No. AP007162 "*Aspergillus oryzae* RIB40 genomic DNA, SC102" (2005).
Hideki et al., "ASK1 is essential for endoplasmic reticulum stress-induced neuronal cell death triggered by expanded polyglutamine repeats", Genes and Development, vol. 16, No. 11, pp. 1345-1355 (2002).
MacKenzie et al., "UPR-independent dithiothreitol stress-induced genes in *Aspergillus niger*", Molecular Genetics and Genomics, vol. 274, No. 4, pp. 414-417.
Renata et al., "Endoplasmic reticulum signaling as a determinant of recombinant protein expression", Biotechnology and Bioengineering, vol. 81, No. 1, pp. 56-65 (2003).
Thomas et al., "Genomic analysis of the secretion stress response in the enzyme-producing cell factory *Aspergillus niger*", BMC Genomics Biomed Central, vol. 8, No. 1, p. 158 (2007).
Vongsangnak et al., "Improved annotation through genome-scale metabolic modeling of *Aspergillus oryzae*", BMC Genomics Biomed Central, vol. 9, No. 1, p. 245 (2008).
Database UniProt Accession No. Q3MSC1 "Putative uncharacterized protein (Fragment)" (2005).
Search report issued in corresponding International Application No. PCT/EP2009/052056 dated May 4, 2009.

* cited by examiner

*Primary Examiner* — Kagnew H Gebreyesus
(74) *Attorney, Agent, or Firm* — Michael W. Krenicky

(57) ABSTRACT

The present invention relates to a method of producing a protein of interest comprising: (a) cultivating a mutant cell under conditions conducive for production of the protein wherein the mutant has a reduced or no expression of an endogenous polypeptide shown in SEQ ID NO: 2 compared to a parent host cell grown under the same conditions; and optionally (b) recovering the protein of interest.

15 Claims, 1 Drawing Sheet

```
MetArgLeuSerLeuAsnLeuLeuLeuIleValGlySerAlaAlaValAlaAlaArgAlaAlaAlaLeuValProGlyAlaAlaSerGluGluLeu
ATGAGACTCTCCCTCAACCTCTTACTGATCGTCGGCAGTGCCGCAGTCGCCGCGGGCTGCTCCGGTCCCGGGGCTAGCGAAGAACTT

CysGlyArgLeuGlyValMetTyrTyrAspProAspAsnLeuProGluGlyValGluValHisGluIleArgLysCysAlaGlyHisProMet
TGCGGACGTCTTGGAGTCATGTATTACGATCCTGATAATCTCCCCGAGGGTGTGGAGGTGCATGAGATACGGAAGTGCGCCGGACATCCCATG

GlyArgGluAsnTyrTrpGlyLeuGlyAspTyrLeuProArgTrpPhePro
GGTCGCGAGAACTATTGGGGCTTGGGTGATTATCTGCCGAGGTGGTTCCT
```

SEQUENCE LISTING

```
<160> NUMBER OF SEQ ID NOS: 38

<210> SEQ ID NO 1
<211> LENGTH: 240
<212> TYPE: DNA
<213> ORGANISM: Aspergillus oryzae

<400> SEQUENCE: 1
atgagactct ccctcaacct tctactgatc gtcggatctg ccgcagtcgc ccgggctgct      60
ctggtcccgg tcccgggggc tagcgaagaa ctttgcggac gtcttggagt catgtattac     120
gatcctgata atctccccga gggtgtggag gtgcatgaga tacggaagtg tgccggacat     180
```

```
cccatgggtc gcgagaacta ttggggcttg ggtgattatc tgccgaggtg gtttccttag    240
```

<210> SEQ ID NO 2
<211> LENGTH: 79
<212> TYPE: PRT
<213> ORGANISM: Aspergillu oryzae

<400> SEQUENCE: 2

```
Met Arg Leu Ser Leu Asn Leu Leu Ile Val Gly Ser Ala Ala Val
1               5                   10                  15

Ala Arg Ala Ala Leu Val Pro Val Pro Gly Ala Ser Glu Glu Leu Cys
                20                  25                  30

Gly Arg Leu Gly Val Met Tyr Tyr Asp Pro Asp Asn Leu Pro Glu Gly
                35                  40                  45

Val Glu Val His Glu Ile Arg Lys Cys Ala Gly His Pro Met Gly Arg
    50                  55                      60

Glu Asn Tyr Trp Gly Leu Gly Asp Tyr Leu Pro Arg Trp Phe Pro
65                  70                      75
```

<210> SEQ ID NO 3
<211> LENGTH: 60
<212> TYPE: DNA
<213> ORGANISM: Artificial Sequence
<220> FEATURE:
<223> OTHER INFORMATION: PCR primer

<400> SEQUENCE: 3

```
gacgaattct ctagaagatc tctcgaggag ctcaagcttc tgtacagtga ccggtgactc    60
```

<210> SEQ ID NO 4
<211> LENGTH: 27
<212> TYPE: DNA
<213> ORGANISM: Artificial Sequence
<220> FEATURE:
<223> OTHER INFORMATION: PCR primer

<400> SEQUENCE: 4

```
gacgaattcc gatgaatgtg tgtcctg                                         27
```

<210> SEQ ID NO 5
<211> LENGTH: 30
<212> TYPE: DNA
<213> ORGANISM: Artificial Sequence
<220> FEATURE:
<223> OTHER INFORMATION: PCR primer

<400> SEQUENCE: 5

```
tcttggtacc ctcagcaaag ccatcattgc                                      30
```

<210> SEQ ID NO 6
<211> LENGTH: 32
<212> TYPE: DNA
<213> ORGANISM: Artificial Sequence
<220> FEATURE:
<223> OTHER INFORMATION: PCR primer

<400> SEQUENCE: 6

```
tctctctaga ctccctctgg tttaatactc cg                                   32
```

<210> SEQ ID NO 7
<211> LENGTH: 27
<212> TYPE: DNA
<213> ORGANISM: Artificial Sequence
<220> FEATURE:
<223> OTHER INFORMATION: PCR primer

<400> SEQUENCE: 7
catttggatc caccatgaga ctctccc					27

<210> SEQ ID NO 8
<211> LENGTH: 29
<212> TYPE: DNA
<213> ORGANISM: Artificial Sequence
<220> FEATURE:
<223> OTHER INFORMATION: PCR primer

<400> SEQUENCE: 8
ttctctcgag ctaaggaaac cacctcggc					29

<210> SEQ ID NO 9
<211> LENGTH: 35
<212> TYPE: DNA
<213> ORGANISM: Artificial Sequence
<220> FEATURE:
<223> OTHER INFORMATION: PCR primer

<400> SEQUENCE: 9
tcttggatcc gtcgaccttg gggaagtcat caccg				35

<210> SEQ ID NO 10
<211> LENGTH: 33
<212> TYPE: DNA
<213> ORGANISM: Artificial Sequence
<220> FEATURE:
<223> OTHER INFORMATION: PCR primer

<400> SEQUENCE: 10
gtcattaatc attgaattct cgtcgcgact ctc				33

<210> SEQ ID NO 11
<211> LENGTH: 45
<212> TYPE: DNA
<213> ORGANISM: Artificial Sequence
<220> FEATURE:
<223> OTHER INFORMATION: PCR primer

<400> SEQUENCE: 11
gtcgcgacga gaattcaatg attaatgacc ttttcctaaa tatac		45

<210> SEQ ID NO 12
<211> LENGTH: 40
<212> TYPE: DNA
<213> ORGANISM: Artificial Sequence
<220> FEATURE:
<223> OTHER INFORMATION: PCR primer

<400> SEQUENCE: 12
tcttctcgag cctaggtatc ccaaagtcaa gtacgtcagg			40

<210> SEQ ID NO 13
<211> LENGTH: 37
<212> TYPE: DNA
<213> ORGANISM: Artificial Sequence
<220> FEATURE:
<223> OTHER INFORMATION: PCR primer

<400> SEQUENCE: 13
tcttctcgag cctaggctct ccctcaacct tctactg			37

<210> SEQ ID NO 14
<211> LENGTH: 6022

```
<212> TYPE: DNA
<213> ORGANISM: Artificial Sequence
<220> FEATURE:
<223> OTHER INFORMATION: complete DNA sequence of plasmid pJaL504
<220> FEATURE:
<221> NAME/KEY: misc_feature
<222> LOCATION: (2545)..(2545)
<223> OTHER INFORMATION: n is a, c, g, or t
<220> FEATURE:
<221> NAME/KEY: misc_feature
<222> LOCATION: (2753)..(2753)
<223> OTHER INFORMATION: n is a, c, g, or t
<220> FEATURE:
<221> NAME/KEY: misc_feature
<222> LOCATION: (2844)..(2844)
<223> OTHER INFORMATION: n is a, c, g, or t

<400> SEQUENCE: 14
```

| | | |
|---|---|---|
| gaatacacgg aattcctcga gtaccattta attctatttg tgtttgatcg agacctaata | 60 |
| cagcccctac aacgaccatc aaagtcgtat agctaccagt gaggaagtgg actcaaatcg | 120 |
| acttcagcaa catctcctgg ataaacttta agcctaaact atacagaata agataggtgg | 180 |
| agagcttata ccgagctccc aaatctgtcc agatcatggt tgaccggtgc ctggatcttc | 240 |
| ctatagaatc atccttattc gttgacctag ctgattctgg agtgacccag agggtcatga | 300 |
| cttgagccta aaatccgccg cctccaccat ttgtagaaaa atgtgacgaa ctcgtgagct | 360 |
| ctgtacagtg accggtgact cttttctggca tgcggagaga cggacggacg cagagagaag | 420 |
| ggctgagtaa taagccactg ccagacagc tctggcggct ctgaggtgca gtggatgatt | 480 |
| attaatccgg gaccggccgc ccctccgccc gaagtggaa aggctggtgt gcccctcgtt | 540 |
| gaccaagaat ctattgcatc atcggagaat atggagcttc atcgaatcac cggcagtaag | 600 |
| cgaaggagaa tgtgaagcca ggggtgtata gccgtcggcg aaatagcatg ccattaacct | 660 |
| aggtacagaa gtccaattgc ttccgatctg gtaaagatt cacgagatag taccttctcc | 720 |
| gaagtaggta gagcgagtac ccggcgcgta agctccctaa ttggcccatc cggcatctgt | 780 |
| agggcgtcca aatatcgtgc ctctcctgct ttgcccggtg tatgaaaccg gaaaggccgc | 840 |
| tcaggagctg gccagcggcg cagaccggga acacaagctg gcagtcgacc catccggtgc | 900 |
| tctgcactcg acctgctgag gtccctcagt ccctggtagg cagcttttgcc ccgtctgtcc | 960 |
| gcccggtgtg tcggcggggt tgacaaggtc gttgcgtcag tccaacatttt gttgccatat | 1020 |
| tttcctgctc tccccaccag ctgtagatct tggtggcgtg aaactcccgc acctcttcgg | 1080 |
| ccagcgcctt gtagaagcgc gtatggcttc gtaccccggc catcaacacg cgtctgcgtt | 1140 |
| cgaccaggct gcgcgttctc gcggccatag caaccgacgt acggcgttgc gccctcgccg | 1200 |
| gcagcaagaa gccacggaag tccgcccgga gcagaaaatg cccacgctac tgcgggttta | 1260 |
| tatagacggt ccccacggga tggggaaaac caccaccacg caactgctgg tggccctggg | 1320 |
| ttcgcgcgac gatatcgtct acgtacccga gccgatgact tactggcggg tgctgggggc | 1380 |
| ttccgagaca atcgcgaaca tctacaccac acaacaccgc ctcgaccagg gtgagatatc | 1440 |
| ggccggggac gcggcggtgg taatgacaag cgcccagata acaatgggca tgccttatgc | 1500 |
| cgtgaccgac gccgttctgg ctcctcatat cggggggggag gctgggagct cacatgcccc | 1560 |
| gcccccggcc ctcaccctca tcttcgaccg ccatcccatc gccgcctcc tgtgctaccc | 1620 |
| ggccgcgcgg taccttatgg gcagcatgac ccccaggcc gtgctggcgt tcgtggccct | 1680 |
| catcccgccg accttgcccg gcaccaacat cgtgcttggg gcccttccgg aggacagaca | 1740 |
| catcgaccgc ctgccaaaac gccagcgccc cggcgagcgg ctggacctgg ctatgctggc | 1800 |
| tgcgattcgc cgcgtttacg ggctacttgc caatacggtg cggtatctgc agtgcggcgg | 1860 |

```
gtcgtggcgg gaggactggg gacagctttc ggggacggcc gtgccgcccc agggtgccga   1920
gccccagagc aacgcgggcc cacgacccca tatcggggac acgttattta ccctgtttcg   1980
gggccccgag ttgctggccc ccaacggcga cctgtataac gtgtttgcct ggccttgga    2040 cgtcttggcc aaacgcctcc gttccatgca cgtctttatc ctggattacg accaatcgcc   2100
cgccggctgc cggacgccc tgctgcaact tacctccggg atggtccaga cccacgtcac    2160 caccccggc tccataccga cgatatgcga cctggcgcgc acgtttgccc gggagatggg    2220
ggaggctaac tgaaacacgg aaggagacaa taccggaagg aacccgcgct atccggatcg   2280
atccacttaa cgttactgaa atcatcaaac agcttgacga atctggatat aagatcgttg   2340
gtgtcgatgt cagctccgga gttgagacaa atggtgttca ggatctcgat aagatacgtt   2400
catttgtcca agcagcaaag agtgccttct agtgatttaa tagctccatg tcaacaagaa   2460
taaaacgcgt tttcgggttt acctcttcca gatacagctc atctgcaatg cattaatgca   2520
ttgactgcaa cctagtaacg ccttncaggc tccggcgaag agaagaatag cttagcagag   2580
ctattttcat tttcgggaga cgagatcaag cagatcaacg gtcgtcaaga gacctacgag   2640
actgaggaat ccgctcttgg ctccacgcga ctatatattt gtctctaatt gtactttgac   2700
atgctcctct tctttactct gatagcttga ctatgaaaat tccgtcacca gcnctgggt    2760 tcgcaaagat aattgcatgt ttcttccttg aactctcaag cctacaggac acacattcat   2820
cgtaggtata aacctcgaaa tcanttccta ctaagatggt atacaatagt aaccatgcat   2880
ggttgcctag tgaatgctcc gtaacaccca atacgccggc cgaaacttttt ttacaactct   2940 cctatgagtc gtttacccag aatgcacagg tacacttgtt tagaggtaat ccttctttct   3000
agaagtcctc gtgtactgtg taagcgccca ctccacatct ccactcgacc tgcaggcatg   3060
caagcttggc gtaatcatgg tcatagctgt ttcctgtgtg aaattgttat ccgctcacaa   3120
ttccacacaa catacgagcc ggaagcataa agtgtaaagc ctggggtgcc taatgagtga   3180
gctaactcac attaattgcg ttgcgctcac tgcccgcttt ccagtcggga aacctgtcgt   3240
gccagagcgg ccgctctgca ttaatgaatc ggccaacgcg cggggagagg cggtttgcgt   3300
attgggcgct cttccgcttc ctcgctcact gactcgctgc gctcggtcgt tcggctgcgg   3360
cgagcggtat cagctcactc aaaggcggta atacggttat ccacagaatc agggggataac   3420 gcaggaaaga acatgtgagc aaaaggccag caaaaggcca ggaaccgtaa aaaggccgcg   3480
ttgctggcgt ttttccatag gctccgcccc cctgacgagc atcacaaaaa tcgacgctca   3540
agtcagaggt ggcgaaaccc gacaggacta taaagatacc aggcgtttcc ccctggaagc   3600
tccctcgtgc gctctcctgt tccgaccctg ccgcttaccg gatacctgtc cgcctttctc   3660
ccttcgggaa gcgtggcgct ttctcatagc tcacgctgta ggtatctcag ttcggtgtag   3720
gtcgttcgct ccaagctggg ctgtgtgcac gaaccccccg ttcagcccga ccgctgcgcc   3780
ttatccggta actatcgtct tgagtccaac ccggtaagac acgacttatc gccactggca   3840
gcagccactg gtaacaggat tagcagagcg aggtatgtag gcggtgctac agagttcttg   3900
aagtggtggc ctaactacgg ctacactaga aggacagtat ttggtatctg cgctctgctg   3960
aagccagtta ccttcggaaa aagagttggt agctcttgat ccggcaaaca aaccaccgct   4020
ggtagcggtg gttttttttgt ttgcaagcag cagattacgc gcagaaaaaa aggatctcaa   4080
gaagatcctt tgatcttttc tacggggtct gacgctcagt ggaacgaaaa ctcacgttaa   4140
gggattttgg tcatgagatt atcaaaaagg atcttcacct agatcctttt aaattaaaaa   4200
tgaagtttta aatcaatcta agtatatat gagtaaactt ggtctgacag ttaccaatgc   4260
```

```
ttaatcagtg aggcacctat ctcagcgatc tgtctatttc gttcatccat agttgcctga   4320
ctccccgtcg tgtagataac tacgatacgg gagggcttac catctggccc cagtgctgca   4380
atgataccgc gagacccacg ctcaccggct ccagatttat cagcaataaa ccagccagcc   4440
ggaagggccg agcgcagaag tggtcctgca actttatccg cctccatcca gtctattaat   4500
tgttgccggg aagctagagt aagtagttcg ccagttaata gtttgcgcaa cgttgttgcc   4560
attgctacag gcatcgtggt gtcacgctcg tcgtttggta tggcttcatt cagctccggt   4620
tcccaacgat caaggcgagt tacatgatcc cccatgttgt gcaaaaaagc ggttagctcc   4680
ttcggtcctc cgatcgttgt cagaagtaag ttggccgcag tgttatcact catggttatg   4740
gcagcactgc ataattctct tactgtcatg ccatccgtaa gatgcttttc tgtgactggt   4800
gagtactcaa ccaagtcatt ctgagaatag tgtatgcggc gaccgagttg ctcttgcccg   4860
gcgtcaatac gggataatac cgcgccacat agcagaactt taaaagtgct catcattgga   4920
aaacgttctt cggggcgaaa actctcaagg atcttaccgc tgttgagatc cagttcgatg   4980
taacccactc gtgcacccaa ctgatcttca gcatctttta ctttcaccag cgtttctggg   5040
tgagcaaaaa caggaaggca aaatgccgca aaaagggaa taagggcgac acggaaatgt   5100
tgaatactca tactcttcct ttttcaatat tattgaagca tttatcaggg ttattgtctc   5160
atgagcggat acatatttga atgtatttag aaaaataaac aaataggggt tccgcgcaca   5220
tttccccgaa aagtgccacc tgacgtctaa gaaaccatta ttatcatgac attaacctat   5280 aaaaatagg gtatcacgag gccctttcgt ctcgcgcgtt tcggtgatga cggtgaaaac   5340
ctctgacaca tgcagctccc ggagacggtc acagcttgtc tgtaagcgga tgccgggagc   5400
agacaagccc gtcagggcgc gtcagcgggt gttggcgggt gtcggggctg gcttaactat   5460
gcggcatcag agcagattgt actgagagtg caccatatcg acgctctccc ttatgcgact   5520
cctgcattag gaagcagccc agtagtaggt tgaggccgtt gagcaccgcc gccgcaagga   5580
atggtgcatg caaggagatg gcgcccaaca gtccccggc cacggggcct gccaccatac   5640
ccacgccgaa acaagcgctc atgagcccga agtggcgagc ccgatcttcc ccatcggtga   5700
tgtcggcgat ataggcgcca gcaaccgcac ctgtggcgcc ggtgatgccg gccacgatgc   5760
gtccggcgta gaggatctgg ctagcgatga ccctgctgat tggttcgctg accatttccg   5820
gggtgcggaa cggcgttacc agaaactcag aaggttcgtc caaccaaacc gactctgacg   5880
gcagtttacg agagagatga tagggtctgc ttcagtaagc cagatgctac acaattaggc   5940
ttgtacatat tgtcgttaga acgcggctac aattaataca taaccttatg tatcatacac   6000
atacgattta ggtgacacta ta                                            6022
```

<210> SEQ ID NO 15
<211> LENGTH: 6471
<212> TYPE: DNA
<213> ORGANISM: Artificial Sequence
<220> FEATURE:
<223> OTHER INFORMATION: complete DNA sequence of plasmid pJaL575
<220> FEATURE:
<221> NAME/KEY: misc_feature
<222> LOCATION: (2742)..(2742)
<223> OTHER INFORMATION: n is a, c, g, or t

<400> SEQUENCE: 15

```
agcgcccaat acgcaaaccg cctctccccg cgcgttggcc gattcattaa tgcagctggc     60
acgacaggtt tcccgactgg aaagcgggca gtgagcgcaa cgcaattaat gtgagttagc    120
tcactcatta ggcaccccag gctttacact ttatgcttcc ggctcgtatg ttgtgtggaa    180
```

```
ttgtgagcgg ataacaattt cacacaggaa acagctatga ccatgattac gccaagctca    240
gaattaaccc tcactaaagg gactagtcct gcaggtttaa acgaattcgc ccttgacgaa    300
ttctctagaa gatctctcga ggagctcaag cttgagctct gtacagtgac cggtgactct    360
ttctggcatg cggagagacg gacggacgca gagagaaggg ctgagtaata acggccactg    420
cgccagacag ctctggcggc tctgaggtgc agtggatgat tattaatccg ggaccggccg    480
cccctccgcc ccgaagtgga aaggctggtg tgcccctcgt tgaccaagaa tctattgcat    540
catcggagaa tatggagctt catcgaatca ccggcagtaa gcgaaggaga atgtgaagcc    600
aggggtgtat agccgtcggc gaaatagcat gccattaacc taggtacaga agtccaattg    660
cttccgatct ggtaaaagat tcacgagata gtaccttctc cgaagtaggt agagcgagta    720
cccggcgcgt aagctcccta attggcccat ccggcatctg tagggcgtcc aaatatcgtg    780
cctctcctgc tttgcccggt gtatgaaacc ggaaaggccg ctcaggagct ggccagcggc    840
gcagaccggg aacacaagct ggcagtcgac ccatccggtg tctgcactc gacctgctga    900 ggtccctcag tccctggtag gcagctttgc cccgtctgtc cgcccggtgt gtcggcgggg    960
ttgacaaggt cgttgcgtca gtccaacatt tgttgccata ttttcctgct ctccccacca   1020
gctgtagatc gatcttggtg gcgtgaaact cccgcacctc ttcggccagc gccttgtaga   1080
agcgcgtatg gcttcgtacc ccggccatca acacgcgtct gcgttcgacc aggctgcgcg   1140
ttctcgcggc catagcaacc gacgtacggc gttgcgccct cgccggcagc aagaagccac   1200
ggaagtccgc ccggagcaga aaatgccac gctactgcgg gtttatatag acggtcccca   1260
cgggatgggg aaaaccacca ccacgcaact gctggtggcc ctgggttcgc gcgacgatat   1320
cgtctacgta cccgagccga tgacttactg gcgggtgctg ggggcttccg agacaatcgc   1380
gaacatctac accacacaac accgcctcga ccagggtgag atatcggccg gggacgcggc   1440
ggtggtaatg acaagcgccc agataacaat gggcatgcct tatgccgtga ccgacgcgt   1500 tctggctcct catatcgggg gggaggctgg gagctcacat gccccgcccc cggccctcac   1560
cctcatcttc gaccgccatc ccatcgccgc cctcctgtgc tacccggccg cgcggtacct   1620
tatgggcagc atgacccccc aggccgtgct ggcgttcgtg gccctcatcc cgccgacctt   1680
gcccggcacc aacatcgtgc ttggggcccct tccggaggac agacacatcg accgcctggc   1740
caaacgccag cgccccggcg agcggctgga cctggctatg ctggctgcga ttcgccgcgt   1800
ttacgggcta cttgccaata cggtgcggta tctgcagtgc ggcgggtcgt ggcgggagga   1860
ctggggacag cttttcgggga cggccgtgcc gccccagggt gccgagcccc agagcaacgc   1920
gggcccacga ccccatatcg gggacacgtt atttaccctg tttcggggcc ccgagttgct   1980
ggcccccaac ggcgacctgt ataacgtgtt tgcctgggcc ttggacgtct ggccaaacg   2040 cctccgttcc atgcacgtct ttatcctgga ttacgaccaa tcgcccgccg gctgccggga   2100
cgccctgctg caacttacct ccgggatggt ccagacccac gtcaccaccc ccggctccat   2160
accgacgata tgcgacctgg cgcgcacgtt gccccgggag atgggggagg ctaactgaaa   2220 cacgggaagga gacaatacccg gaaggaaccc gcgctatccg gatcgatcca cttaacgtta   2280
ctgaaatcat caaacagctt gacgaatctg gatataagat cgttggtgtc gatgtcagct   2340
ccggagttga gacaaatggt gttcaggatc tcgataagat acgttcattt gtccaagcag   2400
caaagagtgc cttctagtga tttaatagct ccatgtcaac aagaataaaa cgcgtttcgg   2460
gtttacctct tccagataca gctcatctgc aatgcattaa tgcattggac ctcgcaaccc   2520
tagtacgccc ttcaggctcc ggcgaagcag aagaatagct tagcagagtc tatttttcatt   2580
```

```
ttcgggagac gagatcaagc agatcaacgg tcgtcaagag acctacgaga ctgaggaatc   2640
cgctcttggc tccacgcgac tatatatttg tctctaattg tactttgaca tgctcctctt   2700
ctttactctg atagcttgac tatgaaaatt ccgtcaccag cncctgggtt cgcaaagata   2760
attgcactgt ttcttccttg aactctcaag cctacaggag aattcgtcaa gggcgaattc   2820
gcggccgcta aattcaattc gccctatagt gagtcgtatt acaattcact ggccgtcgtt   2880
ttacaacgtc gtgactggga aaaccctggc gttacccaac ttaatcgcct tgcagcacat   2940
ccccctttcg ccagctggcg taatagcgaa gaggcccgca ccgatcgccc ttcccaacag   3000
ttgcgcagcc tatacgtacg gcagtttaag gtttacacct ataaaagaga gagccgttat   3060
cgtctgtttg tggatgtaca gagtgatatt attgacacgc cggggcgacg gatggtgatc   3120
cccctggcca gtgcacgtct gctgtcagat aaagtctccc gtgaacttta cccggtggtg   3180
catatcgggg atgaaagctg gcgcatgatg accaccgata tggccagtgt gccggtctcc   3240
gttatcgggg aagaagtggc tgatctcagc caccgcgaaa atgacatcaa aaacgccatt   3300
aacctgatgt tctggggaat ataaatgtca ggcatgagat tatcaaaaag gatcttcacc   3360
tagatccttt tcacgtagaa agccagtccg cagaaacggt gctgaccccg gatgaatgtc   3420
agctactggg ctatctggac aagggaaaac gcaagcgcaa agagaaagca ggtagcttgc   3480
agtgggctta catggcgata gctagactgg gcggttttat ggacagcaag cgaaccggaa   3540
ttgccagctg gggcgccctc tggtaaggtt gggaagccct gcaaagtaaa ctggatggct   3600
ttctcgccgc caaggatctg atggcgcagg ggatcaagct ctgatcaaga dacaggatga   3660
ggatcgtttc gcatgattga acaagatgga ttgcacgcag ttctccggc cgcttgggtg   3720 gagaggctat tcggctatga ctgggcacaa cagacaatcg gctgctctga tgccgccgtg   3780
ttccggctgt cagcgcaggg gcgcccggtt ctttttgtca agaccgacct gtccggtgcc   3840
ctgaatgaac tgcaagacga ggcagcgcgg ctatcgtggc tggccacgac gggcgttcct   3900
tgcgcagctg tgctcgacgt tgtcactgaa gcgggaaggg actggctgct attgggcgaa   3960
gtgccggggc aggatctcct gtcatctcac cttgctcctg ccgagaaagt atccatcatg   4020
gctgatgcaa tgcggcggct gcatacgctt gatccggcta cctgcccatt cgaccaccaa   4080
gcgaaacatc gcatcgagcg agcacgtact cggatggaag ccggtcttgt cgatcaggat   4140
gatctggacg aagagcatca ggggctcgcg ccagccgaac tgttcgccag gctcaaggcg   4200
agcatgcccg acggcgagga tctcgtcgtg acccatggcg atgcctgctt gccgaatatc   4260
atggtggaaa atggccgctt ttctggattc atcgactgtg gccggctggg tgtggcggac   4320
cgctatcagg acatagcgtt ggctacccgt gatattgctg aagagcttgg cggcgaatgg   4380
gctgaccgct tcctcgtgct ttacggtatc gccgctcccg attcgcagcg catcgccttc   4440
tatcgccttc ttgacgagtt cttctgaatt attaacgctt acaatttcct gatgcggtat   4500
tttctcctta cgcatctgtg cggtatttca caccgcatac aggtggcact tttcggggaa   4560
atgtgcgcgg aacccctatt tgtttatttt tctaaataca ttcaaatatg tatccgctca   4620
tgagacaata accctgataa atgcttcaat aatattgaaa aaggaagagt atgagtattc   4680
aacatttccg tgtcgccctt attcccttt ttgcggcatt ttgccttcct gtttttgctc   4740
acccagaaac gctggtgaaa gtaaaagatg ctgaagatca gttgggtgca cgagtgggtt   4800
acatcgaact ggatctcaac agcggtaaga tccttgagag ttttcgcccc gaagaacgtt   4860
ttccaatgat gagcactttt aaagttctgc tatgtggcgc ggtattatcc cgtattgacg   4920
ccgggcaaga gcaactcggt cgccgcatac actattctca gaatgacttg gttgagtact   4980
```

```
caccagtcac agaaaagcat cttacggatg gcatgacagt aagagaatta tgcagtgctg    5040
ccataaccat gagtgataac actgcggcca acttacttct gacaacgatc ggaggaccga    5100
aggagctaac cgcttttttg cacaacatgg gggatcatgt aactcgcctt gatcgttggg    5160
aaccggagct gaatgaagcc ataccaaacg acgagcgtga ccaccacgatg cctgtagcaa    5220 tggcaacaac gttgcgcaaa ctattaactg gcgaactact tactctagct tcccggcaac    5280
aattaataga ctggatggag gcggataaag ttgcaggacc acttctgcgc tcggcccttc    5340
cggctggctg gtttattgct gataaatctg gagccggtga gcgtgggtct cgcggtatca    5400
ttgcagcact ggggccagat ggtaagccct cccgtatcgt agttatctac acgacgggga    5460
gtcaggcaac tatggatgaa cgaaatagac agatcgctga gataggtgcc tcactgatta    5520
agcattggta actgtcagac caagtttact catatatact ttagattgat ttaaaacttc    5580 attttaatt taaaaggatc taggtgaaga tcctttttga taatctcatg accaaaatcc    5640
cttaacgtga gttttcgttc cactgagcgt cagaccccgt agaaaagatc aaaggatctt    5700
cttgagatcc tttttttctg cgcgtaatct gctgcttgca acaaaaaaa ccaccgctac    5760 cagcggtggt ttgtttgccg gatcaagagc taccaactct ttttccgaag gtaactggct    5820
tcagcagagc gcagatacca atactgtcc ttctagtgta gccgtagtta ggccaccact    5880
tcaagaactc tgtagcaccg cctacatacc tcgctctgct aatcctgtta ccagtggctg    5940
ctgccagtgg cgataagtcg tgtcttaccg ggttggactc aagacgatag ttaccggata    6000
aggcgcagcg gtcgggctga cgggggggtt cgtgcacaca gcccagcttg gagcgaacga    6060
cctacaccga actgagatac ctacagcgtg agctatgaga aagcgccacg cttcccgaag    6120
ggagaaaggc ggacaggtat ccggtaagcg gcagggtcgg aacaggagag cgcacgaggg    6180
agcttccagg gggaaacgcc tggtatcttt atagtcctgt cgggtttcgc cacctctgac    6240
ttgagcgtcg atttttgtga tgctcgtcag ggggggcggag cctatggaaa aacgccagca    6300
acgcggcctt tttacggttc ctgggctttt gctggccttt tgctcacatg ttctttcctg    6360
cgttatcccc tgattctgtg gataaccgta ttaccgcctt tgagtgagct gataccgctc    6420
gccgcagccg aacgaccgag cgcagcgagt cagtgagcga ggaagcggaa g            6471

<210> SEQ ID NO 16
<211> LENGTH: 6169
<212> TYPE: DNA
<213> ORGANISM: Artificial Sequence
<220> FEATURE:
<223> OTHER INFORMATION: complete DNA sequence of plasmid pJaL731

<400> SEQUENCE: 16
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccaggccaag ctttcgcgag ctcgagatct     420
gtataaagaa ggtatgagtt ataactgctc cactcctatc cttatcaggt tgcttgcacc     480
ggctgtcatg cttgtcccct tgagccgtta cattctcaca ctctgaaagg ttttttaaca     540
tcgccggagc tcttctatgt tcgaaatcat ggcccagtcc ctcatatcaa ggatgaagat     600
```

```
atccctcact gggaaattag catcgaaggg ttagtatagt gctaggttct ctgccaaaca      660
tccgttaacc aaagtataga ctggtagaga agcctttggt actaaacttc cgacaagtgt      720
tgcagcagta cgaccaaata acagcgccta tcaccctcgt atgtgctggc aatcgacgca      780
aagagcaaaa cattgtacgt aaaacgaaag gttttcctg gggatcggcg ggactatcga        840
ctgccctctt cactggccca ttgctggcgg atattctccg cagtgcgaaa cccctgcgta      900
aagcgaaata cgtctgtatg gaggagcgg ataagctggt atgctgtacc tctatcttat        960
gatgataatt gctaagttcg ccgcagccca atggtcacta cggcacatct attaaattga     1020
actgggccct ggaccccaac aggggatca tgcttgcaca taaaatgaac ggggagtctc       1080
ttcgcccaga tcatggtcgt ccgctgaggg ccgtcgtgcc cggtcaaata ggaggacgaa     1140
gtgttaagtg gctgaagagg ctgatcttga ccgatgcacc aagcgacaac tggtacagct     1200
tatcagctgc atatctctat atctccttat catcctgaca tccacttact aaagtgactg     1260
cagtgggtcc tgctaccttt ccccgtcaag gagcttatcg atagcagtac tagcgcgtgc     1320
gctgtaggtc aattgcgact tggaagacat gttggcgatg gaggggtagc gcggggttct     1380
gcaaatattg tataaatgag cacttagtgg ttgaaactgg cttattagta ggttagtact     1440
tcgagttttc agtaattaga caaaataatc aggatgtcca actactaact cttgatatat     1500
ggaatgaaat gtagatacaa actgcacgac aattgccgcg aaaaattaaa ttgaatctat     1560 ggagggact gtcatgcact agccacacgt ttctccgcct gtggggtgag ccacatgcct      1620
cattttgacc aaacacatcg atgcagtcac atgtagataa gattagggcc tatccttagg     1680
gtacattagt gatacccac tctaagaaaa tagaccaatc tccagctgca ccttcagaca       1740
ctccggtaca aattctcgtc tatgttggag attgttgtga cttgaaaca tgaccctga        1800 ccctgatttt gaatttgtcc atatatcgag gcaggtgtct tattcgtacg gagagggtat     1860
ctgtcgtaga cacatagtag tagtcatttc gagtgctgaa tttataaatc gcatcatact     1920
tgcgacatac tgccataaaa ggagtacgta tccaccacta cttattgcgc accaacacgc     1980
ttcaggtatg catcccatcc ctccttctgg tactgcttcg ccgcctccac gggatcagga     2040
gcagcataaa ttccacggcc agcaataata aagtcggcac cgcgtccaac agccgactca     2100
ggagtttggt actgctgtcc cagcttgtca cccttgagg agaggttgac acctgtcgtg       2160
aagacgacaa atcttcctc ctccgaaggc gagctaactt cagactgaac ctcgccaagg       2220
tgacgtgtcg agacgaatcc catcacaaac ttcttatact tccgagcata gtcaacagaa     2280
gaagtagtat attgaccggt agccaaagat cccttggagg tcatctccgc aaggatcaaa     2340
aggcccctct cggagccgta ggggaagtcc tcggccgaag cagtctgggc cagagcctcg     2400
acgataccct caccgggcag aatactgcag ttgatgatgt gggcccactc agagatacgc     2460
agagtgccgc catggtactg cttttggact gtgtttccga tatcgatgaa cttgcgatct     2520
tcgaagatga ggaaattgtg cttctctgca agggccttca gaccggtgat ggtttcttcg     2580
ctgaaatcgg agaggatatc gatgtgagtt ttgatcacgg caatgtacgg accgagtcct     2640
gttatataat ccaccattaa ccattactag atcacatgta agtggcatcc ccggtgcgca     2700
tacggtcagc caaatccagc agctctttgg tggttgtcac gtcggcggaa acggtgacat     2760
tggttttctt ggcctcggca acctcgaaga gcttctttac gagcgcattg gggtgcttgc     2820
tagcgcgtgc gctgtaggtc aattgcgact tggaagacat gttggcgatg gaggggtagc     2880
gcggggttct gcaaatattg tataaatgag cacttagtgg ttgaaactgg cttattagta     2940
ggttagtact tcgagttttc agtaattaga caaaataatc aggatgtcca actactaact     3000
```

```
cttgatatat ggaatgaaat gtagatacaa actgcacgac aattgccgcg aaaaattaaa   3060
ttgaatctat ggaggggact gtcatgcact agccacacgt ttctccgcct gtggggtgag   3120
ccacatgcct cattttgacc aaacacatcg atgcagtcac atgtagataa gattagggcc   3180
tatccttagg gtaccgcgct aggaggtggt cgaatacaca tgtaggcgct tctctggatg   3240
caaaagtcgt gccggacctg ccgaaagact ttgaagatgc gttcacgcca tctaagttgc   3300
gtagataatt cacaaaaagg gatgtttgtt tccggaatgt agcaaagagc tgataggcaa   3360
tagcctcact ttcgtggcgc acgccgctcg ttccatccat cctcgacaat ggagcaaatg   3420
tcaaaatcgt accgaaaata ctttccagca gcttcgctgc atcagcatgt cttttgctga   3480
gaaagagcgc aaaaagcatt tgatcgagaa tatcttcatg ataatctcta agtctaggga   3540
cagaatgtgc tgcttctatc gtgccatcaa tatcaccgcg gtcgaggcag cgttcaatct   3600
tagccaggct atcttggaac cgctgccaag tcgagccaat gccgacatga aagcaataat   3660
cactcaatga gagcacgaaa tgctggcagt caatgcgaaa tttctggtac acgtttcgag   3720
ggtgcccaga tagggagtct ctccccgtag aatcacgaat gagacctttg acgaccgaaa   3780
ccattcgaag gagtcgaagc agatgcttga aaagacgatc atacttgtta gcgatcgcg   3840 acgtaatgat agcttccagg acgtctgatg gtttgtattg aagacgtagg aaatccaaag   3900
cttgcatgcc tgcaggtcga cctgcagcca agcttggcgt aatcatggtc atagctgttt   3960
cctgtgtgaa attgttatcc gctcacaatt ccacacaaca tacgagccgg aagcataaag   4020
tgtaaagcct ggggtgccta atgagtgagc taactcacat taattgcgtt gcgctcactg   4080
cccgctttcc agtcgggaaa cctgtcgtgc cagctgcatt aatgaatcgg ccaacgcgcg   4140
gggagaggcg gtttgcgtat tgggcgctct tccgcttcct cgctcactga ctcgctgcgc   4200
tcggtcgttc ggctgcggcg agcggtatca gctcactcaa aggcggtaat acggttatcc   4260
acagaatcag gggataacgc aggaaagaac atgtgagcaa aaggccagca aaaggccagg   4320
aaccgtaaaa aggccgcgtt gctggcgttt ttccataggc tccgcccccc tgacgagcat   4380
cacaaaaatc gacgctcaag tcagaggtgg cgaaacccga caggactata agataccag   4440 gcgtttcccc ctggaagctc cctcgtgcgc tctcctgttc cgaccctgcc gcttaccgga   4500
tacctgtccg cctttttccc ttcgggaagc gtggcgcttt ctcatagctc acgctgtagg   4560
tatctcagtt cggtgtaggt cgttcgctcc aagctgggct gtgtgcacga accccccgtt   4620
cagcccgacc gctgcgcctt atccggtaac tatcgtcttg agtccaaccc ggtaagacac   4680
gacttatcgc cactggcagc agccactggt aacaggatta gcagagcgag gtatgtaggc   4740
ggtgctacag agttcttgaa gtggtggcct aactacggct acactagaag aacagtattt   4800
ggtatctgcg ctctgctgaa gccagttacc ttcggaaaaa gagttggtag ctcttgatcc   4860
ggcaaacaaa ccaccgctgg tagcggtggt ttttttgttt gcaagcagca gattacgcgc   4920
agaaaaaaag gatctcaaga agatcctttg atcttttcta cggggtctga cgctcagtgg   4980
aacgaaaact cacgttaagg gattttggtc atgagattat caaaaaggat cttcacctag   5040
atccttttaa attaaaaatg aagttttaaa tcaatctaaa gtatatatga gtaaacttgg   5100
tctgacagtt accaatgctt aatcagtgag gcacctatct cagcgatctg tctatttcgt   5160
tcatccatag ttgcctgact ccccgtcgtg tagataacta cgatacggga gggcttacca   5220
tctggcccca gtgctgcaat gataccgcga gacccacgct caccggctcc agatttatca   5280
gcaataaacc agccagccgg aagggccgag cgcagaagtg gtcctgcaac tttatccgcc   5340
tccatccagt ctattaattg ttgccgggaa gctagagtaa gtagttcgcc agttaatagt   5400
```

-continued

| | |
|---|---|
| ttgcgcaacg ttgttgccat tgctacaggc atcgtggtgt cacgctcgtc gtttggtatg | 5460 |
| gcttcattca gctccggttc ccaacgatca aggcgagtta catgatcccc catgttgtgc | 5520 |
| aaaaaagcgg ttagctcctt cggtcctccg atcgttgtca gaagtaagtt ggccgcagtg | 5580 |
| ttatcactca tggttatggc agcactgcat aattctctta ctgtcatgcc atccgtaaga | 5640 |
| tgcttttctg tgactggtga gtactcaacc aagtcattct gagaatagtg tatgcggcga | 5700 |
| ccgagttgct cttgcccggc gtcaatacgg gataataccg cgccacatag cagaacttta | 5760 |
| aaagtgctca tcattggaaa acgttcttcg gggcgaaaac tctcaaggat cttaccgctg | 5820 |
| ttgagatcca gttcgatgta acccactcgt gcacccaact gatcttcagc atcttttact | 5880 |
| ttcaccagcg tttctgggtg agcaaaaaca ggaaggcaaa atgccgcaaa aaagggaata | 5940 |
| agggcgacac ggaaatgttg aatactcata ctcttccttt tcaatatta ttgaagcatt | 6000 |
| tatcagggtt attgtctcat gagcggatac atatttgaat gtatttagaa aaataaacaa | 6060 |
| ataggggttc cgcgcacatt tccccgaaaa gtgccacctg acgtctaaga accattatt | 6120 |
| atcatgacat aacctataa aaataggcgt atcacgaggc cctttcgtc | 6169 |

<210> SEQ ID NO 17
<211> LENGTH: 9971
<212> TYPE: DNA
<213> ORGANISM: Artificial Sequence
<220> FEATURE:
<223> OTHER INFORMATION: complete DNA sequence of plasmid pJaL736
<220> FEATURE:
<221> NAME/KEY: misc_feature
<222> LOCATION: (6242)..(6242)
<223> OTHER INFORMATION: n is a, c, g, or t

<400> SEQUENCE: 17

| | |
|---|---|
| agcgcccaat acgcaaaccg cctctccccg cgcgttggcc gattcattaa tgcagctggc | 60 |
| acgacaggtt tcccgactgg aaagcgggca gtgagcgcaa cgcaattaat gtgagttagc | 120 |
| tcactcatta ggcaccccag gctttacact ttatgcttcc ggctcgtatg ttgtgtggaa | 180 |
| ttgtgagcgg ataacaattt cacacaggaa acagctatga ccatgattac gccaagctca | 240 |
| gaattaaccc tcactaaagg gactagtcct gcaggtttaa acgaattcgc ccttgacgaa | 300 |
| ttctctagaa gatctctcga ggagctcaag ctttcgcgag ctcgagatct gtataaagaa | 360 |
| ggtatgagtt ataactgctc cactcctatc cttatcaggt tgcttgcacc ggctgtcatg | 420 |
| cttgtcccct tgagccgtta cattctcaca ctctgaaagg gttttttaaca tcgccggagc | 480 |
| tcttctatgt tcgaaatcat ggcccagtcc ctcatatcaa ggatgaagat atccctcact | 540 |
| gggaaattag catcgaaggg ttagtatagt gctaggttct ctgccaaaca tccgttaacc | 600 |
| aaagtataga ctggtagaga agcctttggt actaaacttc cgacaagtgt tgcagcagta | 660 |
| cgaccaaata acagcgccta tcaccctcgt atgtgctggc aatcgacgca aagagcaaaa | 720 |
| cattgtacgt aaaacgaaag gttttcctg gggatcggcg ggactatcga ctgccctctt | 780 |
| cactggccca ttgctggcgg atattctccg cagtgcgaaa ccctgcgta agcgaaata | 840 |
| cgtctgtatg gaaggagcgg ataagctggt atgctgtacc tctatcttat gatgataatt | 900 |
| gctaagttcg ccgcagccca atggtcacta cggcacatct attaaattga actgggccct | 960 |
| ggaccccaac aggggatca tgcttgcaca taaaatgaac ggggagtctc ttcgcccaga | 1020 |
| tcatggtcgt ccgctgaggg ccgtcgtgcc cggtcaaata ggaggacgaa gtgttaagtg | 1080 |
| gctgaagagg ctgatcttga ccgatgcacc aagcgacaac tggtacagct tatcagctgc | 1140 |
| atatctctat atctccttat catcctgaca tccacttact aaagtgactg cagtgggtcc | 1200 |

```
tgctaccttt ccccgtcaag gagcttatcg atagcagtac tagcgcgtgc gctgtaggtc    1260
aattgcgact tggaagacat gttggcgatg gaggggtagc gcggggttct gcaaatattg    1320
tataaatgag cacttagtgg ttgaaactgg cttattagta ggttagtact tcgagttttc    1380
agtaattaga caaataatc aggatgtcca actactaact cttgatatat ggaatgaaat     1440
gtagatacaa actgcacgac aattgccgcg aaaattaaa ttgaatctat ggaggggact     1500
gtcatgcact agccacacgt ttctccgcct gtggggtgag ccacatgcct cattttgacc    1560
aaacacatcg atgcagtcac atgtagataa gattagggcc tatccttagg gtacattagt    1620 gatacccac tctaagaaaa tagaccaatc tccagctgca ccttcagaca ctccggtaca     1680
aattctcgtc tatgttggag attgttgtga ctttgaaaca tgaccttga ccctgatttt     1740 gaatttgtcc atatatcgag gcaggtgtct tattcgtacg gagagggtat ctgtcgtaga    1800
cacatagtag tagtcatttc gagtgctgaa tttataaatc gcatcatact tgcgacatac    1860
tgccataaaa ggagtacgta tccaccacta cttattgcgc accaacacgc ttcaggtatg    1920
catcccatcc ctccttctgg tactgcttcg ccgcctccac gggatcagga gcagcataaa    1980
ttccacggcc agcaataata aagtcggcac cgcgtccaac agccgactca ggagtttggt    2040
actgctgtcc cagcttgtca cccttcgagg agaggttgac acctgtcgtg aagacgacaa    2100
aatcttcctc ctccgaaggc gagctaactt cagactgaac ctcgccaagg tgacgtgtcg    2160
agacgaatcc catcacaaac ttcttatact tccgagcata gtcaacagaa gaagtagtat    2220
attgaccggt agccaaagat cccttggagg tcatctccgc aaggatcaaa aggcccctct    2280
cggagccgta ggggaagtcc tcggccgaag cagtctgggc cagagcctcg acgatccct     2340 caccgggcag aatactgcag ttgatgatgt gggcccactc agagatacgc agagtgccgc    2400
catggtactg cttttggact gtgtttccga tatcgatgaa cttgcgatct tcgaagatga    2460
ggaaattgtg cttctctgca agggccttca gaccggtgat ggtttcttcg ctgaaatcgg    2520
agaggatatc gatgtgagtt ttgatcacgg caatgtacgg accgagtcct gttatataat    2580
ccaccattaa ccattactag atcacatgta agtggcatcc ccggtgcgca tacggtcagc    2640
caaatccagc agctctttgg tggttgtcac gtcggcggaa acggtgacat tggttttctt    2700
ggcctcggca acctcgaaga gcttctttac gagcgcattg gggtgcttgc tagcgcgtgc    2760
gctgtaggtc aattgcgact tggaagacat gttggcgatg gaggggtagc gcggggttct    2820
gcaaatattg tataaatgag cacttagtgg ttgaaactgg cttattagta ggttagtact    2880
tcgagttttc agtaattaga caaataatc aggatgtcca actactaact cttgatatat     2940
ggaatgaaat gtagatacaa actgcacgac aattgccgcg aaaattaaa ttgaatctat     3000 ggaggggact gtcatgcact agccacacgt ttctccgcct gtggggtgag ccacatgcct    3060
cattttgacc aaacacatcg atgcagtcac atgtagataa gattagggcc tatccttagg    3120
gtaccgcgct aggaggtggt cgaatacaca tgtaggcgct tctctggatg caaaagtcgt    3180
gccggacctg ccgaaagact ttgaagatgc gttcacgcca tctaagttgc gtagataatt    3240
cacaaaaagg gatgtttgtt tccggaatgt agcaaagagc tgataggcaa tagcctcact    3300
ttcgtggcgc acgccgctcg ttccatccat cctcgacaat ggagcaaatg tcaaaatcgt    3360
accgaaaata ctttccagca gcttcgctgc atcagcatgt cttttgctga gaagagcgc     3420 aaaaagcatt tgatcgagaa tatcttcatg ataatctcta agtctaggga cagaatgtgc    3480
tgcttctatc gtgccatcaa tatcaccgcg gtcgaggcag cgttcaatct tagccaggct    3540
atcttggaac cgctgccaag tcgagccaat gccgacatga aagcaataat cactcaatga    3600
```

```
gagcacgaaa tgctggcagt caatgcgaaa tttctggtac acgtttcgag ggtgcccaga    3660
tagggagtct ctccccgtag aatcacgaat gagacctttg acgaccgaaa ccattcgaag    3720
gagtcgaagc agatgcttga aaagacgatc atacttgtta agcgatcgcg acgtaatgat    3780
agcttccagg acgtctgatg gtttgtattg aagacgtagg aaatccaaag cttgagctct    3840
gtacagtgac cggtgactct ttctggcatg cggagagacg gacggacgca gagagaaggg    3900
ctgagtaata agcgccactg cgccagacag ctctggcggc tctgaggtgc agtggatgat    3960
tattaatccg ggaccggccg cccctccgcc ccgaagtgga aaggctggtg tgcccctcgt    4020
tgaccaagaa tctattgcat catcggagaa tatggagctt catcgaatca ccggcagtaa    4080
gcgaaggaga atgtgaagcc aggggtgtat agcgtcggc gaaatagcat gccattaacc    4140
taggtacaga agtccaattg cttccgatct ggtaaaagat tcacgagata gtaccttctc    4200
cgaagtaggt agagcgagta cccgcgcgt aagctcccta attggcccat ccggcatctg    4260
tagggcgtcc aaatatcgtg cctctcctgc tttgcccggt gtatgaaacc ggaaaggccg    4320
ctcaggagct ggccagcggc gcagaccggg aacacaagct ggcagtcgac ccatccggtg    4380
ctctgcactc gacctgctga ggtccctcag tccctggtag gcagctttgc cccgtctgtc    4440
cgcccggtgt gtcggcgggg ttgacaaggt cgttgcgtca gtccaacatt tgttgccata    4500
ttttcctgct ctccccacca gctgtagatc gatcttggtg gcgtgaaact cccgcacctc    4560
ttcggccagc gccttgtaga agcgcgtatg gcttcgtacc ccggccatca acacgcgtct    4620
gcgttcgacc aggctgcgcg ttctcgcggc catagcaacc gacgtacggc gttgcgccct    4680
cgccggcagc aagaagccac ggaagtccgc ccggagcaga aaatgcccac gctactgcgg    4740
gtttatatag acggtcccca cgggatgggg aaaaccacca ccacgcaact gctggtggcc    4800
ctgggttcgc gcgacgatat cgtctacgta cccgagccga tgacttactg gcgggtgctg    4860
ggggcttccg agacaatcgc gaacatctac accacacaac accgcctcga ccagggtgag    4920
atatcggccg gggacgcggc ggtggtaatg acaagcgccc agataacaat gggcatgcct    4980
tatgccgtga ccgacgccgt tctggctcct catatcgggg gggaggctgg gagctcacat    5040 gcccccgcccc cggccctcac cctcatcttc gaccgccatc ccatcgccgc cctcctgtgc    5100
tacccggccg cgcggtacct tatgggcagc atgaccccc aggccgtgct ggcgttcgtg    5160
gccctcatcc cgccgacctt gcccggcacc aacatcgtgc ttggggccct tccggaggac    5220
agacacatcg accgcctggc caaacgccag cgccccggcg agcggctgga cctggctatg    5280
ctggctgcga ttcgccgcgt ttacgggcta cttgccaata cggtgcggta tctgcagtgc    5340
ggcgggtcgt ggcgggagga ctggggacag cttttcggga cggccgtgcc gccccagggt    5400
gccgagcccc agagcaacgc gggcccacga ccccatatcg gggacacgtt atttaccctg    5460
tttcggggcc ccgagttgct ggcccccaac ggcgacctgt ataacgtgtt tgcctgggcc    5520
ttggacgtct tggccaaacg cctccgttcc atgcacgtct ttatcctgga ttacgaccaa    5580
tcgcccgccg gctgccggga cgccctgctg caacttacct ccgggatggt ccagacccac    5640
gtcaccaccc ccgctccat accgacgata tgcgacctgg cgcgcacgtt tgcccgggag    5700 atggggagg ctaactgaaa cacggaagga acaataccg gaaggaaccc gcgctatccg    5760
gatcgatcca cttaacgtta ctgaaatcat caaacagctt gacgaatctg gatataagat    5820
cgttggtgtc gatgtcagct ccggagttga gacaaatggt gttcaggatc tcgataagat    5880
acgttcattt gtccaagcag caaagagtgc cttctagtga tttaatagct ccatgtcaac    5940
aagaataaaa cgcgtttcgg gtttaccctct tccagataca gctcatctgc aatgcattaa    6000
```

```
tgcattggac ctcgcaaccc tagtacgccc ttcaggctcc ggcgaagcag aagaatagct    6060
tagcagagtc tattttcatt ttcgggagac gagatcaagc agatcaacgg tcgtcaagag    6120
acctacgaga ctgaggaatc cgctcttggc tccacgcgac tatatatttg tctctaattg    6180
tactttgaca tgctcctctt ctttactctg atagcttgac tatgaaaatt ccgtcaccag    6240
cncctgggtt cgcaaagata attgcactgt ttcttccttg aactctcaag cctacaggag    6300
aattcgtcaa gggcgaattc gcggccgcta aattcaattc gccctatagt gagtcgtatt    6360
acaattcact ggccgtcgtt ttacaacgtc gtgactggga aaaccctggc gttacccaac    6420
ttaatcgcct tgcagcacat ccccctttcg ccagctggcg taatagcgaa gaggcccgca    6480
ccgatcgccc ttcccaacag ttgcgcagcc tatacgtacg gcagtttaag gtttacacct    6540
ataaaagaga gagccgttat cgtctgtttg tggatgtaca gagtgatatt attgacacgc    6600
cggggcgacg gatggtgatc ccctggcca gtgcacgtct gctgtcagat aaagtctccc    6660
gtgaacttta cccggtggtg catatcgggg atgaaagctg gcgcatgatg accaccgata    6720
tggccagtgt gccggtctcc gttatcgggg aagaagtggc tgatctcagc caccgcgaaa    6780
atgacatcaa aaacgccatt aacctgatgt tctggggaat ataaatgtca ggcatgagat    6840
tatcaaaaag gatcttcacc tagatccttt tcacgtagaa agccagtccg cagaaacggt    6900
gctgaccccg gatgaatgtc agctactggg ctatctggac aagggaaaac gcaagcgcaa    6960
agagaaagca ggtagcttgc agtgggctta catggcgata gctagactgg gcggttttat    7020
ggacagcaag cgaaccggaa ttgccagctg gggcgccctc tggtaaggtt gggaagccct    7080
gcaaagtaaa ctggatggct ttctcgccgc caaggatctg atggcgcagg ggatcaagct    7140
ctgatcaaga caggatga ggatcgtttc gcatgattga acaagatgga ttgcacgcag    7200
gttctccggc cgcttgggtg gagaggctat tcggctatga ctgggcacaa cagacaatcg    7260
gctgctctga tgccgccgtg ttccggctgt cagcgcaggg gcgcccggtt ctttttgtca    7320
agaccgacct gtccggtgcc ctgaatgaac tgcaagacga ggcagcgcgg ctatcgtggc    7380
tggccacgac gggcgttcct tgcgcagctg tgctcgacgt tgtcactgaa gcgggaaggg    7440
actggctgct attgggcgaa gtgccggggc aggatctcct gtcatctcac cttgctcctg    7500
ccgagaaagt atccatcatg gctgatgcaa tgcggcggct gcatacgctt gatccggcta    7560
cctgcccatt cgaccaccaa gcgaaacatc gcatcgagcg agcacgtact cggatggaag    7620
ccggtcttgt cgatcaggat gatctggacg aagagcatca ggggctcgcg ccagccgaac    7680
tgttcgccag gctcaaggcg agcatgcccg acggcgagga tctcgtcgtg acccatggcg    7740
atgcctgctt gccgaatatc atggtggaaa atggccgctt ttctggattc atcgactgtg    7800
gccggctggg tgtggcggac cgctatcagg acatagcgtt ggctacccgt gatattgctg    7860
aagagcttgg cggcgaatgg gctgaccgct tcctcgtgct ttacggtatc gccgctcccg    7920
attcgcagcg catcgccttc tatcgccttc ttgacgagtt cttctgaatt attaacgctt    7980
acaatttcct gatgcggtat tttctcctta cgcatctgtg cggtatttca caccgcatac    8040
aggtggcact tttcggggaa atgtgcgcgg aacccctatt tgtttatttt tctaaataca    8100
ttcaaatatg tatccgctca tgagacaata accctgataa atgcttcaat aatattgaaa    8160
aaggaagagt atgagtattc aacatttccg tgtcgccctt attcccttttt tgcggcatt    8220 ttgccttcct gtttttgctc acccagaaac gctggtgaaa gtaaaagatg ctgaagatca    8280
gttgggtgca cgagtgggtt acatcgaact ggatctcaac agcggtaaga tccttgagag    8340
ttttcgcccc gaagaacgtt ttccaatgat gagcactttt aaagttctgc tatgtggcgc    8400
```

```
ggtattatcc cgtattgacg ccgggcaaga gcaactcggt cgccgcatac actattctca   8460
gaatgacttg gttgagtact caccagtcac agaaaagcat cttacggatg gcatgacagt   8520
aagagaatta tgcagtgctg ccataaccat gagtgataac actgcggcca acttacttct   8580
gacaacgatc ggaggaccga aggagctaac cgcttttttg cacaacatgg gggatcatgt   8640
aactcgcctt gatcgttggg aaccggagct gaatgaagcc ataccaaacg acgagcgtga   8700
caccacgatg cctgtagcaa tggcaacaac gttgcgcaaa ctattaactg gcgaactact   8760
tactctagct tcccggcaac aattaataga ctggatggag gcggataaag ttgcaggacc   8820
acttctgcgc tcggcccttc cggctggctg gtttattgct gataaatctg gagccggtga   8880
gcgtgggtct cgcggtatca ttgcagcact ggggccagat ggtaagccct cccgtatcgt   8940
agttatctac acgacgggga gtcaggcaac tatggatgaa cgaaatagac agatcgctga   9000
gataggtgcc tcactgatta agcattggta actgtcagac caagtttact catatatact   9060
ttagattgat ttaaaacttc atttttaatt taaaaggatc taggtgaaga tcctttttga   9120
taatctcatg accaaaatcc cttaacgtga gttttcgttc cactgagcgt cagaccccgt   9180
agaaaagatc aaaggatctt cttgagatcc tttttttctg cgcgtaatct gctgcttgca   9240
aacaaaaaaa ccaccgctac cagcggtggt ttgtttgccg gatcaagagc taccaactct   9300
ttttccgaag gtaactggct tcagcagagc gcagatacca atactgtcc ttctagtgta   9360 gccgtagtta ggccaccact tcaagaactc tgtagcaccg cctacatacc tcgctctgct   9420
aatcctgtta ccagtggctg ctgccagtgg cgataagtcg tgtcttaccg ggttggactc   9480
aagacgatag ttaccggata aggcgcagcg gtcgggctga acggggggtt cgtgcacaca   9540
gcccagcttg gagcgaacga cctacaccga actgagatac ctacagcgtg agctatgaga   9600
aagcgccacg cttcccgaag ggagaaaggc ggacaggtat ccggtaagcg cagggtcgg   9660 aacaggagag cgcacgaggg agcttccagg gggaaacgcc tggtatcttt atagtcctgt   9720
cgggtttcgc cacctctgac ttgagcgtcg attttgtga tgctcgtcag ggggcggag   9780 cctatggaaa aacgccagca acgcggcctt tttacggttc ctgggctttt gctggccttt   9840
tgctcacatg ttctttcctg cgttatcccc tgattctgtg ataaccgta ttaccgcctt   9900 tgagtgagct gataccgctc gccgcagccg aacgaccgag cgcagcgagt cagtgagcga   9960
ggaagcggaa g                                                         9971

<210> SEQ ID NO 18
<211> LENGTH: 9321
<212> TYPE: DNA
<213> ORGANISM: Artificial Sequence
<220> FEATURE:
<223> OTHER INFORMATION: complete DNA sequence of plasmid pJaL958

<400> SEQUENCE: 18
agcttggcgg tgatattgat ggcacgatag aagcagcaca ttctgtccct agacttagag     60
attatcatga agatattctc gatcaaatgc tttttgcgct ctttctcagc aaaagacatg    120
ctgatgcagc gaagctgctg gaaagtattt tcggtacgat tttgacattt gctccattgt    180
cgaggatgga tggaacgagc ggcgtgcgcc acgaaagtga ggctattgcc tatcagctct    240
ttgctacatt ccggaaacaa acatcccttt tgtgaatta tctacgcaac ttagatggcg    300
tgaacgcatc ttcaaagtct ttcggcaggt ccggcacgac ttttgcatcc agagaagcgc    360
ctacatgtgt attcgaccac ctcctagcgc gcttggatat gaggaaatat tactgagagt    420
cgaaaacaag ctccaccgca ccagctcttc ttggagtttt atattaaaga atattcccag    480
```

```
ctcgttgtat tattctttt ctaccgtgct aatgtatcaa ggactttggt acctattaac      540
gttattattc gtgtgctatt cccaaacata accctgtata tgtttcgaac gccgttatga      600
cccatgtctt acatactcat taagtcattc ccttggataa tcccaattta gaagaagtga      660
aggtctgatt ctttccatcc ttccgccaac agtatcctcc gagccgattc ttccatggct      720
ggcggaccac aaatcaggac catactctca tcttctggag ccgcgtactc ctttaggagc      780
tcttcggata tgcgtcctcg gcggccagtc catgagtccg gcgctttgga tagggtgtgt      840
attatattac accttctgct gtcggttgcc atgaagccgt cgagctcagc ccggcaaagg      900
atatcttcct cctgtctgtt tccattgagg actgtacaag aggtgggatc ttgccggtcc      960
tgaaccacgg cgcgcaagac ctggaagatc ggtgtgatac cggttcctcc acaaatcatc     1020
ttaaacgacc gaacatggcg ttccttccca cttatgacaa ctcgtccatt tccaaggtat     1080
tcgaatctgc ctgtcggacc cttgcattca accacggagc ccaatggcag cctatccagg     1140
gccatcgtca tcttgccgcc tgccgagtg gctgttgcaa agtatacttt aaccagcaag     1200
tccacggtcc ctttctggct ggtttcagaa attgggtgt atgagcggat gatggcttcg     1260
ttgttggatg atgtgtcgag gactttgatc ataagatgct ggccgactgg taaacccaat     1320
gtttgatctt cgtgttccaa tttgaaacta aatattcgtg tatcccagga tatgtctttc     1380
ctttctttca atgttgcctt tgtccaagac cgtgattgga ggaacactgg gcgaatttca     1440
tcggtggagg atgatgcatc atccttgagt gcttttaaac cttccgggtc catcgttcca     1500
atatggtact caggcatcat cgcctttgcc gtctcgctat ctatggatag gtgtcaatag     1560
atggtacaat tgcagtgtga tatttttggg actcacgaat agcaaggaat tcctcagaga     1620
catccagacc agcagaggag ataatactct gcgctccgcc agggtggcct tcaagaaatg     1680
cttgaccatc atacacttct ccattcacga tgaaccatgg cttctcatcg caggaattct     1740
ccttgaattc ttcaaaacca atcactcggc ttagcccgtc tttcttcata ttaatgtctt     1800
gcacgggctc cggctccgtc ggctcctctc cttcgtgtct ttctcccag ttaccattcg     1860
tcaggtcacc cccagccttt ttgacgcgtt ccatccatcc tgtaggcata ctagggtggg     1920
tagggtgctc gaatctcaag ttcccgtttt ccttcgtaat tgtaacccgg aaccacgggt     1980
tgttcatcat tccgagaacg gaccagtaca tatcgcgagg ctgcacgccc aatgcttcgt     2040
ccatggctct tacaaggatg gcatcactgt tctcaagctc tgggatggtg atgcttagag     2100
accaaaaaca ccagcagaag caagtttcgc gccagtacat atctactttg cctccaaaaa     2160
gctcgccttc aaaatcacga tacttgtctt cggcatattc gatttccgcc aatctccaag     2220
ctataagtcc gttagctttg ataagcattc tcacacatcg agcgagcgag ggtgcgtaca     2280
tttgcctttg tctagggata tttctaccct ggtaaccctg cggccccac cggcgtatgc      2340
atatcctctg acagtatatg acggccctgc cgacaggaga tttaagacct cattgttttg     2400
gggatatgca acggcggagt tggtgtttag gtcataaatc gcataccgct catcgtgcca     2460
ccaatttcgg ttatttgatg ccatctcagg cgagaccatt gttctgggtt agggagttag     2520
acaaatgatg gaaatataaa ataagtgccc tttagacata cggtaagacg cggttgtcat     2580
tgatatggta ccagttgtcg cttggtgcat cggtcaagat cagcctcttc agccacttaa     2640
cacttcgtcc tcctatttga ccgggcacga cggccctcag cggacgacca tgatctgggc     2700
gaagagactc cccgttcatt ttatgtgcaa gcatgatccc cctgttgggg tccagggccc     2760
agttcaattt aatagatgtg ccgtagtgac cattgggctg cggcgaactt agcaattatc     2820
atcataagat agaggtacag cataccagct tatccgctcc ttccatacag acgtatttcg     2880
```

```
ctttacgcag gggtttcgca ctgcggagaa tatccgccag caatgggcca gtgaagaggg    2940
cagtcgatag tcccgccgat ccccaggaaa aacctttcgt tttacgtaca atgttttgct    3000
ctttgcgtcg attgccagca catacgaggg tgataggcgc tgttatttgg tcgtactgct    3060
gcaacacttg tcggaagttt agtaccaaag gcttctctac cagtctatac tttggttaac    3120
ggatgtttgg cagagaacct agcactatac taacccttcg atgctaattt cccagtgagg    3180
gatatcttca tccttgatat gagggactgg gccatgattt cgaacataga agagctccgg    3240
cgatgttaaa aaccctttca gagtgtgaga atgtaacggc tcaaggggac aagcatgaca    3300
gccggtgcaa gcaacctgat aaggatagga gtggagcagt tataactcat accttcttta    3360
tacagatctc gagctcgcga aagcttatgg tgttttgatc attttaaatt tttatatggc    3420
gggtggtggg caactcgctt gcgcgggcaa ctcgcttacc gattacgtta gggctgatat    3480
ttacgtaaaa atcgtcaagg gatgcaagac caaaccgtta aatttccgga gtcaacagca    3540
tccaagccca gtccttcac ggagaaaccc cagcgtccac atcacgagcg aaggaccacc    3600
tctaggcatc ggacgcacca tccaattaga agcagcaaag cgaaacagcc caagaaaaag    3660
gtcggcccgt cggccttttc tgcaacgctg atcacgggca gcgatccaac caacaccctc    3720
cagagtgact aggggcggaa atttatcggg attaatttcc actcaaccac aaatcacagt    3780
cgtccccggt aatttaacgg ctgcagacgg caatttaacg gcttctgcga atcgcttgga    3840
ttccccgccc ctggccgtag agcttaaagt atgtcccttg tcgatgcgat gtatgaatta    3900
gcttatggtg ttttgatcat tttaaatttt tatatggcgg gtggtgggca actcgcttgc    3960
gcgggcaact cgcttaccga ttacgttagg gctgatattt acgtaaaaat cgtcaaggga    4020
tgcaagacca aaccgttaaa tttccggagt caacagcatc caagcccaag tccttcacgg    4080
agaaacccca gcgtccacat cacgagcgaa ggaccacctc taggcatcgg acgcaccatc    4140
caattagaag cagcaaagcg aaacagccca agaaaaggt cggcccgtcg gccttttctg    4200
caacgctgat cacgggcagc gatccaacca acaccctcca gagtgactag gggcggaaat    4260
ttatcgggat aatttccac tcaaccacaa atcacagtcg tccccggtaa tttaacggct    4320
gcagacggca atttaacggc ttctgcgaat cgcttggatt ccccgcccct ggccgtagag    4380
cttaaagtat gtcccttgtc gatgcgatgt atgaattcat ggtgttttga tcattttaaa    4440
tttttatatg gcgggtggtg ggcaactcgc ttgcgcgggc aactcgctta ccgattacgt    4500
tagggctgat atttacgtaa aaatcgtcaa gggatgcaag accaaaccgt taaatttccg    4560
gagtcaacag catccaagcc caagtccttc acggagaaac cccagcgtcc acatcacgag    4620
cgaaggacca cctctaggca tcggacgcac catccaatta gaagcagcaa agcgaaacag    4680
cccaagaaaa aggtcggccc gtcggccttt tctgcaacgc tgatcacggg cagcgatcca    4740
accaacaccc tccagagtga ctaggggcgg aaatttatcg ggattaattt ccactcaacc    4800
acaaatcaca gtcgtccccg gtaatttaac ggctgcagac ggcaatttaa cggcttctgc    4860
gaatcgcttg gattccccgc ccctggccgt agagcttaaa gtatgtccct tgtcgatgcg    4920
atgtatcaca acatataaat actggcaagg gatgccatgc ttggagtttc caactcaatt    4980
tacctctatc cacacttctc ttccttcctc aatcctctat atacacaact ggggatcctt    5040
caccatgagg agctcccttg tgctgttctt tgtctctgcg tggacggcct ggctagccc    5100 tattcgtcct cgaccggtct cgcaggatct gtttaaccag ttcaatctct tgcacagta    5160 ttcagctgcc gcatactgcg gaaaaaacaa tgatgcccca gcaggtacaa acattacgtg    5220
cacgggaaat gcctgccccg aggtagagaa ggcggatgca acgtttctct actcgtttga    5280
```

```
agactctgga gtgggcgatg tcaccggctt ccttgctctc gacaacacga acaaattgat    5340
cgtcctctct ttccgtggct ctcgttccat agagaactgg atcgggaatc ttaacttcga    5400
cttgaaaaaa ataaatgaca tttgctccgg ctgcagggga catgacggct tcacttcgtc    5460
ctggaggtct gtagccgata cgttaaggca gaaggtggag gatgctgtga gggagcatcc    5520
caactatcgc gtggtgttta ccggacatag cttgggtggt gcattggcaa ctgttgccgg    5580
agcagacctg cgtggaaatg gtatgatat cgacgtgttt tcatatggcg ccccccgagt     5640
cggaaacagg gcttttgcag aattcctgac cgtacagacc ggcggaacac tctaccgcat    5700
tacccacacc aatgatattg tccctagact cccgccgcgc gaattcggtt acagccattc    5760
tagcccagaa tactggatca aatctggaac ccttgtcccc gtcacccgaa acgatatcgt    5820
gaagatagaa ggcatcgatg ccaccggcgg caataaccgg ccgaacattc cggatatccc    5880
tgcgcaccta tggtacttcg ggttaattgg gacatgtctt tagtgcgcgg cgcggctggg    5940
tcgactctag cgagctcgag atctagaggg tgactgacac ctggcggtag acaatcaatc    6000
catttcgcta tagttaaagg atggggatga gggcaattgg ttatatgatc atgtatgtag    6060
tgggtgtgca taatagtagt gaaatggaag ccaagtcatg tgattgtaat cgaccgacgg    6120
aattgaggat atccggaaat acagacaccg tgaaagccat ggtctttcct tcgtgtagaa    6180
gaccagacag acagtccctg atttacccctt gcacaaagca ctagaaaatt agcattccat   6240
ccttctctgc ttgctctgct gatatcactg tcattcaatg catagccatg agctcatctt    6300
agatccaagc acgtaattcc atagccgagg tccacagtgg agcagcaaca ttccccatca    6360
ttgctttccc caggggcctc ccaacgacta aatcaagagt atatctctac cgtccaatag    6420
atcgtcttcg cttcaaaatc tttgacaatt ccaagagggt cccatccat caaacccagt     6480 tcaataatag ccgagatgca tggtggagtc aattaggcag tattgctgga atgtcgggcc    6540
agttggccgg gtggtcattg gccgccagta cgactgtgat gccatctgcc actaaatccg    6600
atcattgatc caccgcccac gaggcgcgtc tttgcttttt gcgcggcgtc caggttcaac    6660
tctctcgctc tagatatcga tgaattcact ggccgtcgtt ttacaacgtc gtgactggga    6720
aaaccctggc gttacccaac ttaatcgcct tgcagcacat ccccctttcg ccagctggcg    6780
taatagcgaa gaggcccgca ccgatcgccc ttcccaacag ttgcgcagcc tgaatgcgga    6840
atggcgcctg atgcggtatt ttctccttac gcatctgtgc ggtatttcac accgcatatg    6900
gtgcactctc agtacaatct gctctgatgc cgcatagtta agccagcccc gacacccgcc    6960
aacacccgct gacgcgccct gacgggcttg tctgctcccg gcatccgctt acagacaagc    7020
tgtgaccgtc tccgggagct gcatgtgtca gaggttttca ccgtcatcac cgaaacgcgc    7080
gagacgaaag ggcctcgtga tacgcctatt tttataggtt aatgtcatga taataatggt    7140
ttcttagacg tcaggtggca cttttcgggg aaatgtgcgc ggaacccta ttgtttatt       7200 tttctaaata cattcaaata tgtatccgct catgagacaa taaccctgat aaatgcttca    7260
ataatattga aaaggaaga gtatgagtat tcaacatttc cgtgtcgccc ttattccctt     7320
ttttgcggca ttttgccttc ctgttttttgc tcacccagaa acgctggtga agtaaaaga    7380 tgctgaagat cagttgggtg cacgagtggg ttacatcgaa ctggatctca acagcggtaa    7440
gatccttgag agttttcgcc ccgaagaacg ttttccaatg atgagcactt ttaaagttct    7500
gctatgtggc gcggtattat cccgtattga cgccgggcaa gagcaactcg gtcgccgcat    7560
acactattct cagaatgact tggttgagta ctcaccagtc acagaaaagc atcttacgga    7620
tggcatgaca gtaagagaat tatgcagtgc tgccataacc atgagtgata cactgcggc    7680
```

```
caacttactt ctgacaacga tcggaggacc gaaggagcta accgcttttt tgcacaacat    7740
gggggatcat gtaactcgcc ttgatcgttg gaaccggag ctgaatgaag ccataccaaa    7800
cgacgagcgt gacaccacga tgcctgtagc aatggcaaca acgttgcgca aactattaac    7860
tggcgaacta cttactctag cttcccggca acaattaata gactggatgg aggcggataa    7920
agttgcagga ccacttctgc gctcggccct tccggctggc tggtttattg ctgataaatc    7980
tggagccggt gagcgtgggt ctcgcggtat cattgcagca ctggggccag atggtaagcc    8040
ctcccgtatc gtagttatct acacgacggg gagtcaggca actatggatg aacgaaatag    8100
acagatcgct gagataggtg cctcactgat taagcattgg taactgtcag accaagttta    8160
ctcatatata ctttagattg atttaaaact tcatttttaa tttaaaagga tctaggtgaa    8220 gatcctttt gataatctca tgaccaaaat cccttaacgt gagttttcgt tccactgagc    8280
gtcagacccc gtagaaaaga tcaaaggatc ttcttgagat cctttttttc tgcgcgtaat    8340
ctgctgcttg caaacaaaaa aaccaccgct accagcggtg gtttgtttgc cggatcaaga    8400
gctaccaact ctttttccga aggtaactgg cttcagcaga gcgcagatac caaatactgt    8460
ccttctagtg tagccgtagt taggccacca cttcaagaac tctgtagcac cgcctacata    8520
cctcgctctg ctaatcctgt taccagtggc tgctgccagt ggcgataagt cgtgtcttac    8580
cgggttggac tcaagacgat agttaccgga taaggcgcag cggtcgggct gaacggggg    8640 ttcgtgcaca gcccagct tggagcgaac gacctacacc gaactgagat acctacagcg    8700
tgagctatga gaaagcgcca cgcttcccga agggagaaag gcggacaggt atccggtaag    8760
cggcagggtc ggaacaggag agcgcacgag ggagcttcca gggggaaacg cctggtatct    8820
ttatagtcct gtcgggtttc gccacctctg acttgagcgt cgattttgt gatgctcgtc    8880 agggggggcgg agcctatgga aaaacgccag caacgcggcc ttttacggt tcctggcctt    8940 ttgctggcct tttgctcaca tgttctttcc tgcgttatcc cctgattctg tggataaccg    9000
tattaccgcc tttgagtgag ctgataccgc tcgccgcagc cgaacgaccg agcgcagcga    9060
gtcagtgagc gaggaagcgg aagagcgccc aatacgcaaa ccgcctctcc ccgcgcgttg    9120
gccgattcat taatgcagct ggcacgacag gtttcccgac tggaaagcgg gcagtgagcg    9180
caacgcaatt aatgtgagtt agctcactca ttaggcaccc caggctttac actttatgct    9240
tccggctcgt atgttgtgtg gaattgtgag cggataacaa tttcacacag gaaacagcta    9300
tgaccatgat tacgccaagc t    9321
```

<210> SEQ ID NO 19
<211> LENGTH: 8775
<212> TYPE: DNA
<213> ORGANISM: Artificial Sequence
<220> FEATURE:
<223> OTHER INFORMATION: complete DNA sequence of plasmid pMT2786

<400> SEQUENCE: 19

```
tgtataagct agcttatggt gttttgatca ttttaaattt ttatatgcg ggtggtgggc      60 aactcgcttg cgcgggcaac tcgcttaccg attacgttag ggctgatatt tacgtaaaaa     120
tcgtcaaggg atgcaagacc aaaccgttaa atttccggag tcaacagcat ccaagcccaa     180
gtccttcacg gagaaacccc agcgtccaca tcacgagcga aggaccacct ctaggcatcg     240
gacgcaccat ccaattagaa gcagcaaagc gaaacagccc aagaaaaagg tcggcccgtc     300
ggcctttcct gcaacgctga tcacgggcag cgatccaacc aacaccctcc agagtgacta     360
ggggcggaaa tttatcggga ttaatttcca ctcaaccaca aatcacagtc gtccccggta     420
```

-continued

```
atttaacggc tgcagacggc aatttaacgg cttctgcgaa tcgcttggat tccccgcccc    480
tggccgtaga gcttaaagta tgtcccttgt cgatgcgatg tatgaattca tggtgttttg    540
atcattttaa attttatat ggcgggtggt gggcaactcg cttgcgcggg caactcgctt     600
accgattacg ttagggctga tatttacgta aaaatcgtca agggatgcaa gaccaaaccg    660
ttaaatttcc ggagtcaaca gcatccaagc ccaagtcctt cacggagaaa ccccagcgtc    720
cacatcacga gcgaaggacc acctctaggc atcggacgca ccatccaatt agaagcagca    780
aagcgaaaca gcccaagaaa aaggtcggcc cgtcggcctt ttctgcaacg ctgatcacgg    840
gcagcgatcc aaccaacacc ctccagagtg actaggggcg gaaatttatc gggattaatt    900
tccactcaac cacaaatcac agtcgtcccc ggtaatttaa cggctgcaga cggcaattta    960
acggcttctg cgaatcgctt ggattccccg cccctggccg tagagcttaa agtatgtccc   1020
ttgtcgatgc gatgtatcac aacatataaa tactggcaag ggatgccatg cttggagttt   1080
ccaactcaat ttacctctat ccacacttct cttccttcct caatcctcta tatacacaac   1140
tggggatcca caatgaagtg ggtaaccttt atttcccttc ttttctctt tagctcggct    1200
tattccaggg gtgtgtttcg tcgagatgca cacaagagtg aggttgctca tcggtttaaa   1260
gatttgggag aagaaaattt caaagccttg gtgttgattg cctttgctca gtatcttcag   1320
cagtgtccat ttgaagatca tgtaaaatta gtgaatgaag taactgaatt tgcaaaaaca   1380
tgtgttgctg atgagtcagc tgaaaattgt gacaaatcac ttcataccct ttttggagac   1440
aaattatgca cagttgcaac tcttcgtgaa acctatggtg aaatggctga ctgctgtgca   1500
aaacaagaac ctgagagaaa tgaatgcttc ttgcaacaca agatgacaa cccaaacctc     1560
ccccgattgg tgagaccaga ggttgatgtg atgtgcactg cttttcatga caatgaagag   1620
acattttga aaaaatactt atatgaaatt gccagaagac atccttactt ttatgccccg     1680
gaactccttt tctttgctaa aaggtataaa gctgctttta cagaatgttg ccaagctgct   1740
gataaagctg cctgcctgtt gccaaagctc gatgaacttc gggatgaagg gaaggcttcg    1800
tctgccaaac agagactcaa gtgtgccagt ctccaaaaat ttggagaaag gctttcaaa    1860
gcatgggcag tagctcgcct gagccagaga tttcccaaag ctgagtttgc agaagtttcc   1920
aagttagtga cagatcttac caaagtccac acggaatgct gccatggaga tctgcttgaa   1980
tgtgctgatg acagggcgga ccttgccaag tatatctgtg aaaatcaaga ttcgatctcc   2040
agtaaactga aggaatgctg tgaaaaacct ctgttggaaa atcccactg cattgccgaa     2100
gtggaaaatg atgagatgcc tgctgacttg ccttcattag ctgctgattt tgttgaaagt   2160
aaggatgttt gcaaaaacta tgctgaggca aaggatgtct tcctgggcat gttttttgtat  2220
gaatatgcaa gaaggcatcc tgattactct gtcgtgctgc tgctgagact tgccaagaca   2280
tatgaaacca ctctagagaa gtgctgtgcc gctgcagatc tcatgaatg ctatgccaaa    2340
gtgttcgatg aatttaaacc tcttgtggaa gagcctcaga tttaatcaa acaaaattgt    2400
gagcttttg agcagcttgg agagtacaaa ttccagaatg cgctattagt tcgttacacc    2460
aagaaagtac cccaagtgtc aactccaact cttgtagagg tctcaagaaa cctaggaaaa   2520
gtgggcagca aatgttgtaa acatcctgaa gcaaaagaa tgccctgtgc agaagactat    2580
ctatccgtgg tcctgaacca gttatgtgtg ttgcatgaga aaacgccagt aagtgacaga   2640
gtcaccaaat gctgcacaga atccttggtg aacaggcgac catgcttttc agctctggaa   2700
gtcgatgaaa catacgttcc caaagagttt aatgctgaaa cattcacctt ccatgcagat   2760
atatgcacac tttctgagaa ggagagacaa atcaagaaac aaactgcact tgttgagctc   2820
```

```
gtgaaacaca agcccaaggc aacaaaagag caactgaaag ctgttatgga tgatttcgca   2880
gcttttgtag agaagtgctg caaggctgac gataaggaga cctgctttgc cgaggagggt   2940
aaaaaacttg ttgctgcaag tcaagctgcc ttaggcttat aactcgagat ctagaggtg   3000 actgacacct ggcggtagac aatcaatcca tttcgctata gttaaaggat ggggatgagg   3060
gcaattggtt atatgatcat gtatgtagtg ggtgtgcata atagtagtga aatggaagcc   3120
aagtcatgtg attgtaatcg accgacggaa ttgaggatat ccggaaatac agacaccgtg   3180
aaagccatgg tctttccttc gtgtagaaga ccagacagac agtccctgat ttacccttgc   3240
acaaagcact agaaaattag cattccatcc ttctctgctt gctctgctga tatcactgtc   3300
attcaatgca tagccatgag ctcatcttag atccaagcac gtaattccat agccgaggtc   3360
cacagtggag cagcaacatt ccccatcatt gctttcccca ggggcctccc aacgactaaa   3420
tcaagagtat atctctaccg tccaatagat cgtcttcgct tcaaaatctt tgacaattcc   3480
aagagggtcc ccatccatca aacccagttc aataatagcc gagatgcatg gtggagtcaa   3540
ttaggcagta ttgctggaat gtcggggcca gttggccggg tggtcattgg ccgcctgtga   3600
tgccatctgc cactaaatcc gatcattgat ccaccgccca cgaggcgcgt ctttgctttt   3660
tgcgcggcgt ccaggttcaa ctctctcctc tagactggaa acgcaaccct gaagggattc   3720
ttcctttgag agatggaagc gtgtcatatc tcttcggttc tacggcaggt ttttttctgc   3780
tctttcgtag catggcatgg tcacttcagc gcttatttac agttgctggt attgatttct   3840
tgtgcaaatt gctatctgac acttattagc tatggagtca ccacatttcc cagcaacttc   3900
cccacttcct ctgcaatcgc caacgtcctc tcttcactga gtctccgtcc gataacctgc   3960
actgcaaccg gtgccccatg gtacgcctcc ggatcatact cttcctgcac gagggcatca   4020
agctcactaa ccgccttgaa actctcattc ttcttatcga tgttcttatc cgcaaaggta   4080 accgaacaa ccacgctcgt gaaatccagc aggttgatca cagaggcata cccatagtac   4140
cggaactggt catgccgtac cgcagcggta ggcgtaatcg gcgcgatgat ggcgtccagt   4200
tccttcccgg ccttttcttc agcctcccgc catttctcaa ggtactccat ctggtaattc   4260
cacttctgga gatgcgtgtc ccagagctcg ttcatgttaa cagctttgat gttcgggttc   4320
agtaggtctt tgatatttgg aatcgccggc tcgccggatg cactgatatc gcgcattacg   4380
tcggcgctgc cgtcagccgc gtagatatgg gagatgagat cgtggccgaa atcgtgcttg   4440
tatggcgtcc acggggtcac ggtgtgaccg gctttggcga gtgcggcgac ggtggtttcc   4500
acgccgcgca ggataggagg gtgtggaagg acattgccgt cgaagttgta gtagccgata   4560
ttgagcccgc cgttcttgat cttggaggca ataatgtccg actcggactg gcgcagggc   4620 atgggatga ccttggagtc gtatttccat ggctcctgac cgaggacgga tttggtgaag   4680
aggcggaggt ctaacatact tcatcagtga ctgccggtct cgtatatagt ataaaaagca   4740
agaaaggagg acagtggagg cctggtatag agcaggaaaa gaaggaagag gcgaaggact   4800
caccctcaac agagtgcgta atcggcccga caacgctgtg caccgtctcc tgaccctcca   4860
tgctgttcgc catctttgca tacggcagcc gcccatgact cggccttaga ccgtacagga   4920
agttgaacgc ggccggcact cgaatcgagc caccgatatc cgttcctaca ccgatgacgc   4980
caccacgaat cccaacgatc gcaccctcac caccagaact gccgccgcac gaccagttct   5040
tgttgcgtgg gttgacggtg cgcccgatga tgttgttgac tgtctcgcag accatcaggg   5100
tctgcgggac agaggtcttg acgtagaaga cggcaccggc tttgcggagc atggttgtca   5160
gaaccgagtc cccttcgtcg tacttgttta gccatgagat gtagcccatt gatgtttcgt   5220
```

```
agccctggtg gcatatgtta gctgacaaaa agggacatct aacgactag gggcaacggt   5280
gtaccttgac tcgaagctgg tctttgagag agatggggag gccatggagt ggaccaacgg   5340
gtctcttgtg ctttgcgtag tattcatcga gttcccttgc ctgcgcgaga gcggcgtcag   5400
ggaagaactc gtgggcgcag tttgtctgca cagaagccag cgtcagcttg atagtcccat   5460
aaggtggcgt tgttacatct ccctgagagg tagaggggac cctactaact gctgggcgat   5520
tgctgcccgt ttacagaatg ctagcgtaac ttccaccgag gtcaactctc cggccgccag   5580
cttggacaca agatctgcag cggaggcctc tgtgatcttc agttcggcct ctgaaaggat   5640
caccgatttc tttgggaaat caataacgct gtcttccgca ggcagcgtct ggactttcca   5700
ttcatcaggg atggtttttg cgaggcgggc gcgcttatca gcggccagtt cttcccagga   5760
ttgaggcatt ctgtgttagc ttatagtcag gatgttggct cgacgagtgt aaactgggag   5820
ttggcatgag ggttatgtag gcttctttag ccccgcatcc ccctcattct cctcattgat   5880
cccggggag cggatggtgt tgataagaga ctaattatag ggtttagctg gtgcctagct   5940
ggtgattggc tggcttcgcc gaattttacg ggccaaggaa agctgcagaa ccgcggcact   6000
ggtaaacggt aattaagcta tcagccccat gctaacgagt ttaaattacg tgtattgctg   6060
ataaacacca acagagcttt actgaaagat gggagtcacg gtgtggcttc cccactgcga   6120
ttattgcaca agcagcgagg gcgaacttga ctgtcgtcgc tgagcagcct gcagtcaaac   6180
atacatatat atcaaccgcg aagacgtctg gccttgtaga acacgacgct ccctagcaac   6240
acctgccgtg tcagcctcta cggttgttac ttgcattcag gatgctctcc agcgggcgag   6300
ctattcaaaa tattcaaagc aggtatctcg tattgccagg attcagctga agcaacaggt   6360
gccaaggaaa tctgcgtcgg ttctcatctg ggcttgctcg gtcctggcgt agatctagag   6420
tcgacctgca ggcatgcggc gtaatcatgg tcatagctgt ttcctgtgtg aaattgttat   6480
ccgctcacaa ttccacacaa catacgagcc ggaagcataa agtgtaaagc ctggggtgcc   6540
taatgagtga gctaactcac attaattgcg ttgcgctcac tgcccgcttt ccagtcggga   6600
aacctgtcgt gccagctgca ttaatgaatc ggccaacgcg cggggagagg cggtttgcgt   6660
attgggcgct cttccgcttc ctcgctcact gactcgctgc gctcggtcgt tcggctgcgg   6720
cgagcggtat cagctcactc aaaggcggta atacggttat ccacagaatc agggggataac   6780
gcaggaaaga acatgtgagc aaaaggccag caaaaggcca ggaaccgtaa aaaggccgcg   6840
ttgctggcgt ttttccatag gctccgcccc cctgacgagc atcacaaaaa tcgacgctca   6900
agtcagaggt ggcgaaaccc gacaggacta taaagatacc aggcgtttcc ccctggaagc   6960
tccctcgtgc gctctcctgt tccgaccctg ccgcttaccg gatacctgtc cgcctttctc   7020
ccttcgggaa gcgtggcgct ttctcatagc tcacgctgta ggtatctcag ttcggtgtag   7080
gtcgttcgct ccaagctggg ctgtgtgcac gaaccccccg ttcagcccga ccgctgcgcc   7140
ttatccggta actatcgtct tgagtccaac ccggtaagac acgacttatc gccactggca   7200
gcagccactg gtaacaggat tagcagagcg aggtatgtag gcggtgctac agagttcttg   7260
aagtggtggc ctaactacgg ctacactaga agaacagtat ttggtatctg cgctctgctg   7320
aagccagtta ccttcggaaa aagagttggt agctcttgat ccgacaaaca aaccaccgct   7380
ggtagcggtg gtttttttgt ttgcaagcag cagattacgc gcagaaaaaa aggatctcaa   7440
gaagatcctt tgatcttttc tacgggtct gacgctcagt ggaacgaaaa ctcacgttaa   7500
gggattttgg tcatgagatt atcaaaaagg atcttcacct agatcctttt aaattaaaaa   7560
tgaagtttta aatcaatcta agtatatat gagtaaactt ggtctgacag ttaagcaagg   7620
```

| | |
|---|---|
| attttcttaa cttcttcggc gacagcatca ccgacttcgg tggtactgtt ggaaccacct | 7680 |
| aaatcaccag ttctgatacc tgcatccaaa acctttttaa ctgcatcttc aatggcctta | 7740 |
| ccttcttcag gcaagttcaa tgacaatttc aacatcattg cagcagacaa gatagtggcg | 7800 |
| atagggttga ccttattctt tggcaaatct ggagcagaac cgtggcatgg ttcgtacaaa | 7860 |
| ccaaatgcgg tgttcttgtc tggcaaagag gccaaggacg cagatggcaa caaacccaag | 7920 |
| gaacctggga taacggaggc ttcatcggag atgatatcac caaacatgtt gctggtgatt | 7980 |
| ataataccat ttaggtgggt tgggttctta actaggatca tggcggcaga atcaatcaat | 8040 |
| tgatgttgaa ccttcaatgt agggaattcg ttcttgatgg tttcctccac agttttctc | 8100 |
| cataatcttg aagaggccaa acattagct tatccaagg accaaatagg caatggtggc | 8160 |
| tcatgttgta gggccatgaa agcggccatt cttgtgattc tttgcacttc tggaacggtg | 8220 |
| tattgttcac tatcccaagc gacaccatca ccatcgtctt cctttctctt accaaagtaa | 8280 |
| atacctccca ctaattctct gacaacaacg aagtcagtac ctttagcaaa ttgtggcttg | 8340 |
| attggagata agtctaaaag agagtcggat gcaaagttac atggtcttaa gttggcgtac | 8400 |
| aattgaagtt ctttacggat ttttagtaaa ccttgttcag gtctaacact gccggtaccc | 8460 |
| catttaggac cacccacagc acctaacaaa acggcatcag ccttcttgga ggcttccagc | 8520 |
| gcctcatctg gaagtggaac acctgtagca tcgatagcag caccaccaat taatgatt | 8580 |
| tcgaaatcga acttgacatt ggaacgaaca tcagaaatag cttaagaac cttaatggct | 8640 |
| tcggctgtga tttcttgacc aacgtggtca cctggcaaaa cgacgatctt cttaggggca | 8700 |
| gacatactct cctttttca atattattga agcatttatc agggttattg tctcatgagc | 8760 |
| ggatacatat ttgaa | 8775 |

<210> SEQ ID NO 20
<211> LENGTH: 5857
<212> TYPE: DNA
<213> ORGANISM: Artificial Sequence
<220> FEATURE:
<223> OTHER INFORMATION: complete DNA sequence of plasmid pMT3155

<400> SEQUENCE: 20

| | |
|---|---|
| tttccatagg ctccgccccc ctgacgagca tcacaaaaat cgacgctcaa gtcagaggtg | 60 |
| gcgaaacccg acaggactat aaagatacca ggcgtttccc cctggaagct ccctcgtgcg | 120 |
| ctctcctgtt ccgaccctgc cgcttaccgg atacctgtcc gcctttctcc cttcgggaag | 180 |
| cgtggcgctt tctcatagct cacgctgtag gtatctcagt tcggtgtagg tcgttcgctc | 240 |
| caagctgggc tgtgtgcacg aaccccccgt tcagcccgac cgctgcgcct tatccggtaa | 300 |
| ctatcgtctt gagtccaacc cggtaagaca cgacttatcg ccactggcag cagccactgg | 360 |
| taacaggatt agcagagcga ggtatgtagg cggtgctaca gagttcttga agtggtggcc | 420 |
| taactacggc tacactagaa gaacagtatt tggtatctgc gctctgctga agccagttac | 480 |
| cttcggaaaa agagttggta gctcttgatc cgacaaacaa accaccgctg gtagcggtgg | 540 |
| tttttttgtt tgcaagcagc agattacgcg cagaaaaaaa ggatctcaag aagatccttt | 600 |
| gatcttttct acgggtctg acgctcagtg gaacgaaaac tcacgttaag ggattttggt | 660 |
| catgagatta tcaaaaagga tcttcaccta gatccttta aattaaaaat gaagttttaa | 720 |
| atcaatctaa agtatatatg agtaaacttg gtctgacagt taagcaagga ttttcttaac | 780 |
| ttcttcggcg acagcatcac cgacttcggt ggtactgttg aaccaccta aatcaccagt | 840 |
| tctgatacct gcatccaaaa ccttttaac tgcatcttca atggccttac cttcttcagg | 900 |

```
caagttcaat gacaatttca acatcattgc agcagacaag atagtggcga tagggttgac    960
cttattcttt ggcaaatctg gagcagaacc gtggcatggt tcgtacaaac caaatgcggt   1020
gttcttgtct ggcaaagagg ccaaggacgc agatggcaac aaacccaagg aacctgggat   1080
aacggaggct tcatcggaga tgatatcacc aaacatgttg ctggtgatta ataccatt    1140
taggtgggtt gggttcttaa ctaggatcat ggcggcagaa tcaatcaatt gatgttgaac   1200
cttcaatgta gggaattcgt tcttgatggt ttcctccaca gttttcctcc ataatcttga   1260
agaggccaaa acattagctt tatccaagga ccaaataggc aatggtggct catgttgtag   1320
ggccatgaaa gcggccattc ttgtgattct ttgcacttct ggaacggtgt attgttcact   1380
atcccaagcg acaccatcac catcgtcttc ctttctctta ccaaagtaaa tacctcccac   1440
taattctctg acaacaacga agtcagtacc tttagcaaat tgtggcttga ttggagataa   1500
gtctaaaaga gagtcggatg caaagttaca tggtcttaag ttggcgtaca attgaagttc   1560
tttacggatt tttagtaaac cttgttcagg tctaacactg ccggtacccc atttaggacc   1620
acccacagca cctaacaaaa cggcatcagc cttcttggag gcttccagcg cctcatctgg   1680
aagtggaaca cctgtagcat cgatagcagc accaccaatt aaatgatttt cgaaatcgaa   1740
cttgacattg aacgaacat cagaaatagc tttaagaacc ttaatggctt cggctgtgat    1800
ttcttgacca acgtggtcac ctggcaaaac gacgatcttc ttaggggcag acatactctt   1860
ccttttcaa tattattgaa gcatttatca gggttattgt ctcatgagcg atacatatt    1920
tgaatgtata agctagagcg ctgtcgacac tagtagatct cgatcgcgta cggctagcaa   1980
gctttggcca cctaggctag aaagaaggat tacctctaaa caagtgtacc tgtgcattct   2040
gggtaaacga ctcataggag agttgtaaaa aagtttcggc cggcgtattg ggtgttacgg   2100
agcattcact aggcaaccat gcatggttac tattgtatac ccatcttagt aggaatgatt   2160
ttcgaggttt atacctacga tgaatgtgtg tcctgtaggc ttgagagttc aaggaagaaa   2220
cagtgcaatt atctttgcga acccaggggc tggtgacgga atttcatag tcaagctatc    2280
agagtaaaga agaggagcat gtcaaagtac aattagagac aaatatatag tcgcgtggag   2340
ccaagagcgg attcctcagt ctcgtaggtc tcttgacgac cgttgatctg cttgatctcg   2400
tctcccgaaa atgaaaatag actctgctaa gctattcttc tgcttcgccg gagcctgaag   2460
ggcgtactag ggttgcgagg tccaatgcat taatgcattg cagatgagct gtatctggaa   2520
gaggtaaacc cgaaacgcgt tttattcttg ttgacatgga gctattaaat cactagaagg   2580
cactctttgc tgcttggaca aatgaacgta tcttatcgag atcctgaaca ccatttgtct   2640
caactccgga gctgacatcg acaccaacga tcttatatcc agattcgtca agctgtttga   2700
tgatttcagt aacgttaagt ggatcgatcc ggatagcgcg ggttccttcc ggtattgtct   2760
ccttccgtgt ttcagttagc ctcccccatc tcccgggcaa acgtgcgcgc tcagatctcg   2820
gtgacgggca ggaccggacg gggcggtacc ggcaggctga agtccagctg ccagaaaccc   2880
acgtcatgcc agttcccgtg cttgaagccg ccgccccgca gcatgccgcg ggggcatat    2940
ccgagcgcct cgtgcatgcg cacgctcggg tcgttgggca gcccgatgac agcgaccacg   3000
ctcttgaagc cctgtgcctc cagggacttc agcaggtggg tgtagagcgt ggagcccagt   3060
cccgtccgct ggtggcgggg ggagacgtac acggtcgact cggccgtcca gtcgtaggcg   3120
ttgcgtgcct tccaggggcc gcgtaggcg atgccggcga cctcgccgtc cacctcggcg    3180
acgagccagg gatagcgctc ccgcagacgg acgaggtcgt ccgtccactc ctgcggttcc   3240
tgcggctcgg tacggaagtt gaccgtgctt gtctcgatgt agtggttgac gatggtgcag   3300
```

```
accgccggca tgtccgcctc ggtggcacgg cggatgtcgg ccgggcgtcg ttctgggctc   3360
atggatccgg tggaagtaag atacgacgag tttgattgag aaaagacagg gtgattgtca   3420
agttcagtat ggaagaaaga gtagaagaag atcagacgac agggaagagc gatgacataa   3480
aaggtggaag acggaagaaa aacgaaccaa atcaatccca ctctatggcg ggggttggac   3540
tgcctgaggc cggcactggt ggggcttatc gataagttct cgtcaccgga tgcaatgcgc   3600
tgtcaactgc tgacttggcc ctgaacatcc tgtcctctac agatccatac tatacaatga   3660
tcccagttat agtgcggtaa ggtgcatatc atatctcatt ctcatgactc attcgacttt   3720
tttttagaga aaagtacata cgtggaacat acactaaacg caacaggtcg cgacaacact   3780
ggtatacaaa acggtccccg gtgaatgacg ttattagtgt ctatccccca ctcacacccg   3840
aaaagaataa tagaaactaa cagaaaaagc ggcccgagga taagaggaac attcaaacag   3900
aaggggaatc ataaaaaccg aaaaatgcaa ggaaaagaga actcaaatca ataattttca   3960
taatactgtc gagagtaata cggaccagcg tctctcaggg acatgcgtcg gcgcaaggca   4020
tcatccaatc tctcatctaa cacatccagc attcgtgttc gatagtctaa ctgcttctct   4080
cggcgctcaa gtcttgcttc ccgatcatcg agaattcggg tacggatatc gttgcgagct   4140
cgtggcccac gatatctttc gtcgaactcg ggtgcatcca aatcctcgga actaacaggg   4200
gcgtggataa tcttcgggcg atctcgggtc tgccgagcaa cttctcggct atggaccctc   4260
catagttgct tgtccgaatc cctgctgtcg gcggggatca catcaacata gtcacttggg   4320
tacttggtac ggccgtgtct gttgtcagat gcacccgagg gttgtttccg gtagtgggag   4380
cgatatcgag atggcccagg acgccttgaa gtagaggaat gccggcgaaa gagacttccg   4440
cgccagggct gcgcttcttt gcgtgtctct ccctcatgtt cagagtcatc tgtaactgag   4500
ctaacgtctt caaaatcgaa aatctctgaa tcgtcatccc caatactgct ggagtcgggg   4560
gccaactcta actctggttc cgccatgttg ggtggtttga cactacctcc ctgggtgaca   4620
ttctcaaagg aatgagattc atacgggtgg aatggctctt ccgtgggtt gttattggtt   4680 accgacaccc cggctgggtt gtacacgtta ttgacccctg ggtgttgcgc accagcactg   4740
ggaacgcctc tggtgtgctc ctttagcacc tcaatagctg ggccattctc cggagcagcc   4800
cttgcggtgt ggggcatggc tacctgtggg cgctggtgcg cacccacagg gacccctcta   4860
acatgctcct tcaggacctc agcactgggg ccgttctctg gagcagctct ggagacgtga   4920
ggtatgtgct gttgtacact accgctggca acacctctgg catgttcctt tagaacatca   4980
atcgcgggtc ccttctctgg cgcggcccgc gcgacgtggg gcatggctgc gtgtgggtgt   5040
accccgaaag agaaatgatc tggaacttct tgtggtagat gtccacggtt gaccaatggt   5100
cttcctcccg cctgctgtgc ctgaggttga ggaggggag gcggcggtgg cggggcttgc   5160
tgagtgaact cagggttaag ctgccgtggg atattgtgca cctgcaccat ggggggttgt   5220
tgtgcatgac ccatattggg ccttgcccac tgagggcgt tatcaacctc cgtgtccaat   5280
ggccgaggat catcgatgac cacgggattt tcggccttcg gctcagcccg cggctcaatt   5340
ttctccttag gcttgctagg taaatcgaac tccacttgcg ctactttggg acgcgaagag   5400
gtgataggct tccccatgat ctagagtcga cctgcaggca tgcggcgtaa tcatggtcat   5460 agctgttttcc tgtgtgaaat tgttatccgc tcacaattcc acacaacata cgagccggaa   5520
gcataaagtg taaagcctgg ggtgcctaat gagtgagcta actcacatta attgcgttgc   5580
gctcactgcc cgctttccag tcgggaaacc tgtcgtgcca gctgcattaa tgaatcggcc   5640
aacgcgcggg gagaggcggt ttgcgtattg ggcgctcttc cgcttcctcg ctcactgact   5700
```

```
cgctgcgctc ggtcgttcgg ctgcggcgag cggtatcagc tcactcaaag gcggtaatac    5760
ggttatccac agaatcaggg gataacgcag gaaagaacat gtgagcaaaa ggccagcaaa    5820
aggccaggaa ccgtaaaaag gccgcgttgc tggcgtt                             5857
```

<210> SEQ ID NO 21
<211> LENGTH: 7860
<212> TYPE: DNA
<213> ORGANISM: Artificial Sequence
<220> FEATURE:
<223> OTHER INFORMATION: complete DNA sequence of plasmid pMT3296

<400> SEQUENCE: 21

```
tttccatagg ctccgccccc ctgacgagca tcacaaaaat cgacgctcaa gtcagaggtg      60
gcgaaacccg acaggactat aaagatacca ggcgtttccc cctggaagct ccctcgtgcg     120
ctctcctgtt ccgaccctgc cgcttaccgg atacctgtcc gcctttctcc cttcgggaag     180
cgtggcgctt tctcatagct cacgctgtag gtatctcagt tcggtgtagg tcgttcgctc     240
caagctgggc tgtgtgcacg aaccccccgt tcagcccgac cgctgcgcct tatccggtaa     300
ctatcgtctt gagtccaacc cggtaagaca cgacttatcg ccactggcag cagccactgg     360
taacaggatt agcagagcga ggtatgtagg cggtgctaca gagttcttga agtggtggcc     420
taactacggc tacactagaa gaacagtatt tggtatctgc gctctgctga agccagttac     480
cttcggaaaa agagttggta gctcttgatc cgacaaacaa accaccgctg gtagcggtgg     540
tttttttgtt tgcaagcagc agattacgcg cagaaaaaaa ggatctcaag aagatccttt     600
gatcttttct acggggtctg acgctcagtg gaacgaaaac tcacgttaag ggattttggt     660
catgagatta tcaaaaagga tcttcaccta gatcctttta aattaaaaat gaagttttaa     720
atcaatctaa agtatatatg agtaaacttg gtctgacagt taagcaagga ttttcttaac     780
ttcttcggcg acagcatcac cgacttcggt ggtactgttg gaaccaccta atcaccagt     840 tctgatacct gcatccaaaa ccttttttaac tgcatcttca atggccttac cttcttcagg     900
caagttcaat gacaatttca acatcattgc agcagacaag atagtggcga tagggttgac     960
cttattcttt ggcaaatctg gagcagaacc gtggcatggt tcgtacaaac caaatgcggt    1020
gttcttgtct ggcaaagagg ccaaggacgc agatggcaac aaacccaagg aacctgggat    1080
aacggaggct tcatcggaga tgatatcacc aaacatgttg ctggtgatta ataccatt     1140 taggtgggtt gggttcttaa ctaggatcat ggcggcagaa tcaatcaatt gatgttgaac    1200
cttcaatgta gggaattcgt tcttgatggt ttcctccaca gtttttctcc ataatcttga    1260
agaggccaaa acattagctt tatccaagga ccaaataggc aatggtggct catgttgtag    1320
ggccatgaaa gcggccattc ttgtgattct ttgcacttct ggaacggtgt attgttcact    1380
atcccaagcg acaccatcac catcgtcttc ctttctctta ccaaagtaaa tacctcccac    1440
taattctctg acaacaacga agtcagtacc tttagcaaat gtggcttga ttggagataa    1500 gtctaaaaga gagtcggatg caaagttaca tggtcttaag ttggcgtaca attgaagttc    1560
tttacggatt tttagtaaac cttgttcagg tctaacactg ccggtacccc atttaggacc    1620
acccacagca cctaacaaaa cggcatcagc cttcttggag gcttccagcg cctcatctgg    1680
aagtggaaca cctgtagcat cgatagcagc accaccaatt aaatgatttt cgaaatcgaa    1740
cttgacattg gaacgaacat cagaaatagc tttaagaacc ttaatggctt cggctgtgat    1800
ttcttgacca acgtggtcac ctggcaaaac gacgatcttc ttaggggcag acatactctt    1860 ccttttttcaa tattattgaa gcatttatca gggttattgt ctcatgagcg gatacatatt    1920
```

```
tgaatgtata agctagagcg ctgtcgacac tagtagatct cgatcgcgta ccctcagcaa    1980
agccatcatt gcatgggatg gtcaaatcga cacgcgaaat ccaaggagag aacccgccat    2040
gactagcaga gagccctgcg ctcagatgaa tcgcaaagcc cgaggattgg tatcagcgaa    2100
agtatcatcc acaattttgt ctaccgactt gacatagata gtcccttccg atgaatatat    2160
tccacctctc ccaaccactg aggctaatat gcagttatca acaatccacg caaaccagct    2220
tgcattagac ccttctgctt ggataacatc cttgtttggc aggatttatc tgataggttc    2280
aatatagata ctagacttct ataattattc ggagtgatcc aaagctgatt cctatcttat    2340
cacccatgcc gtccgacgta tactgccaaa gattataatc agagatgaaa tgttggaaaa    2400
tagagctgag cattctgcat ctggtcgttg tggtctgtaa ccttggtgag gccccgtcta    2460
aaggaacgga tgctacacaa aactatggtt tgttagcatc caatatgtcg catctcttcc    2520
cactactttg attcaaacca tggtacttgg ccgcatgacg taaaatagac ccgctctgga    2580
tcaagattag tctaaagctt gtgatagggg gttacctttg taaaagacag gtgtcatggt    2640
aatactatgg gcgaatatca gtcaaggtat cctgctcagc ctcacccctt gcctttttgg    2700
gaagacttat agcaccctgc agattatcca ctgtgtaaat caacaagaat taatgacgct    2760
ttgcatctta ctcgtggttc agtagtgata tacgtgtctt tctgtttgac taccctacat    2820
tgctatgcag gcctagaccc acccccctga ggacttgcgt tatcctccta gaaattgatc    2880
tgcctagcat atggactcat agttatgtta gttccagaaa tcgctgctgg aattgaatcc    2940
ctgctcacta gtgccaacag agaaaaactg gaatgaacca atgagtaaat gctacgtaca    3000
aagaatgtat ttaacaccta tgatgtatga atcgactgtg tccatatcta gggatatttc    3060
tgctcagatg caaacctcgt ctcacttctg acaacctaat ccctcttttta ccggtattta    3120 tacatcgtat cccaaagtca agtacgtcag gtccgacgtc ctatccactc tacctgcaaa    3180
atattaacct cacctctaat agaggaagac catatcccac catgagactc tccctcaacc    3240
ttctactgat cgtcggatct gccgcagtcg cccgggctgc tctggtcccg gtcccggggg    3300
ctagcgaaga actttgcgga cgtcttggag tcatgtatta cgatcctgat aatctccccg    3360
agggtgtgga ggtgcatgag atacggaagt gtgccggaca tcccatgggt cgcgagaact    3420
attgggcctt gggtgattat ctgccgaggt ggtttcctta ggtattcttt caaagataac    3480
atggtccaat gaacggtcta tgatatgggt ctgagacacc ggatctcaat ggttgcctat    3540
agaccgtagg aaggatactt catgtacatg tcactggcta ctagtcactc attgcatttc    3600
agtagtaacc cccgaaatag ataagaaagc atggtcgtgc agtattagta tatttaggaa    3660
aaggtcatta atcattacca acacacttgc gttgagtcat cttactcaac cggcctcctt    3720
ccccacacaa catgaaactt cccatagata tgcaccctag gatctctcaa ctcattccgc    3780
acagaggcca agaaaactgc tacctccacc ggggaccagc cgagaaccct tgtacaaagc    3840
gcaagagcat acgactcaag actcataacc atgacttcgc gatggaaccg accggcttct    3900
tttaatcgct tttctttagc ccagggaccc atcgggaact acagaaatta agttaatacc    3960
cgatagatta acggagtatt aaaccagagg gagtctaggc tagaaagaag gattacctct    4020
aaacaagtgt acctgtgcat tctgggtaaa cgactcatag gagagttgta aaaaagtttc    4080
ggccggcgta ttgggtgtta cggagcattc actaggcaac catgcatggt tactattgta    4140
tacccatctt agtaggaatg attttcgagg tttataccta cgatgaatgt gtgtcctgta    4200
ggcttgagag ttcaaggaag aaacagtgca attatctttg cgaacccagg ggctggtgac    4260
ggaattttca tagtcaagct atcagagtaa agaagaggag catgtcaaag tacaattaga    4320
```

```
gacaaatata tagtcgcgtg gagccaagag cggattcctc agtctcgtag gtctcttgac    4380
gaccgttgat ctgcttgatc tcgtctcccg aaaatgaaaa tagactctgc taagctattc    4440
ttctgcttcg ccggagcctg aagggcgtac tagggttgcg aggtccaatg cattaatgca    4500
ttgcagatga gctgtatctg gaagaggtaa acccgaaacg cgttttattc ttgttgacat    4560
ggagctatta aatcactaga aggcactctt tgctgcttgg acaaatgaac gtatcttatc    4620
gagatcctga acaccatttg tctcaactcc ggagctgaca tcgacaccaa cgatctttata   4680 tccagattcg tcaagctgtt tgatgatttc agtaacgtta agtggatcga tccggatagc    4740
gcgggttcct tccggtattg tctccttccg tgtttcagtt agcctccccc atctcccggg    4800
caaacgtgcg cgctcagatc tcggtgacgg gcaggaccgg acgggcggt accggcaggc    4860 tgaagtccag ctgccagaaa cccacgtcat gccagttccc gtgcttgaag ccggccgccc    4920
gcagcatgcc gcgggggca tatccgagcg cctcgtgcat gcgcacgctc gggtcgttgg     4980
gcagcccgat gacagcgacc acgctcttga agccctgtgc ctccagggac ttcagcaggt    5040
gggtgtagag cgtggagccc agtcccgtcc gctggtggcg gggggagacg tacacggtcg    5100
actcggccgt ccagtcgtag gcgttgcgtg ccttccaggg gcccgcgtag gcgatgccgg    5160
cgacctcgcc gtccacctcg gcgacgagcc agggatagcg ctcccgcaga cggacgaggt    5220
cgtccgtcca ctcctgcggt tcctgcggct cggtacggaa gttgaccgtg cttgtctcga    5280
tgtagtggtt gacgatggtg cagaccgccg gcatgtccgc ctcggtggca cggcggatgt    5340
cggccgggcg tcgttctggg ctcatggatc cggtggaagt aagatacgac gagttttgatt   5400 gagaaaagac agggtgattg tcaagttcag tatggaagaa agagtagaag aagatcagac    5460
gacagggaag agcgatgaca taaaaggtgg aagacggaag aaaaacgaac caaatcaatc    5520
ccactctatg gcgggggttg gactgcctga ggccggcact ggtggggctt atcgataagt    5580
tctcgtcacc ggatgcaatg cgctgtcaac tgctgacttg gccctgaaca tcctgtcctc    5640
tacagatcca tactatacaa tgatcccagt tatagtgcgg taaggtgcat atcatatctc    5700
attctcatga ctcattcgac tttttttag agaaaagtac atacgtggaa catacactaa    5760
acgcaacagg tcgcgacaac actggtatac aaaacggtcc ccggtgaatg acgttattag    5820
tgtctatccc ccactcacac ccgaaaagaa taatagaaac taacagaaaa agcggcccga    5880
ggataagagg aacattcaaa cagaagggga atcataaaaa ccgaaaaatg caaggaaaag    5940
agaactcaaa tcaataattt tcataatact gtcgagagta atacggacca gcgtctctca    6000
gggacatgcg tcggcgcaag gcatcatcca atctctcatc taacacatcc agcattcgtg    6060
ttcgatagtc taactgcttc tctcggcgct caagtcttgc ttcccgatca tcgagaattc    6120
gggtacggat atcgttgcga gctcgtggcc cacgatatct ttcgtcgaac tcgggtgcat    6180
ccaaatcctc ggaactaaca ggggcgtgga taatcttcgg gcgatctcgg gtctgccgag    6240
caacttctcg gctatggacc ctccatagtt gcttgtccga atccctgctg tcggcgggga    6300
tcacatcaac atagtcactt gggtacttgg tacggccgtg tctgttgtca gatgcacccg    6360
agggttgttt ccggtagtgg gagcgatatc gagatggccc aggacgcctt gaagtagagg    6420
aatgccggcg aaagagactt ccgcgccagg gctgcgcttc tttgcgtgtc tctccctcat    6480
gttcagagtc atctgtaact gagctaacgt cttcaaaatc gaaatctct gaatcgtcat     6540 ccccaatact gctggagtcg ggggccaact ctaactctgg ttccgccatg ttgggtggtt    6600
tgacactacc tccctgggtg acattctcaa aggaatgaga ttcatacggg tggaatggct    6660
ctttccgtgg gttgttattg gttaccgaca ccccggctgg gttgtacacg ttattgaccc    6720
```

```
ctgggtgttg cgcaccagca ctgggaacgc ctctggtgtg ctcctttagc acctcaatag    6780
ctgggccatt ctccggagca gcccttgcgg tgtggggcat ggctacctgt gggcgctggt    6840
gcgcacccac agggacccct ctaacatgct ccttcaggac ctcagcactg ggccgttct     6900 ctggagcagc tctggagacg tgaggtatgt gctgttgtac actaccgctg gcaacacctc    6960
tggcatgttc ctttagaaca tcaatcgcgg gtcccttctc tggcgcggcc cgcgcgacgt    7020
ggggcatggc tgcgtgtggg tgtaccccga aagagaaatg atctggaact tcttgtggta    7080
gatgtccacg gttgaccaat ggtcttcctc ccgcctgctg tgcctgaggt tgaggagggg    7140
gaggcggcgg tggcggggct tgctgagtga actcagggtt aagctgccgt gggatattgt    7200
gcacctgcac catggggggt tgttgtgcat gacccatatt gggccttgcc cactgagggg    7260
cgttatcaac ctccgtgtcc aatggccgag gatcatcgat gaccacggga ttttcggcct    7320
tcggctcagc ccgcggctca attttctcct taggcttgct aggtaaatcg aactccactt    7380
gcgctacttt gggacgcgaa gaggtgatag gcttccccat gatctagagt cgacctgcag    7440
gcatgcggcg taatcatggt catagctgtt tcctgtgtga aattgttatc cgctcacaat    7500
tccacacaac atacgagccg gaagcataaa gtgtaaagcc tggggtgcct aatgagtgag    7560
ctaactcaca ttaattgcgt tgcgctcact gcccgctttc cagtcgggaa acctgtcgtg    7620
ccagctgcat taatgaatcg gccaacgcgc ggggagaggc ggtttgcgta ttgggcgctc    7680
ttccgcttcc tcgctcactg actcgctgcg ctcggtcgtt cggctgcggc gagcggtatc    7740
agctcactca aaggcggtaa tacgttatc cacagaatca ggggataacg caggaaagaa    7800
catgtgagca aaaggccagc aaaaggccag gaaccgtaaa aaggccgcgt tgctggcgtt    7860

<210> SEQ ID NO 22
<211> LENGTH: 7185
<212> TYPE: DNA
<213> ORGANISM: Artificial Sequence
<220> FEATURE:
<223> OTHER INFORMATION: complete DNA sequence of plasmid pMT3306

<400> SEQUENCE: 22
tgtataagct agcttatggt gttttgatca ttttaaattt ttatatggcg ggtggtgggc      60
aactcgcttg cgcgggcaac tcgcttaccg attacgttag gctgatatt tacgtaaaaa     120 tcgtcaaggg atgcaagacc aaaccgttaa atttccggag tcaacagcat ccaagcccaa    180
gtccttcacg gagaaacccc agcgtccaca tcacgagcga aggaccacct ctaggcatcg    240
gacgcaccat ccaattagaa gcagcaaagc gaaacagccc aagaaaaagg tcggcccgtc    300 ggcctttct gcaacgctga tcacgggcag cgatccaacc aacaccctcc agagtgacta    360
ggggcggaaa tttatcggga ttaatttcca ctcaaccaca atcacagtc gtccccggta     420 atttaacggc tgcagacggc aatttaacgg cttctgcgaa tcgcttggat tccccgcccc    480
tggccgtaga gcttaaagta tgtcccttgt cgatgcgatg tatgaattca tggtgttttg    540
atcattttaa attttatat ggcgggtggt gggcaactcg cttgcgcggg caactcgctt     600
accgattacg ttagggctga tatttacgta aaaatcgtca agggatgcaa gaccaaaccg    660 ttaaattcc ggagtcaaca gcatccaagc ccaagtcctt cacggagaaa ccccagcgtc     720
cacatcacga gcgaaggacc acctctaggc atcggacgca ccatccaatt agaagcagca    780
aagcgaaaca gcccaagaaa aaggtcggcc cgtcggcctt ttctgcaacg ctgatcacgg    840
gcagcgatcc aaccaacacc ctccagagtg actaggggcg gaaatttatc gggattaatt    900
tccactcaac cacaaatcac agtcgtcccc ggtaatttaa cggctgcaga cggcaattta    960
```

```
acggcttctg cgaatcgctt ggattccccg cccctggccg tagagcttaa agtatgtccc   1020
ttgtcgatgc gatgtatcac aacatataaa tactggcaag ggatgccatg cttggagttt   1080
ccaactcaat ttacctctat ccacacttct cttccttcct caatcctcta tatacacaac   1140
tggggatcca ccatgagact ctccctcaac cttctactga tcgtcggatc tgccgcagtc   1200
gcccgggctg ctctggtccc ggtcccgggg gctagcgaag aactttgcgg acgtcttgga   1260
gtcatgtatt acgatcctga taatctcccc gagggtgtgg aggtgcatga gatacggaag   1320
tgtgccggac atcccatggg tcgcgagaac tattggggct tgggtgatta tctgccgagg   1380
tggtttcctt agctcgagat ctagagggtg actgacacct ggcggtagac aatcaatcca   1440
tttcgctata gttaaaggat ggggatgagg gcaattggtt atatgatcat gtatgtagtg   1500
ggtgtgcata atagtagtga aatggaagcc aagtcatgtg attgtaatcg accgacggaa   1560
ttgaggatat ccggaaatac agacaccgtg aaagccatgg tctttccttc gtgtagaaga   1620
ccagacagac agtccctgat ttaccccttgc acaaagcact agaaaattag cattccatcc   1680
ttctctgctt gctctgctga tatcactgtc attcaatgca tagccatgag ctcatcttag   1740
atccaagcac gtaattccat agccgaggtc cacagtggag cagcaacatt ccccatcatt   1800
gctttcccca ggggcctccc aacgactaaa tcaagagtat atctctaccg tccaatagat   1860
cgtcttcgct tcaaaatctt tgacaattcc aagagggtcc ccatccatca aacccagttc   1920
aataatagcc gagatgcatg gtggagtcaa ttaggcagta ttgctggaat gtcgggcca    1980 gttggccggg tggtcattgg ccgcctgtga tgccatctgc cactaaatcc gatcattgat   2040
ccaccgccca cgaggcgcgt ctttgctttt tgcgcggcgt ccaggttcaa ctctctcctc   2100
tagactggaa acgcaaccct gaagggattc ttcctttgag agatggaagc gtgtcatatc   2160
tcttcggttc tacggcaggt ttttttctgc tctttcgtag catggcatgg tcacttcagc   2220
gcttatttac agttgctggt attgatttct tgtgcaaatt gctatctgac acttattagc   2280
tatggagtca ccacatttcc cagcaacttc cccacttcct ctgcaatcgc caacgtcctc   2340
tcttcactga gtctccgtcc gataacctgc actgcaaccg gtgccccatg gtacgcctcc   2400
ggatcatact cttcctgcac gagggcatca agctcactaa ccgcctttgaa actctcattc   2460 ttcttatcga tgttcttatc cgcaaaggta accggaacaa ccacgctcgt gaaatccagc   2520
aggttgatca cagaggcata cccatagtac cggaactggt catgccgtac cgcagcggta   2580
ggcgtaatcg cgcgatgat ggcgtccagt tccttcccgg ccttttcttc agcctcccgc    2640
catttctcaa ggtactccat ctggtaattc cacttctgga gatgcgtgtc ccagagctcg   2700
ttcatgttaa cagctttgat gttcgggttc agtaggtctt tgatatttgg aatcgccggc   2760
tcgccggatg cactgatatc gcgcattacg tcggcgctgc cgtcagccgc gtagatatgg   2820
gagatgagat cgtggccgaa atcgtgcttg tatggcgtcc acgggtcac ggtgtgaccg     2880 gctttggcga gtgcggcgac ggtggttttcc acgccgcgca ggataggagg gtgtggaagg   2940
acattgccgt cgaagttgta gtagccgata ttgagcccgc cgttcttgat cttggaggca   3000
ataatgtccg actcggactg cgccagggc atggggatga ccttggagtc gtatttccat    3060
ggctcctgac cgaggacgga tttggtgaag aggcggaggt ctaacatact tcatcagtga   3120
ctgccggtct cgtatatagt ataaaaagca agaaaggagg acagtggagg cctggtatag   3180
agcaggaaaa gaaggaagag gcgaaggact caccctcaac agagtgcgta atcggcccga   3240
caacgctgtg caccgtctcc tgaccctcca tgctgttcgc catctttgca tacggcagcc   3300
gcccatgact cggccttaga ccgtacagga agttgaacgc ggccggcact cgaatcgagc   3360
```

```
caccgatatc cgttcctaca ccgatgacgc caccacgaat cccaacgatc gcaccctcac   3420
caccagaact gccgccgcac gaccagttct tgttgcgtgg gttgacggtg cgcccgatga   3480
tgttgttgac tgtctcgcag accatcaggg tctgcgggac agaggtcttg acgtagaaga   3540
cggcaccggc tttgcggagc atggttgtca gaaccgagtc cccttcgtcg tacttgttta   3600
gccatgagat gtagcccatt gatgtttcgt agccctggtg gcatatgtta gctgacaaaa   3660
agggacatct aacgacttag gggcaacggt gtaccttgac tcgaagctgg tctttgagag   3720
agatggggag gccatggagt ggaccaacgg gtctcttgtg cttttgcgtag tattcatcga   3780 gttcccttgc ctgcgcgaga gcggcgtcag ggaagaactc gtgggcgcag tttgtctgca   3840
cagaagccag cgtcagcttg atagtcccat aaggtggcgt tgttacatct ccctgagagg   3900
tagaggggac cctactaact gctgggcgat tgctgcccgt ttacagaatg ctagcgtaac   3960
ttccaccgag gtcaactctc cggccgccag cttggacaca agatctgcag cggaggcctc   4020
tgtgatcttc agttcggcct ctgaaaggat caccgatttc tttgggaaat caataacgct   4080
gtcttccgca ggcagcgtct ggactttcca ttcatcaggg atggttttttg cgaggcgggc   4140 gcgcttatca gcgccagtt cttcccagga ttgaggcatt ctgtgttagc ttatagtcag   4200
gatgttggct cgacgagtgt aaactgggag ttggcatgag ggttatgtag gcttctttag   4260
ccccgcatcc ccctcattct cctcattgat cccgggggag cggatggtgt tgataagaga   4320
ctaattatag ggtttagctg gtgcctagct ggtgattggc tggcttcgcc gaattttacg   4380
ggccaaggaa agctgcagaa ccgcggcact ggtaaacggt aattaagcta tcagccccat   4440
gctaacgagt ttaaattacg tgtattgctg ataaacacca acagagcttt actgaaagat   4500
gggagtcacg gtgtggcttc cccactgcga ttattgcaca agcagcgagg gcgaacttga   4560
ctgtcgtcgc tgagcagcct gcagtcaaac atacatatat atcaaccgcg aagacgtctg   4620
gccttgtaga acacgacgct ccctagcaac acctgccgtg tcagcctcta cggttgttac   4680
ttgcattcag gatgctctcc agcgggcgag ctattcaaaa tattcaaagc aggtatctcg   4740
tattgccagg attcagctga agcaacaggt gccaaggaaa tctgcgtcgg ttctcatctg   4800
ggcttgctcg gtcctggcgt agatctagag tcgacctgca ggcatgcggc gtaatcatgg   4860
tcatagctgt ttcctgtgtg aaattgttat ccgctcacaa ttccacacaa catacgagcc   4920
ggaagcataa agtgtaaagc ctggggtgcc taatgagtga gctaactcac attaattgcg   4980
ttgcgctcac tgcccgcttt ccagtcggga aacctgtcgt gccagctgca ttaatgaatc   5040
ggccaacgcg cggggagagg cggtttgcgt attgggcgct cttccgcttc ctcgctcact   5100
gactcgctgc gctcggtcgt tcggctgcgg cgagcggtat cagctcactc aaaggcggta   5160
atacggttat ccacagaatc aggggataac gcaggaaaga acatgtgagc aaaaggccag   5220
caaaaggcca ggaaccgtaa aaaggccgcg ttgctggcgt ttttccatag gctccgcccc   5280
cctgacgagc atcacaaaaa tcgacgctca agtcagaggt ggcgaaaccc gacaggacta   5340
taaagatacc aggcgtttcc ccctggaagc tccctcgtgc gctctcctgt tccgaccctg   5400
ccgcttaccg gatacctgtc cgcctttctc ccttcgggaa gcgtggcgct ttctcatagc   5460
tcacgctgta ggtatctcag ttcggtgtag tcgttcgct ccaagctggg ctgtgtgcac   5520
gaaccccccg ttcagcccga ccgctgcgcc ttatccggta actatcgtct tgagtccaac   5580
ccggtaagac acgacttatc gccactggca gcagccactg gtaacaggat tagcagagcg   5640
aggtatgtag gcggtgctac agagttcttg aagtggtggc ctaactacgg ctacactaga   5700
agaacagtat ttggtatctg cgctctgctg aagccagtta ccttcggaaa aagagttggt   5760
```

```
agctcttgat ccgacaaaca aaccaccgct ggtagcggtg gttttttttgt ttgcaagcag    5820 cagattacgc gcagaaaaaa aggatctcaa gaagatcctt tgatcttttc tacggggtct    5880
gacgctcagt ggaacgaaaa ctcacgttaa gggattttgg tcatgagatt atcaaaaagg    5940
atcttcacct agatcctttt aaattaaaaa tgaagtttta atcaatcta aagtatatat    6000 gagtaaactt ggtctgacag ttaagcaagg attttcttaa cttcttcggc gacagcatca    6060
ccgacttcgg tggtactgtt ggaaccacct aaatcaccag ttctgatacc tgcatccaaa    6120
acctttttaa ctgcatcttc aatgccctta ccttcttcag gcaagttcaa tgacaatttc    6180
aacatcattg cagcagacaa gatagtggcg ataggggttga ccttattctt tggcaaatct    6240
ggagcagaac cgtggcatgg ttcgtacaaa ccaaatgcgg tgttcttgtc tggcaaagag    6300
gccaaggacg cagatggcaa caaacccaag gaacctggga taacggaggc ttcatcggag    6360
atgatatcac caaacatgtt gctggtgatt ataataccat ttaggtgggt tgggttctta    6420
actaggatca tggcggcaga atcaatcaat tgatgttgaa ccttcaatgt agggaattcg    6480
ttcttgatgg tttcctccac agttttttctc cataatcttg aagaggccaa aacattagct    6540
ttatccaagg accaaatagg caatggtggc tcatgttgta gggccatgaa agcggccatt    6600
cttgtgattc tttgcacttc tggaacggtg tattgttcac tatcccaagc gacaccatca    6660
ccatcgtctt cctttctctt accaaagtaa atacctccca ctaattctct gacaacaacg    6720
aagtcagtac ctttagcaaa ttgtggcttg attggagata agtctaaaag agagtcggat    6780
gcaaagttac atggtcttaa gttggcgtac aattgaagtt cttttacggat ttttagtaaa    6840 ccttgttcag gtctaacact gccggtaccc catttaggac cacccacagc acctaacaaa    6900
acggcatcag ccttcttgga ggcttccagc gcctcatctg gaagtggaac acctgtagca    6960
tcgatagcag caccaccaat taaatgattt cgaaatcga acttgacatt ggaacgaaca    7020
tcagaaatag ctttaagaac cttaatggct tcggctgtga tttcttgacc aacgtggtca    7080
cctggcaaaa cgacgatctt cttaggggca gacatactct tcctttttca atattattga    7140
agcatttatc agggttattg tctcatgagc ggatacatat ttgaa    7185
```

<210> SEQ ID NO 23
<211> LENGTH: 8009
<212> TYPE: DNA
<213> ORGANISM: Artificial Sequence
<220> FEATURE:
<223> OTHER INFORMATION: complete DNA sequence of plasmid pMT3328

<400> SEQUENCE: 23

```
tgtataagct agcttatggt gttttgatca ttttaaattt ttatatggcg ggtggtgggc      60
aactcgcttg cgcgggcaac tcgcttaccg attacgttag ggctgatatt tacgtaaaaa     120
tcgtcaaggg atgcaagacc aaaccgttaa atttccggag tcaacagcat ccaagcccaa     180
gtccttcacg gagaaacccc agcgtccaca tcacgagcga aggaccacct ctaggcatcg     240
gacgcaccat ccaattagaa gcagcaaagc gaaacagccc aagaaaaagg tcggcccgtc     300
ggccttttct gcaacgctga tcacgggcag cgatccaacc aacaccctcc agagtgacta     360
ggggcggaaa tttatcggga ttaatttcca ctcaaccaca aatcacagtc gtccccggta     420
atttaacggc tgcagacggc aatttaacgg cttctgcgaa tcgcttggat tccccgcccc     480
tggccgtaga gcttaaagta tgtcccttgt cgatgcgatg tatgaattca tggtgttttg     540
atcattttaa atttttatat ggcggtggt gggcaactcg cttgcgcggg caactcgctt     600
accgattacg ttagggctga tatttacgta aaaatcgtca aggatgcaa gaccaaaccg     660
```

```
ttaaatttcc ggagtcaaca gcatccaagc ccaagtcctt cacggagaaa ccccagcgtc    720
cacatcacga gcgaaggacc acctctaggc atcggacgca ccatccaatt agaagcagca    780
aagcgaaaca gcccaagaaa aaggtcggcc cgtcggcctt ttctgcaacg ctgatcacgg    840
gcagcgatcc aaccaacacc ctccagagtg actaggggcg gaaatttatc gggattaatt    900
tccactcaac cacaaatcac agtcgtcccc ggtaatttaa cggctgcaga cggcaattta    960
acggcttctg cgaatcgctt ggattccccg cccctggccg tagagcttaa agtatgtccc   1020
ttgtcgatgc gatgtatcac aacatataaa tactggcaag ggatgccatg cttggagttt   1080
ccaactcaat ttacctctat ccacacttct cttccttcct caatcctcta tatacacaac   1140
tggggatccg tcgaccttgg ggaagtcatc accgaatcta attacgatgt cctgggagct   1200
caatatatgg tgaagcagtg ccggaagtcg gtgaacttcc ttggtgctct tgaggccacc   1260
agatatgcga aattgatgac tgataagact gtctggctgg aagttggtgc ccataccatt   1320
tgctctggta tgatcaaagc aacattcggt ccccaggtta ccactgtggc atctcttcgc   1380
cgagaggaga atgcatggaa ggtcctctcc aatagtctat cggcccttca tttggctggc   1440
attgatatta attggaaaga atatcatcaa gacttcagct ccagccacca ggtgctccca   1500
cttccttctt acaagtggga tctcaagaac tactggatac cctacactaa caatttctgc   1560
cttacgaagg gtgctcccca aactgcaatt caagctgcac cacaaactac attcctgacc   1620
actgctgcgc aaaaggttgt tgagagtcgc gacgagaatt caatgattaa tgaccttttc   1680
ctaaatatac taatactgca cgaccatgct ttcttatcta tttcgggggt tactactgaa   1740
atgcaatgag tgactagtag ccagtgacat gtacatgaag tatccttcct acggtctata   1800
ggcaaccatt gagatccggt gtctcagacc catatcatag accgttcatt ggaccatgtt   1860
atctttgaaa gaatacctaa ggaaaccacc tcggcagata atcacccaag ccccaatagt   1920
tctcgcgacc catgggatgt ccggcacact tccgtatctc atgcacctcc acaccctcgg   1980
ggagattatc aggatcgtaa tacatgactc caagacgtcc gcaaagttct tcgctagccc   2040
ccgggaccgg gaccagagca gcccgggcga ctgcggcaga tccgacgatc agtagaaggt   2100
tgagggagag tctcatggtg ggatatggtc ttcctctatt agaggtgagg ttaatatttt   2160
gcaggtagag tggataggac gtcggacctg acgtacttga ctttgggata cctaggctcg   2220
agatctagag ggtgactgac acctggcggt agacaatcaa tccatttcgc tatagttaaa   2280
ggatggggat gagggcaatt ggttatatga tcatgtatgt agtgggtgtg cataatagta   2340
gtgaaatgga agccaagtca tgtgattgta atcgaccgac ggaattgagg atatccggaa   2400
atacagacac cgtgaaagcc atggtctttc cttcgtgtag aagaccagac agacagtccc   2460
tgatttaccc ttgcacaaag cactagaaaa ttagcattcc atccttctct gcttgctctg   2520
ctgatatcac tgtcattcaa tgcatagcca tgagctcatc ttagatccaa gcacgtaatt   2580
ccatagccga ggtccacagt ggagcagcaa cattccccat cattgctttc ccaggggcc    2640 tcccaacgac taaatcaaga gtatatctct accgtccaat agatcgtctt cgcttcaaaa   2700
tctttgacaa ttccaagagg gtccccatcc atcaaaccca gttcaataat agccgagatg   2760
catggtggag tcaattaggc agtattgctg gaatgtcggg gccagttggc cgggtggtca   2820
ttggccgcct gtgatgccat ctgccactaa atccgatcat tgatccaccg cccacgaggc   2880
gcgtctttgc ttttttgcgcg gcgtccaggt tcaactctct cctctagact ggaaacgcaa   2940
ccctgaaggg attcttcctt tgagagatgg aagcgtgtca tatctcttcg gttctacggc   3000 aggtttttt ctgctctttc gtagcatggc atggtcactt cagcgcttat ttacagttgc   3060
```

```
tggtattgat tcttgtgca aattgctatc tgacacttat tagctatgga gtcaccacat    3120
ttcccagcaa cttccccact tcctctgcaa tcgccaacgt cctctcttca ctgagtctcc    3180
gtccgataac ctgcactgca accggtgccc catggtacgc ctccggatca tactcttcct    3240
gcacgagggc atcaagctca ctaaccgcct tgaaactctc attcttctta tcgatgttct    3300
tatccgcaaa ggtaaccgga caaccacgc tcgtgaaatc cagcaggttg atcacagagg     3360
catacccata gtaccggaac tggtcatgcc gtaccgcagc ggtaggcgta atcggcgcga    3420
tgatggcgtc cagttccttc ccggccttt cttcagcctc ccgccatttc tcaaggtact      3480
ccatctggta attccacttc tggagatgcg tgtcccagag ctcgttcatg ttaacagctt    3540
tgatgttcgg gttcagtagg tctttgatat ttggaatcgc cggctcgccg gatgcactga    3600
tatcgcgcat tacgtcggcg ctgccgtcag ccgcgtagat atgggagatg agatcgtggc    3660
cgaaatcgtg cttgtatggc gtccacgggg tcacggtgtg accggctttg gcgagtgcgg    3720
cgacggtggt ttccacgccg cgcaggatag gagggtgtgg aaggacattg ccgtcgaagt    3780
tgtagtagcc gatattgagc ccgccgttct tgatcttgga ggcaataatg tccgactcgg    3840
actggcgcca gggcatgggg atgaccttgg agtcgtattt ccatggctcc tgaccgagga    3900
cggatttggt gaagaggcgg aggtctaaca tacttcatca gtgactgccg gtctcgtata    3960
tagtataaaa agcaagaaag gaggacagtg gaggcctggt atagagcagg aaaagaagga    4020
agaggcgaag gactcaccct caacagagtg cgtaatcggc ccgacaacgc tgtgcaccgt    4080
ctcctgaccc tccatgctgt tcgccatctt tgcatacggc agccgcccat gactcggcct    4140
tagaccgtac aggaagttga acgcggccgg cactcgaatc gagccaccga tatccgttcc    4200
tacaccgatg acgccaccac gaatcccaac gatcgcaccc tcaccaccag aactgccgcc    4260
gcacgaccag ttcttgttgc gtgggttgac ggtgcgcccg atgatgttgt tgactgtctc    4320
gcagaccatc agggtctgcg ggacagaggt cttgacgtag aagacggcac cggctttgcg    4380
gagcatggtt gtcagaaccg agtccccttc gtcgtacttg tttagccatg agatgtagcc    4440
cattgatgtt tcgtagccct ggtggcatat gttagctgac aaaaagggac atctaacgac    4500
ttaggggcaa cggtgtacct tgactcgaag ctggtctttg agagagatgg ggaggccatg    4560
gagtggacca acgggtctct tgtgctttgc gtagtattca tcgagttccc ttgcctgcgc    4620
gagagcggcg tcaggaaga actcgtgggc gcagtttgtc tgcacagaag ccagcgtcag    4680
cttgatagtc ccataaggtg gcgttgttac atctccctga gaggtagagg ggaccctact    4740
aactgctggg cgattgctgc ccgtttacag aatgctagcg taacttccac cgaggtcaac    4800
tctccggccg ccagcttgga cacaagatct gcagcggagg cctctgtgat cttcagttcg    4860
gcctctgaaa ggatcaccga tttctttggg aaatcaataa cgctgtcttc cgcaggcagc    4920
gtctggactt tccattcatc agggatggtt tttgcgaggc gggcgcgctt atcagcggcc    4980
agttcttccc aggattgagg cattctgtgt tagcttatag tcaggatgtt ggctcgacga    5040
gtgtaaactg ggagttggca tgagggttat gtaggcttct ttagccccgc atcccctca    5100 ttctcctcat tgatcccggg ggagcggatg tgttgataa gagactaatt ataggttta    5160 gctggtgcct agctggtgat tggctggctt cgccgaattt tacgggccaa ggaaagctgc    5220
agaaccgcgg cactggtaaa cggtaattaa gctatcagcc ccatgctaac gagttaaat    5280 tacgtgtatt gctgataaac accaacagag ctttactgaa agatgggagt cacggtgtgg    5340
cttccccact gcgattattg cacaagcagc gagggcgaac ttgactgtcg tcgctgagca    5400
gcctgcagtc aaacatacat atatatcaac cgcgaagacg tctggccttg tagaacacga    5460
```

```
cgctccctag caacacctgc cgtgtcagcc tctacggttg ttacttgcat tcaggatgct   5520
ctccagcggg cgagctattc aaaatattca aagcaggtat ctcgtattgc caggattcag   5580
ctgaagcaac aggtgccaag gaaatctgcg tcggttctca tctgggcttg ctcggtcctg   5640
gcgtagatct agagtcgacc tgcaggcatg cggcgtaatc atggtcatag ctgtttcctg   5700
tgtgaaattg ttatccgctc acaattccac acaacatacg agccggaagc ataaagtgta   5760
aagcctgggg tgcctaatga gtgagctaac tcacattaat tgcgttgcgc tcactgcccg   5820
ctttccagtc gggaaacctg tcgtgccagc tgcattaatg aatcggccaa cgcgcgggga   5880
gaggcggttt gcgtattggg cgctcttccg cttcctcgct cactgactcg ctgcgctcgg   5940
tcgttcggct gcggcgagcg gtatcagctc actcaaaggc ggtaatacgg ttatccacag   6000
aatcagggga taacgcagga aagaacatgt gagcaaaagg ccagcaaaag gccaggaacc   6060
gtaaaaaggc cgcgttgctg gcgtttttcc ataggctccg ccccctgac gagcatcaca   6120 aaaatcgacg ctcaagtcag aggtggcgaa acccgacagg actataaaga taccaggcgt   6180
ttccccctgg aagctccctc gtgcgctctc ctgttccgac cctgccgctt accggatacc   6240
tgtccgcctt tctcccttcg ggaagcgtgg cgctttctca tagctcacgc tgtaggtatc   6300
tcagttcggt gtaggtcgtt cgctccaagc tgggctgtgt gcacgaaccc cccgttcagc   6360
ccgaccgctg cgccttatcc ggtaactatc gtcttgagtc caacccggta agacacgact   6420
tatcgccact ggcagcagcc actggtaaca ggattagcag agcgaggtat gtaggcggtg   6480
ctacagagtt cttgaagtgg tggcctaact acggctacac tagaagaaca gtatttggta   6540
tctgcgctct gctgaagcca gttaccttcg gaaaagagt tggtagctct tgatccgaca   6600
aacaaaccac cgctggtagc ggtggttttt ttgtttgcaa gcagcagatt acgcgcagaa   6660
aaaaaggatc tcaagaagat cctttgatct tttctacggg gtctgacgct cagtggaacg   6720
aaaactcacg ttaagggatt ttggtcatga gattatcaaa aaggatcttc acctagatcc   6780
ttttaaatta aaaatgaagt tttaaatcaa tctaaagtat atatgagtaa acttggtctg   6840
acagttaagc aaggattttc ttaacttctt cggcgacagc atcaccgact cggtggtac   6900 tgttggaacc acctaaatca ccagttctga tacctgcatc caaaacccttt ttaactgcat   6960 cttcaatggc cttaccttct tcaggcaagt tcaatgacaa tttcaacatc attgcagcag   7020
acaagatagt ggcgataggg ttgaccttat tctttggcaa atctggagca gaaccgtggc   7080
atggttcgta caaaccaaat gcggtgttct tgtctggcaa agaggccaag gacgcagatg   7140
gcaacaaacc caaggaacct gggataacgg aggcttcatc ggagatgata tcaccaaaca   7200
tgttgctggt gattataata ccatttaggt gggttgggtt cttaactagg atcatggcgg   7260
cagaatcaat caattgatgt tgaaccttca atgtagggaa ttcgttcttg atggtttcct   7320
ccacagtttt tctccataat cttgaagagg ccaaaacatt agctttatcc aaggaccaaa   7380
taggcaatgg tggctcatgt tgtagggcca tgaaagcggc cattcttgtg attctttgca   7440
cttctggaac ggtgtattgt tcactatccc aagcgacacc atcaccatcg tcttcctttc   7500
tcttaccaaa gtaaatacct cccactaatt ctctgacaac aacgaagtca gtacctttag   7560
caaattgtgg cttgattgga gataagtcta aaagagagtc ggatgcaaag ttacatggtc   7620
ttaagttggc gtacaattga agttcttac ggattttag taaaccttgt tcaggtctaa   7680
cactgccggt accccattta ggaccaccca cagcacctaa caaaacggca tcagccttct   7740
tggaggcttc cagcgcctca tctggaagtg gaacacctgt agcatcgata gcagcaccac   7800
caattaaatg attttcgaaa tcgaacttga cattggaacg aacatcagaa atagctttaa   7860
```

-continued

```
gaaccttaat ggcttcggct gtgatttctt gaccaacgtg gtcacctggc aaaacgacga      7920
tcttcttagg ggcagacata ctcttccttt ttcaatatta ttgaagcatt tatcagggtt      7980
attgtctcat gagcggatac atatttgaa                                        8009
```

<210> SEQ ID NO 24
<211> LENGTH: 7909
<212> TYPE: DNA
<213> ORGANISM: Artificial Sequence
<220> FEATURE:
<223> OTHER INFORMATION: complet DNA sequence of plasmid pMT3330

<400> SEQUENCE: 24

```
tgtataagct agcttatggt gttttgatca ttttaaattt ttatatggcg ggtggtgggc        60
aactcgcttg cgcgggcaac tcgcttaccg attacgttag ggctgatatt tacgtaaaaa       120
tcgtcaaggg atgcaagacc aaaccgttaa atttccggag tcaacagcat ccaagcccaa       180
gtccttcacg gagaaacccc agcgtccaca tcacgagcga aggaccacct ctaggcatcg       240
gacgcaccat ccaattagaa gcagcaaagc gaaacagccc aagaaaaagg tcggcccgtc       300
ggccttttct gcaacgctga tcacgggcag cgatccaacc aacaccctcc agagtgacta       360
ggggcggaaa tttatcggga ttaatttcca ctcaaccaca aatcacagtc gtccccggta       420
atttaacggc tgcagacggc aatttaacgg cttctgcgaa tcgcttggat tccccgcccc       480
tggccgtaga gcttaaagta tgtcccttgt cgatgcgatg tatgaattca tggtgttttg       540
atcattttaa attttatat ggcgggtggt gggcaactcg cttgcgcggg caactcgctt       600
accgattacg ttagggctga tatttacgta aaaatcgtca agggatgcaa gaccaaaccg       660
ttaaatttcc ggagtcaaca gcatccaagc ccaagtcctt cacggagaaa ccccagcgtc       720
cacatcacga gcgaaggacc acctctaggc atcggacgca ccatccaatt agaagcagca       780
aagcgaaaca gcccaagaaa aaggtcggcc cgtcggcctt ttctgcaacg ctgatcacgg       840
gcagcgatcc aaccaacacc ctccagagtg actaggggcg gaaatttatc gggattaatt       900
tccactcaac cacaaatcac agtcgtcccc ggtaatttaa cggctgcaga cggcaattta       960
acggcttctg cgaatcgctt ggattccccg cccctggccg tagagcttaa agtatgtccc      1020
ttgtcgatgc gatgtatcac aacatataaa tactggcaag ggatgccatg cttgagtttt      1080
ccaactcaat ttacctctat ccacacttct cttccttcct caatcctcta tatacacaac      1140
tggggatccg tcgaccttgg ggaagtcatc accgaatcta attacgatgt cctgggagct      1200
caatatatgg tgaagcagtg ccggaagtcg gtgaacttcc ttggtgctct tgaggccacc      1260
agatatgcga aattgatgac tgataagact gtctggctgg aagttggtgc ccataccatt      1320
tgctctggta tgatcaaagc aacattcggt ccccaggtta ccactgtggc atctcttcgc      1380
cgagaggaga atgcatggaa ggtcctctcc aatagtctat cggcccttca tttggctggc      1440
attgatatta ttggaaaga atatcatcaa gacttcagct ccagccacca ggtgctccca      1500
cttccttctt acaagtggga tctcaagaac tactggatac cctacactaa caatttctgc      1560
cttacgaagg gtgctcccca aactgcaatt caagctgcac cacaaactac attcctgacc      1620
actgctgcgc aaaaggttgt tgagagtcgc gacgagaatt caatgattaa tgacctttc      1680 ctaaatatac taatactgca cgaccatgct ttcttatcta tttcgggggt tactactgaa      1740
atgcaatgag tgactagtag ccagtgacat gtacatgaag tatccttcct acggtctata      1800
ggcaaccatt gagatccggt gtctcagacc catatccatag accgttcatt ggaccatgtt      1860
atctttgaaa gaatacctaa ggaaaccacc tcggcagata atcacccaag ccccaatagt      1920
```

```
tctcgcgacc catgggatgt ccggcacact tccgtatctc atgcacctcc acaccctcgg   1980
ggagattatc aggatcgtaa tacatgactc caagacgtcc gcaaagttct tcgctagccc   2040
ccgggaccgg gaccagagca gcccgggcga ctgcggcaga tccgacgatc agtagaaggt   2100
tgagggagag cctaggctcg agatctagag ggtgactgac acctggcggt agacaatcaa   2160
tccatttcgc tatagttaaa ggatggggat gagggcaatt ggttatatga tcatgtatgt   2220
agtgggtgtg cataatagta gtgaaatgga agccaagtca tgtgattgta atcgaccgac   2280
ggaattgagg atatccggaa atacagacac cgtgaaagcc atggtctttc cttcgtgtag   2340
aagaccagac agacagtccc tgatttaccc ttgcacaaag cactagaaaa ttagcattcc   2400
atccttctct gcttgctctg ctgatatcac tgtcattcaa tgcatagcca tgagctcatc   2460
ttagatccaa gcacgtaatt ccatagccga ggtccacagt ggagcagcaa cattccccat   2520
cattgctttc cccaggggcc tcccaacgac taaatcaaga gtatatctct accgtccaat   2580
agatcgtctt cgcttcaaaa tctttgacaa ttccaagagg gtccccatcc atcaaaccca   2640
gttcaataat agccgagatg catggtggag tcaattaggc agtattgctg gaatgtcggg   2700
gccagttggc cgggtggtca ttggccgcct gtgatgccat ctgccactaa atccgatcat   2760
tgatccaccg cccacgaggc gcgtctttgc tttttgcgcg gcgtccaggt tcaactctct   2820
cctctagact ggaaacgcaa ccctgaaggg attcttcctt tgagagatgg aagcgtgtca   2880
tatctcttcg gttctacggc aggttttttt ctgctctttc gtagcatggc atggtcactt   2940
cagcgcttat ttacagttgc tggtattgat ttcttgtgca aattgctatc tgacacttat   3000
tagctatgga gtcaccacat ttcccagcaa cttccccact tcctctgcaa tcgccaacgt   3060
cctctcttca ctgagtctcc gtccgataac ctgcactgca accggtgccc catggtacgc   3120
ctccggatca tactcttcct gcacgagggc atcaagctca ctaaccgcct tgaaactctc   3180
attcttctta tcgatgttct tatccgcaaa ggtaaccgga acaaccacgc tcgtgaaatc   3240
cagcaggttg atcacagagg catacccata gtaccggaac tggtcatgcc gtaccgcagc   3300
ggtaggcgta atcggcgcga tgatggcgtc cagttccttc ccggcctttt cttcagcctc   3360
ccgccatttc tcaaggtact ccatctggta attccacttc tggagatgcg tgtcccagag   3420
ctcgttcatg ttaacagctt tgatgttcgg gttcagtagg tctttgatat ttggaatcgc   3480
cggctcgccg gatgcactga tatcgcgcat tacgtcggcg ctgccgtcag ccgcgtagat   3540
atgggagatg agatcgtggc cgaaatcgtg cttgtatggc gtccacgggg tcacggtgtg   3600
accggctttg gcgagtgcgg cgacggtggt ttccacgccg cgcaggatag gagggtgtgg   3660
aaggacattg ccgtcgaagt tgtagtagcc gatattgagc ccgccgttct tgatcttgga   3720
ggcaataatg tccgactcgg actggcgcca gggcatgggg atgaccttgg agtcgtattt   3780
ccatggctcc tgaccgagga cggatttggt gaagaggcgg aggtctaaca tacttcatca   3840
gtgactgccg gtctcgtata tagtataaaa agcaagaaag gaggacagtg gaggcctggt   3900
atagagcagg aaaagaagga agaggcgaag gactcaccct caacagagtg cgtaatcggc   3960
ccgacaacgc tgtgcaccgt ctcctgaccc tccatgctgt tcgccatctt tgcatacggc   4020
agccgcccat gactcggcct tagaccgtac aggaagttga acgcggcggc cactcgaatc   4080
gagccaccga tatccgttcc tacaccgatg acgccaccac gaatcccaac gatcgcaccc   4140
tcaccaccag aactgccgcc gcacgaccag ttcttgttgc gtgggttgac ggtgcgcccg   4200
atgatgttgt tgactgtctc gcagaccatc agggtctgcg ggacagaggt cttgacgtag   4260
aagacggcac cggctttgcg gagcatggtt gtcagaaccg agtcccttc gtcgtacttg    4320
```

```
tttagccatg agatgtagcc cattgatgtt tcgtagccct ggtggcatat gttagctgac   4380
aaaaagggac atctaacgac ttaggggcaa cggtgtacct tgactcgaag ctggtctttg   4440
agagagatgg ggaggccatg gagtggacca acgggtctct tgtgctttgc gtagtattca   4500
tcgagttccc ttgcctgcgc gagagcggcg tcagggaaga actcgtgggc gcagtttgtc   4560
tgcacagaag ccagcgtcag cttgatagtc ccataaggtg gcgttgttac atctccctga   4620
gaggtagagg ggaccctact aactgctggg cgattgctgc ccgtttacag aatgctagcg   4680
taacttccac cgaggtcaac tctccggccc ccagcttgga cacaagatct gcagcggagg   4740
cctctgtgat cttcagttcg gcctctgaaa ggatcaccga tttctttggg aaatcaataa   4800
cgctgtcttc cgcaggcagc gtctggactt tccattcatc agggatggtt tttgcgaggc   4860
gggcgcgctt atcagcggcc agttcttccc aggattgagg cattctgtgt tagcttatag   4920
tcaggatgtt ggctcgacga gtgtaaactg ggagttggca tgagggttat gtaggcttct   4980
ttagccccgc atccccctca ttctcctcat tgatcccggg ggagcggatg gtgttgataa   5040
gagactaatt atagggttta gctggtgcct agctggtgat tggctggctt cgccgaattt   5100
tacgggccaa ggaaagctgc agaaccgcgc cactggtaaa cggtaattaa gctatcagcc   5160
ccatgctaac gagtttaaat tacgtgtatt gctgataaac accaacagag ctttactgaa   5220
agatgggagt cacggtgtgg cttccccact gcgattattg cacaagcagc gagggcgaac   5280
ttgactgtcg tcgctgagca gcctgcagtc aaacatacat atatatcaac cgcgaagacg   5340
tctggccttg tagaacacga cgctcccctag caacacctgc cgtgtcagcc tctacggttg   5400
ttacttgcat tcaggatgct ctccagcggg cgagctattc aaaatattca aagcaggtat   5460
ctcgtattgc caggattcag ctgaagcaac aggtgccaag gaaatctgcg tcggttctca   5520
tctgggcttg ctcggtcctg gcgtagatct agagtcgacc tgcaggcatg cggcgtaatc   5580
atggtcatag ctgtttcctg tgtgaaattg ttatccgctc acaattccac acaacatacg   5640
agccggaagc ataaagtgta aagcctgggg tgcctaatga gtgagctaac tcacattaat   5700
tgcgttgcgc tcactgcccg ctttccagtc gggaaacctg tcgtgccagc tgcattaatg   5760
aatcggccaa cgcgcgggga gaggcggttt gcgtattggg cgctcttccg cttcctcgct   5820
cactgactcg ctgcgctcgg tcgttcggct gcggcgagcg gtatcagctc actcaaaggc   5880
ggtaatacgg ttatccacag aatcagggga taacgcagga agaacatgtg agcaaaagg   5940 ccagcaaaag gccaggaacc gtaaaaaggc cgcgttgctg gcgtttttcc ataggctccg   6000 ccccccctgac gagcatcaca aaaatcgacg ctcaagtcag aggtggcgaa acccgacagg   6060
actataaaga taccaggcgt ttccccctgg aagctccctc gtgcgctctc ctgttccgac   6120
cctgccgctt accggatacc tgtccgcctt tctcccttcg ggaagcgtgg cgctttctca   6180
tagctcacgc tgtaggtatc tcagttcggt gtaggtcgtt cgctccaagc tgggctgtgt   6240
gcacgaaccc cccgttcagc ccgaccgctg cgccttatcc ggtaactatc gtcttgagtc   6300
caacccggta agacacgact tatcgccact ggcagcagcc actggtaaca ggattagcag   6360
agcgaggtat gtaggcggtg ctacagagtt cttgaagtgg tggcctaact acggctacac   6420
tagaagaaca gtatttggta tctgcgctct gctgaagcca gttaccttcg gaaaagagt   6480 tggtagctct tgatccgaca acaaaccacc gctggtagc ggtggttttt ttgtttgcaa   6540
gcagcagatt acgcgcagaa aaaaaggatc tcaagaagat cctttgatct tttctacggg   6600
gtctgacgct cagtggaacg aaaactcacg ttaagggatt ttggtcatga gattatcaaa   6660
aaggatcttc acctagatcc ttttaaatta aaaatgaagt tttaaatcaa tctaaagtat   6720
```

```
atatgagtaa acttggtctg acagttaagc aaggattttc ttaacttctt cggcgacagc   6780
atcaccgact tcggtggtac tgttggaacc acctaaatca ccagttctga tacctgcatc   6840
caaaaccttt ttaactgcat cttcaatggc cttaccttct tcaggcaagt tcaatgacaa   6900
tttcaacatc attgcagcag acaagatagt ggcgataggg ttgaccttat tctttggcaa   6960
atctggagca gaaccgtggc atggttcgta caaaccaaat gcggtgttct tgtctggcaa   7020
agaggccaag gacgcagatg gcaacaaacc caaggaacct gggataacgg aggcttcatc   7080
ggagatgata tcaccaaaca tgttgctggt gattataata ccatttaggt ggggttgggtt   7140 cttaactagg atcatggcgg cagaatcaat caattgatgt tgaaccttca atgtagggaa   7200
ttcgttcttg atggtttcct ccacagtttt tctccataat cttgaagagg ccaaaacatt   7260
agctttatcc aaggaccaaa taggcaatgg tggctcatgt tgtagggcca tgaaagcggc   7320
cattcttgtg attctttgca cttctggaac ggtgtattgt tcactatccc aagcgacacc   7380
atcaccatcg tcttcctttc tcttaccaaa gtaaatacct cccactaatt ctctgacaac   7440
aacgaagtca gtacctttag caaattgtgg cttgattgga gataagtcta aagagagtc    7500 ggatgcaaag ttcatggtc ttaagttggc gtacaattga agttctttac ggattttttag   7560 taaaccttgt tcaggtctaa cactgccggt accccattta ggaccaccca cagcacctaa   7620
caaaacggca tcagccttct tggaggcttc cagcgcctca tctggaagtg aacacctgt    7680 agcatcgata gcagcaccac caattaaatg attttcgaaa tcgaacttga cattggaacg   7740
aacatcagaa atagctttaa gaaccttaat ggcttcggct gtgatttctt gaccaacgtg   7800
gtcacctggc aaaacgacga tcttcttagg ggcagacata ctcttccttt tcaatatta    7860 ttgaagcatt tatcagggtt attgtctcat gagcggatac atatttgaa               7909

<210> SEQ ID NO 25
<211> LENGTH: 8964
<212> TYPE: DNA
<213> ORGANISM: Artificial Sequence
<220> FEATURE:
<223> OTHER INFORMATION: complete DNA sequence of plasmid pMT3332

<400> SEQUENCE: 25
tgtataagct agcttatggt gttttgatca ttttaaattt ttatatggcg ggtggtgggc     60
aactcgcttg cgcgggcaac tcgcttaccg attacgttag ggctgatatt tacgtaaaaa   120
tcgtcaaggg atgcaagacc aaaccgttaa atttccggag tcaacagcat ccaagcccaa   180
gtccttcacg gagaaacccc agcgtccaca tcacgagcga aggaccacct ctaggcatcg   240
gacgcaccat ccaattagaa gcagcaaagc gaaacagccc aagaaaaagg tcggcccgtc   300
ggccttttct gcaacgctga tcacgggcag cgatccaacc aacaccctcc agagtgacta   360
ggggcggaaa tttatcggga ttaatttcca ctcaaccaca aatcacagtc gtccccggta   420
atttaacggc tgcagacggc aatttaacgg cttctgcgaa tcgcttggat tccccgcccc   480
tggccgtaga gcttaaagta tgtcccttgt cgatgcgatg tatgaattca tggtgttttg   540
atcattttaa attttatat ggcgggtggt gggcaactcg cttgcgcggg caactcgctt   600
accgattacg ttagggctga tatttacgta aaaatcgtca agggatgcaa gaccaaaccg   660
ttaaatttcc ggagtcaaca gcatccaagc ccaagtcctt cacggagaaa ccccagcgtc   720
cacatcacga gcgaaggacc acctctaggc atcggacgca ccatccaatt agaagcagca   780
aagcgaaaca gcccaagaaa aaggtcggcc cgtcggcctt ttctgcaacg ctgatcacgg   840
gcagcgatcc aaccaacacc ctccagagtg actaggggcg gaaatttatc gggattaatt   900
```

```
tccactcaac cacaaatcac agtcgtcccc ggtaatttaa cggctgcaga cggcaattta   960
acggcttctg cgaatcgctt ggattccccg cccctggccg tagagcttaa agtatgtccc  1020
ttgtcgatgc gatgtatcac aacatataaa tactggcaag ggatgccatg cttggagttt  1080
ccaactcaat ttacctctat ccacacttct cttccttcct caatcctcta tatacacaac  1140
tggggatccg tcgaccttgg ggaagtcatc accgaatcta attacgatgt cctgggagct  1200
caatatatgg tgaagcagtg ccggaagtcg gtgaacttcc ttggtgctct tgaggccacc  1260
agatatgcga aattgatgac tgataagact gtctggctgg aagttggtgc ccataccatt  1320
tgctctggta tgatcaaagc aacattcggt ccccaggtta ccactgtggc atctcttcgc  1380
cgagaggaga atgcatggaa ggtcctctcc aatagtctat cggcccttca tttggctggc  1440
attgatatta attggaaaga atatcatcaa gacttcagct ccagccacca ggtgctccca  1500
cttccttctt acaagtggga tctcaagaac tactggatac cctacactaa caatttctgc  1560
cttacgaagg gtgctcccca aactgcaatt caagctgcac cacaaactac attcctgacc  1620
actgctgcgc aaaaggttgt tgagagtcgc gacgagaatt caatgattaa tgacctttcc  1680
ctaaatatac taatactgca cgaccatgct ttcttatcta tttcgggggt tactactgaa  1740
atgcaatgag tgactagtag ccagtgacat gtacatgaag tatccttcct acggtctata  1800
ggcaaccatt gagatccggt gtctcagacc catatcatag accgttcatt ggaccatgtt  1860
atctttgaaa gaatacctaa ggaaaccacc tcggcagata atcacccaag ccccaatagt  1920
tctcgcgacc catgggatgt ccggcacact tccgtatctc atgcacctcc acaccctcgg  1980
ggagattatc aggatcgtaa tacatgactc caagacgtcc gcaaagttct tcgctagccc  2040
ccgggaccgg gaccagagca gcccgggcga ctgcggcaga tccgacgatc agtagaaggt  2100
tgagggagag tctcatggtg ggatatggtc ttcctctatt agaggtgagg ttaatatttt  2160
gcaggtagag tggataggac gtcggacctg acgtacttga cttttgggata cctaggctct  2220 ccctcaacct tctactgatc gtcggatctg ccgcagtcgc ccgggctgct ctggtcccgg  2280
tcccgggggc tagcgaagaa cttttgcggac gtcttggagt catgtattac gatcctgata  2340
atctccccga gggtgtggag gtgcatgaga tacggaagtg tgccggacat cccatgggtc  2400
gcgagaacta ttgggggcttg ggtgattatc tgccgaggtg gtttccttag gtattctttc  2460
aaagataaca tggtccaatg aacggtctat gatatgggtc tgagacaccg gatctcaatg  2520
gttgcctata gaccgtagga aggatacttc atgtacatgt cactggctac tagtcactca  2580
ttgcatttca gtagtaaccc ccgaaataga taagaaagca tggtcgtgca gtattagtat  2640
atttaggaaa aggtcattaa tcattgaatt ctcgtcgcga ctctcaacaa ccttttgcgc  2700
agcagtggtc aggaatgtag tttgtggtgc agcttgaatt gcagtttggg gagcacccctt  2760 cgtaaggcag aaattgttag tgtagggtat ccagtagttc ttgagatccc acttgtaaga  2820
aggaagtggg agcacctggt ggctggagct gaagtcttga tgatattctt tccaattaat  2880
atcaatgcca gccaaatgaa gggccgatag actattggag aggaccttcc atgcattctc  2940
ctctcggcga agagatgcca cagtggtaac ctggggaccg aatgttgctt tgatcatacc  3000
agagcaaatg gtatgggcac caacttccag ccagacagtc ttatcagtca tcaatttcgc  3060
atatctggtg gcctcaagag caccaaggaa gttcaccgac ttccggcact gcttcaccat  3120
atattgagct cccaggacat cgtaattaga ttcggtgatg acttccccaa ggtcgagatc  3180
tagagggtga ctgacacctg gcggtagaca atcaatccat ttcgctatag ttaaaggatg  3240
gggatgaggg caattggtta tatgatcatg tatgtagtgg gtgtgcataa tagtagtgaa  3300
```

```
atggaagcca agtcatgtga ttgtaatcga ccgacggaat tgaggatatc cggaaataca      3360
gacaccgtga aagccatggt cttttccttcg tgtagaagac cagacagaca gtccctgatt    3420 taccctttgca caaagcacta gaaaattagc attccatcct tctctgcttg ctctgctgat    3480
atcactgtca ttcaatgcat agccatgagc tcatcttaga tccaagcacg taattccata    3540
gccgaggtcc acagtggagc agcaacattc cccatcattg ctttccccag ggcctccca     3600 acgactaaat caagagtata tctctaccgt ccaatagatc gtcttcgctt caaaatcttt    3660
gacaattcca agagggtccc catccatcaa acccagttca ataatagccg agatgcatgg    3720
tggagtcaat taggcagtat tgctggaatg tcggggccag ttggccgggt ggtcattggc    3780
cgcctgtgat gccatctgcc actaaatccg atcattgatc caccgcccac gaggcgcgtc    3840
tttgcttttt gcgcggcgtc caggttcaac tctctcctct agactggaaa cgcaaccctg    3900
aagggattct tcctttgaga gatggaagcg tgtcatatct cttcggttct acggcaggtt    3960
tttttctgct ctttcgtagc atggcatggt cacttcagcg cttatttaca gttgctggta    4020
ttgatttctt gtgcaaattg ctatctgaca cttattagct atggagtcac cacatttccc    4080
agcaacttcc ccacttcctc tgcaatcgcc aacgtcctct cttcactgag tctccgtccg    4140
ataacctgca ctgcaaccgg tgccccatgg tacgcctccg gatcatactc ttcctgcacg    4200
agggcatcaa gctcactaac cgccttgaaa ctctcattct tcttatcgat gttcttatcc    4260
gcaaaggtaa ccggaacaac cacgctcgtg aaatccagca ggttgatcac agaggcatac    4320
ccatagtacc ggaactggtc atgccgtacc gcagcggtag gcgtaatcgg cgcgatgatg    4380
gcgtccagtt ccttcccggc cttttcttca gcctcccgcc atttctcaag gtactccatc    4440
tggtaattcc acttctggag atgcgtgtcc cagagctcgt tcatgttaac agctttgatg    4500
ttcgggttca gtaggtcttt gatatttgga atcgccggct cgccggatgc actgatatcg    4560
cgcattacgt cggcgctgcc gtcagccgcg tagatatggg agatgagatc gtggccgaaa    4620
tcgtgcttgt atggcgtcca cggggtcacg gtgtgaccgg ctttggcgag tgcggcgacg    4680
gtggtttcca cgccgcgcag gataggaggg tgtggaagga cattgccgtc gaagttgtag    4740
tagccgatat tgagcccgcc gttcttgatc ttggaggcaa taatgtccga ctcggactgg    4800
cgccagggca tggggatgac cttggagtcg tatttccatg gctcctgacc gaggacggat    4860
ttggtgaaga ggcggaggtc taacatactt catcagtgac tgccggtctc gtatatagta    4920 taaaagcaa gaaaggagga cagtggaggc ctggtataga gcaggaaaag aaggaagagg     4980
cgaaggactc accctcaaca gagtgcgtaa tcggcccgac aacgctgtgc accgtctcct    5040
gaccctccat gctgttcgcc atcttttgcat acggcagccg cccatgactc ggccttagac    5100
cgtacaggaa gttgaacgcg gccggcactc gaatcgagcc accgatatcc gttcctacac    5160
cgatgacgcc accacgaatc ccaacgatcg caccctcacc accagaactg ccgccgcacg    5220
accagttctt gttgcgtggg ttgacggtgc gcccgatgat gttgttgact gtctcgcaga    5280
ccatcagggt ctgcgggaca gaggtcttga cgtagaagac ggcaccggct ttgcggagca    5340
tggttgtcag aaccgagtcc ccttcgtcgt acttgtttag ccatgagatg tagcccattg    5400
atgtttcgta gccctggtgg catatgttag ctgacaaaaa gggacatcta acgacttagg    5460
ggcaacggtg taccttgact cgaagctggt ctttgagaga gatggggagg ccatggagtg    5520
gaccaacggg tctcttgtgc tttgcgtagt attcatcgag ttcccttgcc tgcgcgagag    5580
cggcgtcagg gaagaactcg tgggcgcagt ttgtctgcac agaagccagc gtcagcttga    5640
tagtcccata aggtggcgtt gttacatctc cctgagaggt agagggggacc ctactaactg   5700
```

```
ctgggcgatt gctgcccgtt tacagaatgc tagcgtaact tccaccgagg tcaactctcc    5760
ggccgccagc ttggacacaa gatctgcagc ggaggcctct gtgatcttca gttcggcctc    5820
tgaaaggatc accgatttct ttgggaaatc aataacgctg tcttccgcag gcagcgtctg    5880
gactttccat tcatcaggga tggttttgc gaggcgggcg cgcttatcag cggccagttc    5940
ttcccaggat tgaggcattc tgtgttagct tatagtcagg atgttggctc gacgagtgta    6000
aactgggagt tggcatgagg gttatgtagg cttctttagc cccgcatccc cctcattctc    6060
ctcattgatc ccgggggagc ggatggtgtt gataagagac taattatagg gtttagctgg    6120
tgcctagctg gtgattggct ggcttcgccg aattttacgg gccaaggaaa gctgcagaac    6180
cgcggcactg gtaaacggta attaagctat cagccccatg ctaacgagtt taaattacgt    6240
gtattgctga taaacaccaa cagagcttta ctgaaagatg ggagtcacgg tgtggcttcc    6300
ccactgcgat tattgcacaa gcagcgaggg cgaacttgac tgtcgtcgct gagcagcctg    6360
cagtcaaaca tacatatata tcaaccgcga agacgtctgg ccttgtagaa cacgacgctc    6420
cctagcaaca cctgccgtgt cagcctctac ggttgttact tgcattcagg atgctctcca    6480
gcgggcgagc tattcaaaat attcaaagca ggtatctcgt attgccagga ttcagctgaa    6540
gcaacaggtg ccaaggaaat ctgcgtcggt tctcatctgg gcttgctcgg tcctggcgta    6600
gatctagagt cgacctgcag gcatgcggcg taatcatggt catagctgtt tcctgtgtga    6660
aattgttatc cgctcacaat tccacacaac atacgagccg aagcataaa gtgtaaagcc    6720 tggggtgcct aatgagtgag ctaactcaca ttaattgcgt tgcgctcact gcccgctttc    6780
cagtcgggaa acctgtcgtg ccagctgcat taatgaatcg gccaacgcgc ggggagaggc    6840
ggtttgcgta ttgggcgctc ttccgcttcc tcgctcactg actcgctgcg ctcggtcgtt    6900
cggctgcggc gagcggtatc agctcactca aaggcggtaa tacggttatc cacagaatca    6960
ggggataacg caggaaagaa catgtgagca aaaggccagc aaaaggccag gaaccgtaaa    7020
aaggccgcgt tgctggcgtt tttccatagg ctccgccccc ctgacgagca tcacaaaaat    7080
cgacgctcaa gtcagaggtg gcgaaacccg acaggactat aaagatacca ggcgtttccc    7140
cctggaagct ccctcgtgcg ctctcctgtt ccgaccctgc cgcttaccgg atacctgtcc    7200
gcctttctcc cttcgggaag cgtggcgctt tctcatagct cacgctgtag gtatctcagt    7260
tcggtgtagg tcgttcgctc caagctgggc tgtgtgcacg aaccccccgt tcagcccgac    7320
cgctgcgcct tatccggtaa ctatcgtctt gagtccaacc cggtaagaca cgacttatcg    7380
ccactggcag cagccactgg taacaggatt agcagagcga ggtatgtagg cggtgctaca    7440
gagttcttga agtggtggcc taactacggc tacactagaa gaacagtatt tggtatctgc    7500
gctctgctga agccagttac cttcggaaaa agagttggta gctcttgatc cgacaaacaa    7560
accaccgctg gtagcggtgg tttttttgtt tgcaagcagc agattacgcg cagaaaaaaa    7620
ggatctcaag aagatccttt gatcttttct acggggtctg acgctcagtg gaacgaaaac    7680
tcacgttaag ggattttggt catgagatta tcaaaaagga tcttcaccta gatccttta    7740 aattaaaaat gaagttttaa atcaatctaa agtatatatg agtaaacttg gtctgacagt    7800
taagcaagga tttctcttaac ttcttcggcg acagcatcac cgacttcggt ggtactgttg    7860
gaaccaccta aatcaccagt tctgatacct gcatccaaaa ccttttaac tgcatcttca    7920 atggccttac cttcttcagg caagttcaat gacaatttca acatcattgc agcagacaag    7980
atagtggcga tagggttgac cttattcttt ggcaaatctg gagcagaacc gtggcatggt    8040
tcgtacaaac caaatgcggt gttcttgtct ggcaaagagg ccaaggacgc agatggcaac    8100
```

```
aaacccaagg aacctgggat aacggaggct tcatcggaga tgatatcacc aaacatgttg    8160
ctggtgatta taataccatt taggtgggtt gggttcttaa ctaggatcat ggcggcagaa    8220
tcaatcaatt gatgttgaac cttcaatgta gggaattcgt tcttgatggt ttcctccaca    8280 gttttctcc ataatcttga agaggccaaa acattagctt tatccaagga ccaaataggc    8340
aatggtggct catgttgtag ggccatgaaa gcggccattc ttgtgattct ttgcacttct    8400
ggaacggtgt attgttcact atcccaagcg acaccatcac catcgtcttc ctttctctta    8460
ccaaagtaaa tacctcccac taattctctg acaacaacga agtcagtacc tttagcaaat    8520
tgtggcttga ttggagataa gtctaaaaga gagtcggatg caaagttaca tggtcttaag    8580
ttggcgtaca attgaagttc tttacggatt tttagtaaac cttgttcagg tctaacactg    8640
ccggtacccc atttaggacc acccacagca cctaacaaaa cggcatcagc cttcttggag    8700
gcttccagcg cctcatctgg aagtggaaca cctgtagcat cgatagcagc accaccaatt    8760
aaatgatttt cgaaatcgaa cttgacattg gaacgaacat cagaaatagc tttaagaacc    8820
ttaatggctt cggctgtgat ttcttgacca acgtggtcac ctggcaaaac gacgatcttc    8880
ttaggggcag acatactctt cctttttcaa tattattgaa gcatttatca gggttattgt    8940
ctcatgagcg gatacatatt tgaa                                           8964

<210> SEQ ID NO 26
<211> LENGTH: 6248
<212> TYPE: DNA
<213> ORGANISM: Artificial Sequence
<220> FEATURE:
<223> OTHER INFORMATION: complete DNA sequence of plasmid pMT3369

<400> SEQUENCE: 26
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagctca     240
gaattaaccc tcactaaagg gactagtcct gcaggtttaa acgaattcgc ccttcgatcg     300
acttgaaaac catgtctgac aattggatat acaaccgtag cgtatgtatt tgaactaatg     360
ggattgtgga ctgtgtatag ccaattctat ttcgtatgat ggatcccttt tcatttaatc     420
taactaaggt ggatataact tgaaggctaa cgattgcgtc tcgggtaagg atcaccatca     480
ctatcctacg tgcttaaggc ccaggctggc catcaagcag ctcatagagt tctacagaac     540
tcttggtaca tactgaaaga aattcctaat tggctttggc tatccgggga aattttagcg     600
agcagaaaat atccctacgc tgaggtggac cgctcggtcg atcggtatat tgaccctctt     660
taaatcagcc cccaaatctc cgattatgta tgtcatccca ggactttcta caatcaatct     720
acttcgcgtg tcaatctacc gattgtggag ccatgtcaga gagaaacatg gtatcaaata     780
ttgaatttgg tgcactacac ctagagtcga acctcagcaa agccatcatt gcatgggatg     840
gtcaaatcga cacgcgaaat ccaaggagag aaccgccat gactagcaga gagccctgcg     900
ctcagatgaa tcgcaaagcc cgaggattgg tatcagcgaa agtatcatcc acaattttgt     960
ctaccgactt gacatagata gtcccttccg atgaatatat tccacctctc ccaaccactg    1020
aggctaatat gcagttatca acaatccacg caaaccagct tgcattagac ccttctgctt    1080
ggataacatc cttgtttggc aggatttatc tgataggttc aatatagata ctagacttct    1140
ataattattc ggagtgatcc aaagctgatt cctatcttat cacccatgcc gtccgacgta    1200
```

```
tactgccaaa gattataatc agagatgaaa tgttggaaaa tagagctgag cattctgcat   1260
ctggtcgttg tggtctgtaa ccttggtgag gccccgtcta aaggaacgga tgctacacaa   1320
aactatggtt tgttagcatc caatatgtcg catctcttcc cactactttg attcaaacca   1380
tggtacttgg ccgcatgacg taaaatagac ccgctctgga tcaagattag tctaaagctt   1440
gtgatagggg gttaccactc attgcatttc agtagtaacc cccgaaatag ataagaaagc   1500
atggtcgtgc agtattagta tatttaggaa aaggtcatta atcattacca acacacttgc   1560
gttgagtcat cttactcaac cggcctcctt ccccacacaa catgaaactt cccatagata   1620
tgcaccctag gatctctcaa ctcattccgc acagaggcca agaaaactgc tacctccacc   1680
ggggaccagc cgagaaccct tgtacaaagc gcaagagcat acgactcaag actcataacc   1740
atgacttcgc gatggaaccg accggcttct tttaatcgct tttctttagc ccagggaccc   1800
atcgggaact acagaaatta agttaatacc cgatagatta acggagtatt aaaccagagg   1860
gagagcgaaa gtagaaaaaa cctaccttgt agatcttttc cttcacatcg gtgaaccctg   1920
cgtctatcat atttctctga tggtcggccg ccaccttcat tggccggtta aacctcgagc   1980
ttgcctcaat caacagtctg aaccactcgc ccagtgaggg cgccagatcg agtgtgtcat   2040
cgtcagagaa atgttccatc tcaaagtcgg atagttccaa ccatccacct ggcttcatgt   2100
gtgaatatgc ctggcgcagc agtttcggcc agtcggcgat cgaaccggca aggtcgcatg   2160
cacggatgaa gtcgaagtaa tctcgtttga aagtccagtc ggcttcgacg tcgtcgacga   2220
agaattcgag gttcggaggg acccaggcgg gttggatggg gctgagatcg gtgccgatta   2280
ctcgggcgtt ggggtgtgtg tctgcgaagt cgatggccca gatacccttta ttattatttg   2340 gtcagccatg agcgagcggg tttcctggaa tagatacggc atgtgccata cctgttccgg   2400
tgccaatgtc gaaaacgttc tcaacatcct ctgggatcgg ggcgtgaaag agatctccac   2460
tgaaatgcag attgcgaacg tggtgtaata ggtcctcgcg atcttgctct tgttcgtcgt   2520
ttggcagcac acactgccct tcgcggtagg agtggtatcg acggccattc tcgtacttgt   2580
agtttcaagg gcgaattcgc ggccgctaaa ttcaattcgc cctatagtga gtcgtattac   2640
aattcactgg ccgtcgtttt acaacgtcgt gactgggaaa accctggcgt tacccaactt   2700
aatcgccttg cagcacatcc cccttcgcc agctggcgta atagcgaaga ggcccgcacc   2760
gatcgccctt cccaacagtt gcgcagccta tacgtacggc agtttaaggt ttacacctat   2820
aaaagagaga gccgttatcg tctgtttgtg gatgtacaga gtgatattat tgacacgccg   2880
gggcgacgga tggtgatccc cctggccagt gcacgtctgc tgtcagataa agtctcccgt   2940
gaactttacc cggtggtgca tatcggggat gaaagctggc gcatgatgac caccgatatg   3000
gccagtgtgc cggtctccgt tatcggggaa gaagtggctg atctcagcca ccgcgaaaat   3060
gacatcaaaa acgccattaa cctgatgttc tggggaatat aaatgtcagg catgagatta   3120
tcaaaaagga tcttcaccta gatccttttc acgtagaaag ccagtccgca gaaacggtgc   3180
tgaccccgga tgaatgtcag ctactgggct atctggacaa gggaaaacgc aagcgcaaag   3240
agaaagcagg tagcttgcag tgggcttaca tggcgatagc tagactgggc ggttttatgg   3300
acagcaagcg aaccggaatt gccagctggg gcgccctctg gtaaggttgg gaagccctgc   3360
aaagtaaact ggatggcttt cttgccgcca aggatctgat ggcgcagggg atcaagctct   3420
gatcaagaga caggatgagg atcgtttcgc atgattgaac aagatggatt gcacgcaggt   3480
tctccggccg cttgggtgga gaggctattc ggctatgact gggcacaaca gacaatcggc   3540
tgctctgatg ccgccgtgtt ccggctgtca gcgcaggggc gcccggttct ttttgtcaag   3600
```

```
accgacctgt ccggtgccct gaatgaactg caagacgagg cagcgcggct atcgtggctg    3660
gccacgacgg gcgttccttg cgcagctgtg ctcgacgttg tcactgaagc gggaagggac    3720
tggctgctat tgggcgaagt gccggggcag gatctcctgt catctcacct tgctcctgcc    3780
gagaaagtat ccatcatggc tgatgcaatg cggcggctgc atacgcttga tccggctacc    3840
tgcccattcg accaccaagc gaaacatcgc atcgagcgag cacgtactcg gatggaagcc    3900
ggtcttgtcg atcaggatga tctggacgaa gagcatcagg ggctcgcgcc agccgaactg    3960
ttcgccaggc tcaaggcgag catgcccgac ggcgaggatc tcgtcgtgac ccatggcgat    4020
gcctgcttgc cgaatatcat ggtggaaaat ggccgctttt ctggattcat cgactgtggc    4080
cggctgggtg tggcggaccg ctatcaggac atagcgttgg ctacccgtga tattgctgaa    4140
gagcttggcg gcgaatgggc tgaccgcttc ctcgtgcttt acggtatcgc cgctcccgat    4200
tcgcagcgca tcgccttcta tcgccttctt gacgagttct tctgaattat taacgcttac    4260
aatttcctga tgcggtattt tctccttacg catctgtgcg gtatttcaca ccgcatcagg    4320
tggcactttt cggggaaatg tgcgcggaac ccctatttgt ttatttttct aaatacattc    4380
aaatatgtat ccgctcatga gattatcaaa aaggatcttc acctagatcc ttttaaatta    4440
aaaatgaagt tttaaatcaa tctaaagtat atatgagtaa acttggtctg acagttacca    4500
atgcttaatc agtgaggcac ctatctcagc gatctgtcta tttcgttcat ccatagttgc    4560
ctgactcccc gtcgtgtaga taactacgat acgggagggc ttaccatctg gccccagtgc    4620
tgcaatgata ccgcgagacc cacgctcacc ggctccagat ttatcagcaa taaaccagcc    4680
agccggaagg gccgagcgca gaagtggtcc tgcaacttta tccgcctcca tccagtctat    4740
taattgttgc cgggaagcta gagtaagtag ttcgccagtt aatagtttgc gcaacgttgt    4800
tgccattgct acaggcatcg tggtgtcacg ctcgtcgttt ggtatggctt cattcagctc    4860
cggttcccaa cgatcaaggc gagttacatg atcccccatg ttgtgcaaaa aagcggttag    4920
ctccttcggt cctccgatcg ttgtcagaag taagttggcc gcagtgttat cactcatggt    4980
tatggcagca ctgcataatt ctcttactgt catgccatcc gtaagatgct tttctgtgac    5040
tggtgagtac tcaaccaagt cattctgaga atagtgtatg cggcgaccga gttgctcttg    5100
cccggcgtca atacgggata ataccgcgcc acatagcaga actttaaaag tgctcatcat    5160
tggaaaacgt tcttcggggc gaaaactctc aaggatctta ccgctgttga tccagttc     5220 gatgtaaccc actcgtgcac ccaactgatc ttcagcatct tttactttca ccagcgtttc    5280
tgggtgagca aaaacaggaa ggcaaaatgc cgcaaaaaag gaataagggc gacacggaa     5340 atgttgaata ctcatactct tccttttca atattattga gcatttatc agggttattg      5400 tctcatgacc aaaatccctt aacgtgagtt ttcgttccac tgagcgtcag acccgtaga     5460 aaagatcaaa ggatcttctt gagatccttt ttttctgcgc gtaatctgct gcttgcaaac    5520
aaaaaaacca ccgctaccag cggtggtttg tttgccggat caagagctac caactctttt    5580
tccgaaggta actggcttca gcagagcgca gataccaaat actgttcttc tagtgtagcc    5640
gtagttaggc caccacttca agaactctgt agcaccgcct acatacctcg ctctgctaat    5700
cctgttacca gtggctgctg ccagtggcga taagtcgtgt cttaccgggt tggactcaag    5760
acgatagtta ccggataagg cgcagcggtc gggctgaacg gggggttcgt gcacacagcc    5820
cagcttggag cgaacgacct acaccgaact gagatacta cagcgtgagc tatgagaaag    5880
cgccacgctt cccgaaggga gaaaggcgga caggtatccg gtaagcggca gggtcggaac    5940
aggagagcgc acgagggagc ttccagggg aaacgcctgg tatctttata gtcctgtcgg    6000
```

```
gtttcgccac ctctgacttg agcgtcgatt tttgtgatgc tcgtcagggg ggcggagcct    6060
atggaaaaac gccagcaacg cggccttttt acggttcctg gccttttgct ggccttttgc    6120
tcacatgttc tttcctgcgt tatcccctga ttctgtggat aaccgtatta ccgcctttga    6180
gtgagctgat accgctcgcc gcagccgaac gaccgagcgc agcgagtcag tgagcgagga    6240
agcggaag                                                             6248
```

<210> SEQ ID NO 27
<211> LENGTH: 9787
<212> TYPE: DNA
<213> ORGANISM: Artificial Sequence
<220> FEATURE:
<223> OTHER INFORMATION: complete DNA sequence of plasmid pMT3376

<400> SEQUENCE: 27

```
agcgcccaat acgcaaaccg cctctccccg cgcgttggcc gattcattaa tgcagctggc      60
acgacaggtt tcccgactgg aaagcgggca gtgagcgcaa cgcaattaat gtgagttagc     120
tcactcatta ggcaccccag gctttacact ttatgcttcc ggctcgtatg ttgtgtggaa     180
ttgtgagcgg ataacaattt cacacaggaa acagctatga ccatgattac gccaagctca     240
gaattaaccc tcactaaagg gactagtcct gcaggtttaa acgaattcgc cttcgatcg      300 acttgaaaac catgtctgac aattggatat acaaccgtag cgtatgtatt tgaactaatg     360
ggattgtgga ctgtgtatag ccaattctat ttcgtatgat ggatcccttt tcatttaatc     420
taactaaggt ggatataact tgaaggctaa cgattgcgtc tcgggtaagg atcaccatca     480
ctatcctacg tgcttaaggc ccaggctggc catcaagcag ctcatagagt tctacagaac     540
tcttggtaca tactgaaaga aattcctaat tggctttggc tatccgggga aattttagcg     600
agcagaaaat atccctacgc tgaggtggac cgctcggtcg atcggtatat tgaccctctt     660
taaatcagcc cccaaatctc cgattatgta tgtcatccca ggactttcta caatcaatct     720
acttcgcgtg tcaatctacc gattgtggag ccatgtcaga gagaaacatg gtatcaaata     780
ttgaatttgg tgcactacac ctagagtcgg acctcagcaa agccatcatt gcatgggatg     840
gtcaaatcga cacgcgaaat ccaaggagag aaccgccat gactagcaga gagccctgcg      900
ctcagatgaa tcgcaaagcc cgaggattgg tatcagcgaa agtatcatcc acaattttgt     960
ctaccgactt gacatagata gtcccttccg atgaatatat tccacctctc ccaaccactg    1020
aggctaatat gcagttatca acaatccacg caaaccagct tgcattagac ccttctgctt    1080
ggataacatc cttgtttggc aggatttatc tgataggttc aatatagata ctagacttct    1140
ataattattc ggagtgatcc aaagctgatt cctatcttat cacccatgcc gtccgacgta    1200
tactgccaaa gattataatc agagatgaaa tgttggaaaa tagagctgag cattctgcat    1260
ctggtcgttg tggtctgtaa ccttggtgag gccccgtcta aggaacggga tgctacacaa    1320
aactatggtt tgttagcatc caatatgtcg catctcttcc cactactttg attcaaacca    1380
tggtacttgg ccgcatgacg taaaatagac ccgctctgga tcaagattag tctaaagctt    1440
ctctggtact cttcgatctc tctcctcggt tgcattggca aggaggttgg cgacatctga    1500
tagtacacac caggttagca agactatacc tatgtctacg gaggattcat gactgtgaaa    1560
cttacatcta tctaccggta gactagggtc ccgcaaagca ttgagatcca cttgtggtgg    1620
ccctgaggcc tctgtcgagg gccgtctgct ggtcgactga ggggactta gcgccgtata    1680 ctgagtcgga actttaggca ccccgggcac cgggggcgca tttgcggagt caagatcagg    1740
attgatctgt ggatcctatg gatctcagaa caatatacca gaaaatgcga aggtaagtgc    1800
```

```
ttctatattg atccttagtg ctttcaaact gtgatgtaga agttgctcgg tagctgatta      1860
aatattctag acccaagccg ctgctggaat tgacattatt atggccgata gggttgggct      1920
tattgctatg tccctgaaag gatatcaaaa gcaggcaaaa agccaggcat aatccccgcg      1980
tggacggtac cctaaggata ggccctaatc ttatctacat gtgactgcat cgatgtgttt      2040
ggtcaaaatg aggcatgtgg ctcaccccac aggcggagaa acgtgtggct agtgcatgac      2100
agtcccctcc atagattcaa tttaattttt cgcggcaatt gtcgtgcagt ttgtatctac      2160
atttcattcc atatatcaag agttagtagt tggacatcct gattattttg tctaattact      2220
gaaaactcga agtactaacc tactaataag ccagtttcaa ccactaagtg ctcatttata      2280
caatatttgc agaaccccgc gctacccctc catcgccaac atgtcttcca agtcgcaatt      2340
gacctacagc gcacgcgcta gcaagcaccc caatgcgctc gtaaagaagc tcttcgaggt      2400
tgccgaggcc aagaaaacca atgtcaccgt ttccgccgac gtgacaacca ccaaagagct      2460
gctggatttg gctgaccgta tgcgcaccgg ggatgccact tacatgtgat ctagtaatgg      2520
ttaatggtgg attatataac aggactcggt ccgtacattg ccgtgatcaa aactcacatc      2580
gatatcctct ccgatttcag cgaagaaacc atcaccggtc tgaaggccct tgcagagaag      2640
cacaatttcc tcatcttcga agatcgcaag ttcatcgata tcggaaacac agtccaaaag      2700
cagtaccatg gcggcactct gcgtatctct gagtgggccc acatcatcaa ctgcagtatt      2760
ctgcccggtg agggtatcgt cgaggctctg gcccagactg cttcggccga ggacttcccc      2820
tacggctccg agaggggcct tttgatcctt gcggagatga cctccaaggg atctttggct      2880
accggtcaat atactacttc ttctgttgac tatgctcgga agtataagaa gtttgtgatg      2940
ggattcgtct cgacacgtca ccttggcgag gttcagtctg aagttagctc gccttcggag      3000
gaggaagatt ttgtcgtctt cacgacaggt gtcaacctct cctcgaaggg tgacaagctg      3060
ggacagcagt accaaactcc tgagtcggct gttggacgcg gtgccgactt tattattgct      3120
ggccgtggaa tttatgctgc tcctgatccc gtggaggcgg cgaagcagta ccagaaggag      3180
ggatgggatg catacctgaa gcgtgttggt gcgcaataag tagtggtgga tacgtactcc      3240
ttttatggca gtatgtcgca agtatgatgc gatttataaa ttcagcactc gaaatgacta      3300
ctactatgtg tctacgacag ataccctctc cgtacgaata agacacctgc ctcgatatat      3360
ggacaaattc aaaatcaggg tcaagggtca tgtttcaaag tcacaacaat ctccaacata      3420
gacgagaatt tgtaccggag tgtctgaagg tgcagctgga gattggtcta ttttcttaga      3480
gtggggtatc actaatgtac agtcggtcac tatcgtacaa acaatcacaa ttatatacaa      3540
gatttcccac cacccctac tctaacacgg cacaattatc catcgagtca gagcctagcc       3600
accatttggt gctctcgtag agaccaaagt ataatcctga tccgacagcg gccataaacg      3660
tgttgatagc acaccctcgg aatagtcctc tcgggccatc tgttcgtaca atctcccgta      3720
cggtattgat catccttttc ttctgaggtg cagttgtatc tgcagcatcg agcatgattc      3780
gtgtccggac catatccatg ggtgctgtca agacactagc tataccgccc gagaccgcag      3840
cacttattgc ggctgtcgct gcagcctctc cgattgtcga atgggcctct ttcttttccat     3900 actctcttgg tctttctagc accttctctc gatctccgaa tctatattca aaaattcgat      3960
accgaaaaga ctcgtacaga ggcatctgaa tcgccgacac tggcaagcta tgcgccacaa      4020
gagccgggta tccgctccaa agctgtctag ggttgataaa cttcttgaaa gctagccgtg      4080
tcgctttctg ggctacacca cctacccttc ccccagctac aggtgctgat gcgtctggat      4140
ggtgtgattg gatcatctgc gcgttgtgtt ttaatgcatc agccggagca aagactccgc      4200
```

```
aagcagcaag atccgcaacg gaggctgcgc aaaaatcgga aaagagccga gctgagctag    4260
actcatgcgt tccaagtttt tgatgtatga cttggagtcc tgactgtgca tactcgtatg    4320
tgatgaagaa tgcgcccgct ttgacccgtt attttttgct caatgaatat gagttgggta    4380
aggataatgt tgggtatcac caacctgtgg gaaatgaggc agcggttacg ctcgcgatac    4440
cttggtaaag gccgcggaat atccctgggt gtctccatat gctggttcct gtgttggttc    4500
tcaggaactg cgaatattcg cgagactgaa tgcgggtttt gatcgtatct aagggatatg    4560
tgaatagatc tctctggtac tcttcgatct ctctcctcgg ttgcattggc aaggaggttg    4620
gcgacatctg atagtacaca ccaggttagc aagactatac ctatgtctac ggaggattca    4680
tgactgtgaa acttacatct atctaccggt agactagggt cccgcaaagc attgagatcc    4740
acttgtggtg gccctgaggc ctctgtcgag ggccgtctgc tggtcgactg aggggacttt    4800
agcgccgtat actgagtcgg aactttaggc accccgggca cgggggcgc atttgcggag     4860 tcaagatcag gattgatctg tggatcctat ggatctcaga acaatatacc agaaaatgcg    4920
aaggtaagtg cttctatatt gatccttagt gctttcaaac tgtgatgtag aagaagcttg    4980
tgataggggg ttaccactca ttgcatttca gtagtaaccc ccgaaataga taagaaagca    5040
tggtcgtgca gtattagtat atttaggaaa aggtcattaa tcattaccaa cacacttgcg    5100
ttgagtcatc ttactcaacc ggcctccttc cccacacaac atgaaacttc ccatagatat    5160
gcaccctagg atctctcaac tcattccgca cagaggccaa gaaaactgct acctccaccg    5220
gggaccagcc gagaacccctt gtacaaagcg caagagcata cgactcaaga ctcataacca    5280
tgacttcgcg atggaaccga ccggcttctt ttaatcgctt ttctttagcc cagggaccca    5340
tcgggaacta cagaaaattaa gttaataccc gatagattaa cggagtatta aaccagaggg    5400
agagcgaaag tagaaaaaac ctaccttgta gatcttttcc ttcacatcgg tgaaccctgc    5460
gtctatcata tttctctgat ggtcggccgc caccttcatt ggccggttaa acctcgagct    5520
tgcctcaatc aacagtctga accactcgcc cagtgagggc gccagatcga gtgtgtcatc    5580
gtcagagaaa tgttccatct caaagtcgga tagttccaac catccacctg gcttcatgtg    5640
tgaatatgcc tggcgcagca gtttcggcca gtcggcgatc gaaccggcaa ggtcgcatgc    5700
acggatgaag tcgaagtaat ctcgtttgaa agtccagtcg gcttcgacgt cgtcgacgaa    5760
gaattcgagg ttcggaggga cccaggcggg ttggatgggg ctgagatcgg tgccgattac    5820
tcgggcgttg gggtgtgtgt ctgcgaagtc gatggcccag ataccttttat tattatttgg    5880 tcagccatga gcgagcgggt ttcctggaat agatacggca tgtgccatac ctgttccggt    5940
gccaatgtcg aaaacgttct caacatcctc tgggatcggg gcgtgaaaga gatctccact    6000
gaaatgcaga ttgcgaacgt ggtgtaatag gtcctcgcga tcttgctctt gttcgtcgtt    6060
tggcagcaca cactgccctt cgcggtagga gtggtatcga cggccattct cgtacttgta    6120
gtttcaaggg cgaattcgcg gccgctaaat tcaattcgcc ctatagtgag tcgtattaca    6180
attcactggc cgtcgtttta caacgtcgtg actgggaaaa ccctggcgtt acccaactta    6240
atcgccttgc agcacatccc cctttcgcca gctggcgtaa tagcgaagag gcccgcaccg    6300
atcgcccttc ccaacagttg cgcagcctat acgtacggca gtttaaggtt tacacctata    6360
aaagagagag ccgttatcgt ctgtttgtgg atgtacagag tgatattatt gacacgccgg    6420
ggcgacggat ggtgatcccc ctggccagtg cacgtctgct gtcagataaa gtctcccgtg    6480
aactttaccc ggtggtgcat atcggggatg aaagctggcg catgatgacc accgatatgg    6540
ccagtgtgcc ggtctccgtt atcggggaag aagtggctga tctcagccac cgcgaaaatg    6600
```

```
acatcaaaaa cgccattaac ctgatgttct ggggaatata aatgtcaggc atgagattat    6660 caaaaggat  cttcacctag atccttttca cgtagaaagc cagtccgcag aaacggtgct    6720
gaccccggat gaatgtcagc tactgggcta tctggacaag ggaaaacgca agcgcaaaga    6780
gaaagcaggt agcttgcagt gggcttacat ggcgatagct agactgggcg ttttatgga    6840 cagcaagcga accggaattg ccagctgggg cgccctctgg taaggttggg aagccctgca    6900
aagtaaactg gatggctttc ttgccgccaa ggatctgatg gcgcagggga tcaagctctg    6960
atcaagagac aggatgagga tcgtttcgca tgattgaaca agatggattg cacgcaggtt    7020
ctccggccgc ttgggtggag aggctattcg gctatgactg ggcacaacag acaatcggct    7080
gctctgatgc cgccgtgttc cggctgtcag cgcaggggcg cccggttctt tttgtcaaga    7140
ccgacctgtc cggtgccctg aatgaactgc aagacgaggc agcgcggcta tcgtggctgg    7200
ccacgacggg cgttccttgc gcagctgtgc tcgacgttgt cactgaagcg ggaagggact    7260
ggctgctatt gggcgaagtg ccggggcagg atctcctgtc atctcacctt gctcctgccg    7320
agaaagtatc catcatggct gatgcaatgc ggcggctgca tacgcttgat ccggctacct    7380
gcccattcga ccaccaagcg aaacatcgca tcgagcgagc acgtactcgg atggaagccg    7440
gtcttgtcga tcaggatgat ctggacgaag agcatcaggg gctcgcgcca gccgaactgt    7500
tcgccaggct caaggcgagc atgcccgacg gcgaggatct cgtcgtgacc catggcgatg    7560
cctgcttgcc gaatatcatg gtggaaaatg gccgcttttc tggattcatc gactgtggcc    7620
ggctgggtgt ggcggaccgc tatcaggaca tagcgttggc tacccgtgat attgctgaag    7680
agcttggcgg cgaatgggct gaccgcttcc tcgtgcttta cggtatcgcc gctcccgatt    7740
cgcagcgcat cgccttctat cgccttcttg acgagttctt ctgaattatt aacgcttaca    7800
atttcctgat gcggtatttt ctccttacgc atctgtgcgg tatttcacac cgcatcaggt    7860
ggcacttttc ggggaaatgt gcgcggaacc cctatttgtt tatttttcta aatacattca    7920
aatatgtatc cgctcatgag attatcaaaa aggatcttca cctagatcct tttaaattaa    7980
aaatgaagtt ttaaatcaat ctaaagtata tatgagtaaa cttggtctga cagttaccaa    8040
tgcttaatca gtgaggcacc tatctcagcg atctgtctat ttcgttcatc catagttgcc    8100
tgactccccg tcgtgtagat aactacgata cgggagggct taccatctgg ccccagtgct    8160
gcaatgatac cgcgagaccc acgctcaccg gctccagatt tatcagcaat aaaccagcca    8220
gccggaaggg ccgagcgcag aagtggtcct gcaactttat ccgcctccat ccagtctatt    8280
aattgttgcc gggaagctag agtaagtagt tcgccagtta atagtttgcg caacgttgtt    8340
gccattgcta caggcatcgt ggtgtcacgc tcgtcgtttg gtatggcttc attcagctcc    8400
ggttcccaac gatcaaggcg agttacatga tcccccatgt tgtgcaaaaa agcggttagc    8460
tccttcggtc ctccgatcgt tgtcagaagt aagttggccg cagtgttatc actcatggtt    8520
atggcagcac tgcataattc tcttactgtc atgccatccg taagatgctt ttctgtgact    8580
ggtgagtact caaccaagtc attctgagaa tagtgtatgc ggcgaccgag ttgctcttgc    8640
ccggcgtcaa tacgggataa taccgcgcca catagcagaa ctttaaaagt gctcatcatt    8700
ggaaaacgtt cttcggggcg aaaactctca aggatcttac cgctgttgag atccagttcg    8760
atgtaaccca ctcgtgcacc caactgatct tcagcatctt ttactttcac cagcgtttct    8820
gggtgagcaa aaacaggaag gcaaaatgcc gcaaaaaagg gaataagggc gacacggaaa    8880
tgttgaatac tcatactctt cctttttcaa tattattgaa gcatttatca gggttattgt    8940
ctcatgacca aaatccctta acgtgagttt tcgttccact gagcgtcaga ccccgtagaa    9000
```

```
aagatcaaag gatcttcttg agatcctttt tttctgcgcg taatctgctg cttgcaaaca   9060
aaaaaaccac cgctaccagc ggtggtttgt ttgccggatc aagagctacc aactcttttt   9120
ccgaaggtaa ctggcttcag cagagcgcag ataccaaata ctgttcttct agtgtagccg   9180
tagttaggcc accacttcaa gaactctgta gcaccgccta catacctcgc tctgctaatc   9240
ctgttaccag tggctgctgc cagtggcgat aagtcgtgtc ttaccgggtt ggactcaaga   9300
cgatagttac cggataaggc gcagcggtcg ggctgaacgg ggggttcgtg cacacagccc   9360
agcttggagc gaacgaccta caccgaactg agatacctac agcgtgagct atgagaaagc   9420
gccacgcttc ccgaagggag aaaggcggac aggtatccgg taagcggcag ggtcggaaca   9480
ggagagcgca cgagggagct tccaggggga aacgcctggt atctttatag tcctgtcggg   9540
tttcgccacc tctgacttga gcgtcgattt ttgtgatgct cgtcaggggg gcggagccta   9600
tggaaaaacg ccagcaacgc ggccttttta cggttcctgg ccttttgctg gccttttgct   9660
cacatgttct ttcctgcgtt atcccctgat tctgtggata accgtattac cgcctttgag   9720
tgagctgata ccgctcgccg cagccgaacg accgagcgca gcgagtcagt gagcgaggaa   9780
gcggaag                                                            9787

<210> SEQ ID NO 28
<211> LENGTH: 11649
<212> TYPE: DNA
<213> ORGANISM: Artificial Sequence
<220> FEATURE:
<223> OTHER INFORMATION: complete DNA sequence of plasmid pMT3378
<220> FEATURE:
<221> NAME/KEY: misc_feature
<222> LOCATION: (2545)..(2545)
<223> OTHER INFORMATION: n is a, c, g, or t
<220> FEATURE:
<221> NAME/KEY: misc_feature
<222> LOCATION: (2753)..(2753)
<223> OTHER INFORMATION: n is a, c, g, or t
<220> FEATURE:
<221> NAME/KEY: misc_feature
<222> LOCATION: (2844)..(2844)
<223> OTHER INFORMATION: n is a, c, g, or t

<400> SEQUENCE: 28
gaatacacgg aattcctcga gtaccattta attctatttg tgtttgatcg agacctaata     60
cagcccctac aacgaccatc aaagtcgtat agctaccagt gaggaagtgg actcaaatcg    120
acttcagcaa catctcctgg ataaacttta agcctaaact atacagaata agataggtgg    180
agagcttata ccgagctccc aaatctgtcc agatcatggt tgaccggtgc ctggatcttc    240
ctatagaatc atccttattc gttgacctag ctgattctgg agtgacccag agggtcatga    300
cttgagccta aaatccgccg cctccaccat ttgtagaaaa atgtgacgaa ctcgtgagct    360
ctgtacagtg accggtgact cttctggca tgcggagaga cggacggacg cagagagaag    420
ggctgagtaa taagccactg ccagacagc tctggcggct ctgaggtgca gtggatgatt    480
attaatccgg gaccggccgc ccctccgccc cgaagtggaa aggctggtgt gcccctcgtt    540
gaccaagaat ctattgcatc atcggagaat atggagcttc atcgaatcac cggcagtaag    600
cgaaggagaa tgtgaagcca ggggtgtata gccgtcggcg aaatagcatg ccattaacct    660
aggtacagaa gtccaattgc ttccgatctg gtaaaagatt cacagagatag tacccttctcc    720 gaagtaggta gagcgagtac ccggcgcgta agctccctaa ttggcccatc cggcatctgt    780
agggcgtcca aatatcgtgc ctctcctgct ttgcccggtt tatgaaaccg gaaaggccgc    840
tcaggagctg gccagcggcg cagaccggga acacaagctg gcagtcgacc catccggtgc    900
```

```
tctgcactcg acctgctgag gtccctcagt ccctggtagg cagctttgcc ccgtctgtcc    960
gcccggtgtg tcggcggggt tgacaaggtc gttgcgtcag tccaacattt gttgccatat   1020
tttcctgctc tccccaccag ctgtagatct tggtggcgtg aaactcccgc acctcttcgg   1080
ccagcgcctt gtagaagcgc gtatggcttc gtaccccggc catcaacacg cgtctgcgtt   1140
cgaccaggct gcgcgttctc gcggccatag caaccgacgt acggcgttgc gccctcgccg   1200
gcagcaagaa gccacggaag tccgcccgga gcagaaaatg cccacgctac tgcgggttta   1260
tatagacggt ccccacggga tgggaaaaac caccaccacg caactgctgg tggccctggg   1320
ttcgcgcgac gatatcgtct acgtacccga gccgatgact tactggcggg tgctgggggc   1380
ttccgagaca atcgcgaaca tctacaccac acaacaccgc ctcgaccagg gtgagatatc   1440
ggccggggac gcggcggtgg taatgacaag cgcccagata acaatgggca tgccttatgc   1500
cgtgaccgac gccgttctgg ctcctcatat cgggggggag gctgggagct cacatgcccc   1560
gcccccggcc ctcaccctca tcttcgaccg ccatcccatc gccgccctcc tgtgctaccc   1620
ggccgcgcgg taccttatgg gcagcatgac cccccaggcc gtgctggcgt tcgtggccct   1680
catcccgccg accttgcccg gcaccaacat cgtgcttggg gcccttccgg aggacagaca   1740
catcgaccgc ctggccaaac gccagcgccc cggcgagcgg ctggacctgg ctatgctggc   1800
tgcgattcgc cgcgtttacg ggctacttgc caatacggtg cggtatctgc agtgcggcgg   1860
gtcgtggcgg gaggactggg gacagctttc ggggacggcc gtgccgcccc agggtgccga   1920
gccccagagc aacgcgggcc cacgacccca tatcggggac acgttattta ccctgtttcg   1980
gggccccgag ttgctggccc ccaacggcga cctgtataac gtgtttgcct gggccttgga   2040
cgtcttggcc aaacgcctcc gttccatgca cgtctttatc ctggattacg accaatcgcc   2100
cgccggctgc cgggacgccc tgctgcaact tacctccggg atggtccaga cccacgtcac   2160
caccccggc tccataccga cgatatgcga cctggcgcgc acgtttgccc gggagatggg   2220
ggaggctaac tgaaacacgg aaggagacaa taccggaagg aacccgcgct atccggatcg   2280
atccacttaa cgttactgaa atcatcaaac agcttgacga atctggatat aagatcgttg   2340
gtgtcgatgt cagctccgga gttgagacaa atggtgttca ggatctcgat aagatacgtt   2400
catttgtcca agcagcaaag agtgccttct agtgatttaa tagctccatg tcaacaagaa   2460
taaaacgcgt tttcgggttt acctcttcca gatacagctc atctgcaatg cattaatgca   2520
ttgactgcaa cctagtaacg ccttncaggc tccggcgaag agaagaatag cttagcagag   2580
ctatttcat tttcgggaga cgagatcaag cagatcaacg gtcgtcaaga gacctacgag   2640
actgaggaat ccgctcttgg ctccacgcga ctatatattt gtctctaatt gtactttgac   2700
atgctcctct tctttactct gatagcttga ctatgaaaat tccgtcacca gcncctgggt   2760
tcgcaaagat aattgcatgt ttcttccttg aactctcaag cctacaggac acacattcat   2820
cgtaggtata aacctcgaaa tcanttccta ctaagatggt atacaatagt aaccatgcat   2880
ggttgcctag tgaatgctcc gtaacaccca atacgccggc cgaaactttt ttacaactct   2940
cctatgagtc gtttacccag aatgcacagg tacacttgtt tagaggtaat ccttcttttct   3000
agtcctgcag gtttaaacga attcgcccct cgatcgactt gaaaaccatg tctgacaatt   3060
ggatatacaa ccgtagcgta tgtatttgaa ctaatggat tgtggactgt gtatagccaa   3120
ttctatttcg tatgatggat cccttttcat ttaatctaac taaggtggat ataacttgaa   3180
ggctaacgat tgcgtctcgg gtaaggatca ccatcactat cctacgtgct taaggcccag   3240
gctggccatc aagcagctca tagagttcta cagaactctt ggtacatact gaaagaaatt   3300
```

```
cctaattggc tttggctatc cggggaaatt ttagcgagca gaaaatatcc ctacgctgag   3360
gtggaccgct cggtcgatcg gtatattgac cctctttaaa tcagccccca aatctccgat   3420
tatgtatgtc atcccaggac tttctacaat caatctactt cgcgtgtcaa tctaccgatt   3480
gtggagccat gtcagagaga aacatggtat caaatattga atttggtgca ctacacctag   3540
agtcggacct cagcaaagcc atcattgcat gggatggtca aatcgacacg cgaaatccaa   3600
ggagagaacc cgccatgact agcagagagc cctgcgctca gatgaatcgc aaagcccgag   3660
gattggtatc agcgaaagta tcatccacaa ttttgtctac cgacttgaca tagatagtcc   3720
cttccgatga atatattcca cctctcccaa ccactgaggc taatatgcag ttatcaacaa   3780
tccacgcaaa ccagcttgca ttagacccct ctgcttggat aacatccttg tttggcagga   3840
tttatctgat aggttcaata tagatactag acttctataa ttattcggag tgatccaaag   3900
ctgattccta tcttatcacc catgccgtcc gacgtatact gccaaagatt ataatcagag   3960
atgaaatgtt ggaaaataga gctgagcatt ctgcatctgg tcgttgtggt ctgtaacctt   4020
ggtgaggccc cgtctaaagg aacggatgct acacaaaact atggtttgtt agcatccaat   4080
atgtcgcatc tcttcccact actttgattc aaaccatggt acttggccgc atgacgtaaa   4140
atagacccgc tctggatcaa gattagtcta aagcttctct ggtactcttc gatctctctc   4200
ctcggttgca ttggcaagga ggttggcgac atctgatagt acacaccagg ttagcaagac   4260
tatacctatg tctacggagg attcatgact gtgaaactta catctatcta ccggtagact   4320
agggtcccgc aaagcattga gatccacttg tggtggccct gaggcctctg tcgagggccg   4380
tctgctggtc gactgagggg gacttagcgc cgtatactga gtcggaactt taggcacccc   4440
gggcaccggg ggcgcatttg cggagtcaag atcaggattg atctgtggat cctatggatc   4500
tcagaacaat ataccagaaa atgcgaaggt aagtgcttct atattgatcc ttagtgcttt   4560
caaactgtga tgtagaagtt gctcggtagc tgattaaata ttctagaccc aagccgctgc   4620
tggaattgac attattatgg ccgatagggt tgggcttatt gctatgtccc tgaaaggata   4680 tcaaagcag gcaaaaagcc aggcataatc cccgcgtgga cggtacccta aggataggcc   4740
ctaatcttat ctacatgtga ctgcatcgat gtgtttggtc aaaatgaggc atgtggctca   4800
ccccacaggc ggagaaacgt gtggctagtg catgacagtc ccctccatag attcaattta   4860 attttcgcg gcaattgtcg tgcagtttgt atctacattt cattccatat atcaagagtt   4920
agtagttgga catcctgatt attttgtcta attactgaaa actcgaagta ctaacctact   4980
aataagccag tttcaaccac taagtgctca tttatacaat atttgcagaa ccccgcgcta   5040
cccctccatc gccaacatgt cttccaagtc gcaattgacc tacagcgcac gcgctagcaa   5100
gcaccccaat gcgctcgtaa agaagctctt cgaggttgcc gaggccaaga aaaccaatgt   5160 caccgttttcc gccgacgtga caaccaccaa agagctgctg gatttggctg accgtatgcg   5220
caccggggat gccacttaca tgtgatctag taatggttaa tggtggatta tataacagga   5280
ctcggtccgt acattgccgt gatcaaaact cacatcgata tcctctccga tttcagcgaa   5340
gaaaccatca ccggtctgaa ggcccttgca gagaagcaca atttcctcat cttcgaagat   5400
cgcaagttca tcgatatcgg aaacacagtc caaaagcagt accatggcgg cactctgcgt   5460
atctctgagt gggcccacat catcaactgc agtattctgc ccggtgaggg tatcgtcgag   5520
gctctggccc agactgcttc ggccgaggac ttcccctacg ctccgagag gggccttttg   5580 atccttgcgc agatgacctc caagggatct ttggctaccg gtcaatatac tacttcttct   5640
gttgactatg ctcggaagta taagaagttt gtgatgggat tcgtctcgac acgtcacctt   5700
```

```
ggcgaggttc agtctgaagt tagctcgcct tcggaggagg aagattttgt cgtcttcacg   5760
acaggtgtca acctctcctc gaagggtgac aagctgggac agcagtacca aactcctgag   5820
tcggctgttg gacgcggtgc cgactttatt attgctggcc gtggaattta tgctgctcct   5880
gatcccgtgg aggcggcgaa gcagtaccag aaggagggat gggatgcata cctgaagcgt   5940
gttggtgcgc aataagtagt ggtggatacg tactccttttt atggcagtat gtcgcaagta   6000
tgatgcgatt tataaattca gcactcgaaa tgactactac tatgtgtcta cgacagatac   6060
cctctccgta cgaataagac acctgcctcg atatatggac aaattcaaaa tcagggtcaa   6120
gggtcatgtt tcaaagtcac aacaatctcc aacatagacg agaatttgta ccggagtgtc   6180
tgaaggtgca gctggagatt ggtctatttt cttagagtgg ggtatcacta atgtacagtc   6240
ggtcactatc gtacaaacaa tcacaattat atacaagatt tcccaccacc ccctactcta   6300
acacggcaca attatccatc gagtcagagc ctagccacca tttggtgctc tcgtagagac   6360
caaagtataa tcctgatccg acagcggcca taaacgtgtt gatagcacac cctcggaata   6420
gtcctctcgg gccatctgtt cgtacaatct cccgtacggt attgatcatc cttttcttct   6480
gaggtgcagt tgtatctgca gcatcgagca tgattcgtgt ccggaccata tccatgggtg   6540
ctgtcaagac actagctata ccgcccgaga ccgcagcact tattgcggct gtcgctgcag   6600
cctctccgat tgtcgaatgg gcctcttttct ttccatactc tcttggtctt tctagcacct   6660
tctctcgatc tccgaatcta tattcaaaaa ttcgataccg aaaagactcg tacagaggca   6720
tctgaatcgc cgacactggc aagctatgcg ccacaagagc cgggtatccg ctccaaagct   6780
gtctagggtt gataaacttc ttgaaagcta gccgtgtcgc tttctgggct acaccaccta   6840
cccttccccc agctacaggt gctgatgcgt ctggatggtg tgattggatc atctgcgcgt   6900
tgtgttttaa tgcatcagcc ggagcaaaga ctccgcaagc agcaagatcc gcaacggagg   6960
ctgcgcaaaa atcggaaaag agccgagctg agctagactc atgcgttcca agttttttgat  7020 gtatgacttg gagtcctgac tgtgcatact cgtatgtgat gaagaatgcg cccgctttga   7080
cccgttattt tttgctcaat gaatatgagt tgggtaagga taatgttggg tatcaccaac   7140
ctgtgggaaa tgaggcagcg gttacgctcg cgataccttg gtaaaggccg cggaatatcc   7200
ctgggtgtct ccatatgctg gttcctgtgt tggttctcag gaactgcgaa tattcgcgag   7260
actgaatgcg ggttttgatc gtatctaagg gatatgtgaa tagatctctc tggtactctt   7320
cgatctctct cctcggttgc attggcaagg aggttggcga catctgatag tacacaccag   7380
gttagcaaga ctatacctat gtctacggag gattcatgac tgtgaaactt acatctatct   7440
accggtagac tagggtcccg caaagcattg agatccactt gtggtggccc tgaggcctct   7500
gtcgagggcc gtctgctggt cgactgaggg ggacttagcg ccgtatactg agtcggaact   7560
ttaggcaccc cgggcaccgg gggcgcattt gcggagtcaa gatcaggatt gatctgtgga   7620
tcctatggat ctcagaacaa taccagaa aatgcgaagg taagtgcttc tatattgatc   7680
cttagtgctt tcaaactgtg atgtagaaga agcttgtgat aggggttac cactcattgc   7740 atttcagtag taaccccga aatagataag aaagcatggt cgtgcagtat tagtatattt    7800
aggaaaaggt cattaatcat taccaacaca cttgcgttga gtcatcttac tcaaccggcc   7860
tccttcccca cacaacatga aacttcccat agatatgcac cctaggatct tcaactcat   7920 tccgcacaga ggccaagaaa actgctacct ccaccgggga ccagccgaga accccttgtac  7980 aaagcgcaag agcatacgac tcaagactca taaccatgac ttcgcgatgg aaccgaccgg   8040 cttctttttaa tcgcttttct ttagcccagg gacccatcgg gaactacaga aattaagtta   8100
```

```
atacccgata gattaacgga gtattaaacc agagggagag cgaaagtaga aaaaacctac   8160
cttgtagatc tttccttca catcggtgaa ccctgcgtct atcatatttc tctgatggtc   8220
ggccgccacc ttcattggcc ggttaaacct cgagcttgcc tcaatcaaca gtctgaacca   8280
ctcgcccagt gagggcgcca gatcgagtgt gtcatcgtca gagaaatgtt ccatctcaaa   8340
gtcggatagt tccaaccatc cacctggctt catgtgtgaa tatgcctggc gcagcagttt   8400
cggccagtcg gcgatcgaac cggcaaggtc gcatgcacgg atgaagtcga agtaatctcg   8460
tttgaaagtc cagtcggctt cgacgtcgtc gacgaagaat tcgaggttcg gagggaccca   8520
ggcgggttgg atgggctga gatcggtgcc gattactcgg gcgttggggt gtgtgtctgc   8580
gaagtcgatg gcccagatac ctttattatt atttggtcag ccatgagcga gcgggtttcc   8640
tggaatagat acggcatgtg ccatacctgt tccggtgcca atgtcgaaaa cgttctcaac   8700
atcctctggg atcggggcgt gaaagagatc tccactgaaa tgcagattgc gaacgtggtg   8760
taataggtcc tcgcgatctt gctcttgttc gtcgtttggc agcacacact gcccttcgcg   8820
gtaggagtgg tatcgacggc cattctcgta cttgtagttt caagggcgaa ttcgcggccg   8880
ctctgcatta atgaatcggc caacgcgcgg ggagaggcgg tttgcgtatt gggcgctctt   8940
ccgcttcctc gctcactgac tcgctgcgct cggtcgttcg gctgcggcga gcggtatcag   9000
ctcactcaaa ggcggtaata cggttatcca cagaatcagg ggataacgca ggaaagaaca   9060
tgtgagcaaa aggccagcaa aaggccagga accgtaaaaa ggccgcgttg ctggcgtttt   9120
tccataggct ccgcccccct gacgagcatc acaaaaatcg acgctcaagt cagaggtggc   9180
gaaacccgac aggactataa agataccagg cgtttccccc tggaagctcc ctcgtgcgct   9240
ctcctgttcc gaccctgccg cttaccggat acctgtccgc ctttctccct tcgggaagcg   9300
tggcgctttc tcatagctca cgctgtaggt atctcagttc ggtgtaggtc gttcgctcca   9360
agctgggctg tgtgcacgaa ccccccgttc agcccgaccg ctgcgcctta tccggtaact   9420
atcgtcttga gtccaacccg gtaagacacg acttatcgcc actggcagca gccactggta   9480
acaggattag cagagcgagg tatgtaggcg gtgctacaga gttcttgaag tggtggccta   9540
actacggcta cactagaagg acagtatttg gtatctgcgc tctgctgaag ccagttacct   9600
tcggaaaaag agttggtagc tcttgatccg gcaaacaaac caccgctggt agcggtggtt   9660
tttttgtttg caagcagcag attacgcgca gaaaaaaagg atctcaagaa gatcctttga   9720
tcttttctac ggggtctgac gctcagtgga acgaaaactc acgttaaggg attttggtca   9780
tgagattatc aaaaaggatc ttcacctaga tccttttaaa ttaaaaatga agttttaaat   9840
caatctaaag tatatatgag taaacttggt ctgacagtta ccaatgctta atcagtgagg   9900
cacctatctc agcgatctgt ctatttcgtt catccatagt tgcctgactc cccgtcgtgt   9960
agataactac gatacgggag ggcttaccat ctggccccag tgctgcaatg ataccgcgag  10020
acccacgctc accggctcca gatttatcag caataaacca gccagccgga agggccgagc  10080
gcagaagtgg tcctgcaact ttatccgcct ccatccagtc tattaattgt tgccgggaag  10140
ctagagtaag tagttcgcca gttaatagtt tgcgcaacgt tgttgccatt gctacaggca  10200
tcgtggtgtc acgctcgtcg tttggtatgg cttcattcag ctccggttcc caacgatcaa  10260
ggcgagttac atgatccccc atgttgtgca aaaaagcggt tagctccttc ggtcctccga  10320
tcgttgtcag aagtaagttg gccgcagtgt tatcactcat ggttatggca gcactgcata  10380
attctcttac tgtcatgcca tccgtaagat gcttttctgt gactggtgag tactcaacca  10440
agtcattctg agaatagtgt atgcggcgac cgagttgctc ttgcccggcg tcaatacggg  10500
```

```
ataataccgc gccacatagc agaactttaa aagtgctcat cattggaaaa cgttcttcgg    10560
ggcgaaaact ctcaaggatc ttaccgctgt tgagatccag ttcgatgtaa cccactcgtg    10620
cacccaactg atcttcagca tcttttactt tcaccagcgt ttctgggtga gcaaaaacag    10680
gaaggcaaaa tgccgcaaaa aagggaataa gggcgacacg gaaatgttga atactcatac    10740
tcttcctttt tcaatattat tgaagcattt atcagggtta ttgtctcatg agcggataca    10800
tatttgaatg tatttagaaa aataaacaaa taggggttcc gcgcacattt ccccgaaaag    10860
tgccacctga cgtctaagaa accattatta tcatgacatt aacctataaa aataggcgta    10920
tcacgaggcc ctttcgtctc gcgcgtttcg gtgatgacgg tgaaaacctc tgacacatgc    10980
agctcccgga gacggtcaca gcttgtctgt aagcggatgc cgggagcaga caagcccgtc    11040
agggcgcgtc agcgggtgtt ggcgggtgtc ggggctggct taactatgcg gcatcagagc    11100
agattgtact gagagtgcac catatcgacg ctctccctta tgcgactcct gcattaggaa    11160
gcagcccagt agtaggttga ggccgttgag caccgccgcc gcaaggaatg gtgcatgcaa    11220
ggagatggcg cccaacagtc ccccggccac ggggcctgcc accataccca cgccgaaaca    11280
agcgctcatg agcccgaagt ggcgagcccg atcttcccca tcggtgatgt cggcgatata    11340
ggcgccagca accgcacctg tggcgccggt gatgccggcc acgatgcgtc cggcgtagag    11400
gatctggcta gcgatgaccc tgctgattgg ttcgctgacc atttccgggg tgcggaacgg    11460
cgttaccaga aactcagaag gttcgtccaa ccaaaccgac tctgacggca gtttacgaga    11520
gagatgatag ggtctgcttc agtaagccag atgctacaca attaggcttg tacatattgt    11580
cgttagaacg cggctacaat taatacataa ccttatgtat catacacata cgatttaggt    11640
gacactata                                                             11649

<210> SEQ ID NO 29
<211> LENGTH: 7616
<212> TYPE: DNA
<213> ORGANISM: Artificial Sequence
<220> FEATURE:
<223> OTHER INFORMATION: complete DNA sequence of plasmid pMT3431

<400> SEQUENCE: 29
ggacgcacca tccaattaga agcagcaaag cgaaacagcc caagaaaaag gtcggcccgt      60
cggccttttc tgcaacgctg atcacgggca gcgatccaac caacaccctc cagagtgact     120
aggggcggaa atttatcggg attaatttcc actcaaccac aaatcacagt cgtcccggt     180 aatttaacgg ctgcagacgg caatttaacg gcttctgcga atcgcttgga ttccccgccc     240
ctggccgtag agcttaaagt atgtcccttg tcgatgcgat gtatgaattc atggtgtttt     300
gatcatttta aattttttata tggcgggtgg tgggcaactc gcttgcgcgg gcaactcgct     360
taccgattac gttagggctg atatttacgt aaaaatcgtc aagggatgca agaccaaacc     420
gttaaatttc cggagtcaac agcatccaag cccaagtcct tcacggagaa accccagcgt     480
ccacatcacg agcgaaggac cacctctagg catcggacgc accatccaat tagaagcagc     540
aaagcgaaac agcccaagaa aaaggtcggc cgtcggcct tttctgcaac gctgatcacg     600
ggcagcgatc caaccaacac cctccagagt gactaggggc ggaaatttat cggattaat     660 ttccactcaa ccacaaatca cagtcgtccc cggtaattta acggctgcag acggcaattt     720
aacggcttct gcgaatcgct tggattcccc gccctggcc gtagagctta agtatgtcc     780 cttgtcgatg cgatgtatca aacatataa atactggcaa gggatgccat gcttggagtt     840
tccaactcaa tttacctcta tccacacttc tcttccttcc tcaatcctct atatacacaa     900
```

```
ctggggatcc accatgagga gctcccttgt gctgttcttt gtctctgcgt ggacggcctt    960
ggctagccct attcgtcctc gaccggtctc gcaggatctg tttaaccagt tcaatctctt   1020
tgcacagtat tcagctgccg catactgcgg aaaaaacaat gatgcccag caggtacaaa   1080
cattacgtgc acgggaaatg cctgccccga ggtagagaag gcggatgcaa cgtttctcta   1140
ctcgtttgaa gactctggag tgggcgatgt caccggcttc cttgctctcg acaacacgaa   1200
caaattgatc gtcctctctt tccgtggctc tcgttccata gagaactgga tcgggaatct   1260
taacttcgac ttgaaaaaaa taaatgacat ttgctccggc tgcaggggac atgacggctt   1320
cacttcgtcc tggaggtctg tagccgatac gttaaggcag aaggtggagg atgctgtgag   1380
ggagcatccc aactatcgcg tggtgtttac cggacatagc ttgggtggtg cattggcaac   1440
tgttgccgga gcagacctgc gtggaaatgg gtatgatatc gacgtgtttt catatggcgc   1500
cccccgagtc ggaaacaggg cttttgcaga attcctgacc gtacagaccg gcggaacact   1560
ctaccgcatt acccacacca atgatattgt ccctagactc ccgccgcgcg aattcggtta   1620
cagccattct agcccagaat actggatcaa atctggaacc cttgtccccg tcacccgaaa   1680
cgatatcgtg aagatagaag gcatcgatgc caccggcggc aataaccggc cgaacattcc   1740
ggatatccct gcgcacctat ggtacttcgg gttaattggg acatgtcttt agtgcgcggc   1800
gcggctgggt cgactctagc gagctcgaga tctagagggt gactgacacc tggcggtaga   1860
caatcaatcc atttcgctat agttaaagga tggggatgag ggcaattggt tatatgatca   1920
tgtatgtagt gggtgtgcat aatagtagtg aaatggaagc caagtcatgt gattgtaatc   1980
gaccgacgga attgaggata tccggaaata cagacaccgt gaaagccatg gtctttcctt   2040
cgtgtagaag accagacaga cagtccctga tttacccttg cacaaagcac tagaaaatta   2100
gcattccatc cttctctgct tgctctgctg atatcactgt cattcaatgc atagccatga   2160
gctcatctta gatccaagca cgtaattcca tagccgaggt ccacagtgga gcagcaacat   2220
tccccatcat tgcttttccc cagggcctcc caacgactaa atcaagagta tatctctacc   2280
gtccaataga tcgtcttcgc ttcaaaatct ttgacaattc caagagggtc ccatccatc   2340
aaacccagtt caataatagc cgagatgcat ggtggagtca attaggcagt attgctggaa   2400
tgtcggggcc agttggccgg gtggtcattg gccgcctgtg atgccatctg ccactaaatc   2460
cgatcattga tccaccgccc acgaggcgcg tctttgcttt ttgcgcggcg tccaggttca   2520
actctctcct ctagactgga aacgcaaccc tgaagggatt cttcctttga gagatggaag   2580
cgtgtcatat ctcttcggtt ctacggcagg ttttttttctg ctctttcgta gcatggcatg   2640
gtcacttcag cgcttattta cagttgctgg tattgatttc ttgtgcaaat tgctatctga   2700
cacttattag ctatggagtc accacatttc ccagcaactt ccccacttcc tctgcaatcg   2760
ccaacgtcct ctcttcactg agtctccgtc cgataacctg cactgcaacc ggtgccccat   2820
ggtacgcctc cggatcatac tcttcctgca cgagggcatc aagctcacta accgccttga   2880
aactctcatt cttcttatcg atgttcttat ccgcaaaggt aaccgaaaca accacgctcg   2940
tgaaatccag caggttgatc acagaggcat acccatagta ccggaactgg tcatgccgta   3000
ccgcagcggt aggcgtaatc ggcgcgatga tggcgtccag ttccttcccg gccttttctt   3060
cagcctcccg ccatttctca aggtactcca tctggtaatt ccacttctgg agatgcgtgt   3120
cccagagctc gttcatgtta acagctttga tgttcgggtt cagtaggtct ttgatatttg   3180
gaatcgccgg ctcgccggat gcactgatat cgcgcattac gtcggcgctg ccgtcagccg   3240
cgtagatatg ggagatgaga tcgtggccga aatcgtgctt gtatggcgtc cacggggtca   3300
```

```
cggtgtgacc ggctttggcg agtgcggcga cggtggtttc cacgccgcgc aggataggag    3360
ggtgtggaag gacattgccg tcgaagttgt agtagccgat attgagcccg ccgttcttga    3420
tcttggaggc aataatgtcc gactcggact ggcgccaggg catggggatg accttggagt    3480
cgtatttcca tggctcctga ccgaggacgg atttggtgaa gaggcggagg tctaacatac    3540
ttcatcagtg actgccggtc tcgtatatag tataaaaagc aagaaaggag gacagtggag    3600
gcctggtata gagcaggaaa agaaggaaga ggcgaaggac tcaccctcaa cagagtgcgt    3660
aatcggcccg acaacgctgt gcaccgtctc ctgaccctcc atgctgttcg ccatctttgc    3720
atacggcagc cgcccatgac tcggccttag accgtacagg aagttgaacg cggccggcac    3780
tcgaatcgag ccaccgatat ccgttcctac accgatgacg ccaccacgaa tcccaacgat    3840
cgcaccctca ccaccagaac tgccgccgca cgaccagttc ttgttgcgtg ggttgacggt    3900
gcgcccgatg atgttgttga ctgtctcgca gaccatcagg gtctgcggga cagaggtctt    3960
gacgtagaag acggcaccgg cttttgcgag catggttgtc agaaccgagt cccccttcgtc    4020 gtacttgttt agccatgaga tgtagcccat tgatgtttcg tagccctggt ggcatatgtt    4080
agctgacaaa aagggacatc taacgactta ggggcaacgg tgtaccttga ctcgaagctg    4140
gtctttgaga gagatgggga ggccatggag tggaccaacg ggtctcttgt gctttgcgta    4200
gtattcatcg agttcccttg cctgcgcgag agcggcgtca gggaagaact cgtgggcgca    4260
gtttgtctgc acagaagcca gcgtcagctt gatagtccca taaggtggcg ttgttacatc    4320
tccctgagag gtagagggga ccctactaac tgctgggcga ttgctgcccg tttacagaat    4380
gctagcgtaa cttccaccga ggtcaactct ccggccgcca gcttggacac aagatctgca    4440
gcggaggcct ctgtgatctt cagttcggcc tctgaaagga tcaccgattt ctttgggaaa    4500
tcaataacgc tgtcttccgc aggcagcgtc tggactttcc attcatcagg gatggttttt    4560
gcgaggcggg cgcgcttatc agcggccagt tcttcccagg attgaggcat tctgtgttag    4620
cttatagtca ggatgttggc tcgacgagtg taaactggga gttggcatga gggttatgta    4680
ggcttcttta gccccgcatc cccctcattc tcctcattga tcccggggga gcggatggtg    4740
ttgataagag actaattata gggtttagct ggtgcctagc tggtgattgg ctggcttcgc    4800
cgaattttac gggccaagga aagctgcaga accgcggcac tggtaaacgg taattaagct    4860
atcagcccca tgctaacgag tttaaattac gtgtattgct gataaacacc aacagagctt    4920
tactgaaaga tgggagtcac ggtgtggctt ccccactgcg attattgcac aagcagcgag    4980
ggcgaacttg actgtcgtcg ctgagcagcc tgcagtcaaa catacatata tatcaaccgc    5040
gaagacgtct ggccttgtag aacacgacgc tccctagcaa cacctgccgt gtcagcctct    5100
acggttgtta cttgcattca ggatgctctc cagcgggcga gctattcaaa atattcaaag    5160
caggtatctc gtattgccag gattcagctg aagcaacagg tgccaaggaa atctgcgtcg    5220
gttctcatct gggcttgctc ggtcctggcg tagatctaga gtcgacctgc aggcatgcgg    5280
cgtaatcatg gtcatagctg tttcctgtgt gaaattgtta ccgctcaca attccacaca    5340 acatacgagc cggaagcata aagtgtaaag cctggggtgc ctaatgagtg agctaactca    5400
cattaattgc gttgcgctca ctgcccgctt tccagtcggg aaacctgtcg tgccagctgc    5460
attaatgaat cggccaacgc gcgggggagag gcggtttgcg tattgggcgc tcttccgctt    5520
cctcgctcac tgactcgctg cgctcggtcg ttcggctgcg gcgagcggta tcagctcact    5580
caaaggcggt aatacggtta tccacagaat caggggataa cgcaggaaag aacatgtgag    5640
caaaaggcca gcaaaaggcc aggaaccgta aaaaggccgc gttgctggcg ttttttccata    5700
```

```
ggctccgccc ccctgacgag catcacaaaa atcgacgctc aagtcagagg tggcgaaacc    5760
cgacaggact ataaagatac caggcgtttc ccctggaag ctccctcgtg cgctctcctg     5820
ttccgaccct gccgcttacc ggatacctgt ccgcctttct ccttcggga agcgtggcgc     5880 tttctcatag ctcacgctgt aggtatctca gttcggtgta ggtcgttcgc tccaagctgg    5940
gctgtgtgca cgaacccccc gttcagcccg accgctgcgc cttatccggt aactatcgtc    6000
ttgagtccaa cccggtaaga cacgacttat cgccactggc agcagccact ggtaacagga    6060
ttagcagagc gaggtatgta ggcggtgcta cagagttctt gaagtggtgg cctaactacg    6120
gctacactag aagaacagta tttggtatct gcgctctgct gaagccagtt accttcggaa    6180
aaagagttgg tagctcttga tccgacaaac aaaccaccgc tggtagcggt ggtttttttg    6240
tttgcaagca gcagattacg cgcagaaaaa aaggatctca agaagatcct ttgatctttt    6300
ctacggggtc tgacgctcag tggaacgaaa actcacgtta agggattttg gtcatgagat    6360
tatcaaaaag gatcttcacc tagatccttt taaattaaaa atgaagtttt aaatcaatct    6420
aaagtatata tgagtaaact tggtctgaca gttaagcaag gattttctta acttcttcgg    6480
cgacagcatc accgacttcg gtggtactgt tggaaccacc taaatcacca gttctgatac    6540
ctgcatccaa aaccttttta actgcatctt caatggcctt accttcttca ggcaagttca    6600
atgacaattt caacatcatt gcagcagaca agatagtggc gatagggttg accttattct    6660
ttggcaaatc tggagcagaa ccgtggcatg gttcgtacaa accaaatgcg gtgttcttgt    6720
ctggcaaaga ggccaaggac gcagatggca acaaacccaa ggaacctggg ataacggagg    6780
cttcatcgga gatgatatca ccaaacatgt tgctggtgat tataatacca tttaggtggg    6840
ttgggttctt aactaggatc atggcggcag aatcaatcaa ttgatgttga accttcaatg    6900
tagggaattc gttcttgatg gtttcctcca cagtttttct ccataatctt gaagaggcca    6960
aaacattagc tttatccaag gaccaaatag gcaatggtgg ctcatgttgt agggccatga    7020
aagcggccat tcttgtgatt cttttgcactt ctggaacggt gtattgttca ctatcccaag    7080
cgacaccatc accatcgtct tcctttctct taccaaagta aatacctccc actaattctc     7140
tgacaacaac gaagtcagta cctttagcaa attgtggctt gattggagat aagtctaaaa    7200
gagagtcgga tgcaaagtta catggtctta agttggcgta caattgaagt tctttacgga    7260
tttttagtaa accttgttca ggtctaacac tgccggtacc ccatttagga ccacccacag    7320
cacctaacaa aacggcatca gccttcttgg aggcttccag cgcctcatct ggaagtggaa    7380
cacctgtagc atcgatagca gcaccaccaa ttaaatgatt ttcgaaatcg aacttgacat    7440
tggaacgaac atcagaaata gctttaagaa ccttaatggc ttcggctgtg atttcttgac    7500
caacgtggtc acctggcaaa acgacgatct tcttaggggc agacatactc ttccttttc     7560 aatattattg aagcatttat cagggttatt gtctcatgag cggatacata tttgaa        7616
```

<210> SEQ ID NO 30
<211> LENGTH: 20
<212> TYPE: DNA
<213> ORGANISM: Artificial Sequence
<220> FEATURE:
<223> OTHER INFORMATION: PCR primer

<400> SEQUENCE: 30
ggtaaccccc tatcacaagc                                                    20

<210> SEQ ID NO 31
<211> LENGTH: 22

```
<212> TYPE: DNA
<213> ORGANISM: Artificial Sequence
<220> FEATURE:
<223> OTHER INFORMATION: PCR primer

<400> SEQUENCE: 31
cgatcgactt gaaaaccatg tc                                          22

<210> SEQ ID NO 32
<211> LENGTH: 23
<212> TYPE: DNA
<213> ORGANISM: Artificial Sequence
<220> FEATURE:
<223> OTHER INFORMATION: PCR primer

<400> SEQUENCE: 32
gaaactacaa gtacgagaat ggc                                         23

<210> SEQ ID NO 33
<211> LENGTH: 44
<212> TYPE: DNA
<213> ORGANISM: Artificial Sequence
<220> FEATURE:
<223> OTHER INFORMATION: PCR primer

<400> SEQUENCE: 33
gcttgtgata gggggttacc actcattgca tttcagtagt aacc                  44

<210> SEQ ID NO 34
<211> LENGTH: 18
<212> TYPE: DNA
<213> ORGANISM: Artificial Sequence
<220> FEATURE:
<223> OTHER INFORMATION: PCR primer

<400> SEQUENCE: 34
gttacgccac gtccctgc                                               18

<210> SEQ ID NO 35
<211> LENGTH: 21
<212> TYPE: DNA
<213> ORGANISM: Artificial Sequence
<220> FEATURE:
<223> OTHER INFORMATION: PCR primer

<400> SEQUENCE: 35
ccccagtcag tacatgcttc g                                           21

<210> SEQ ID NO 36
<211> LENGTH: 25
<212> TYPE: DNA
<213> ORGANISM: Artificial Sequence
<220> FEATURE:
<223> OTHER INFORMATION: PCR primer

<400> SEQUENCE: 36
gatctacaag gtaggttttt tctac                                       25

<210> SEQ ID NO 37
<211> LENGTH: 29
<212> TYPE: DNA
<213> ORGANISM: Artificial Sequence
<220> FEATURE:
<223> OTHER INFORMATION: PCR primer

<400> SEQUENCE: 37
ggatcccttt tcatttaatc taactaagg                                   29
```

```
<210> SEQ ID NO 38
<211> LENGTH: 30
<212> TYPE: PRT
<213> ORGANISM: Aspergillus oryzae
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (15)..(16)
<223> OTHER INFORMATION: Xaa can be any naturally occurring amino acid
<220> FEATURE:
<221> NAME/KEY: misc_feature
<222> LOCATION: (22)..(26)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid

<400> SEQUENCE: 38

Glu Xaa Xaa Cys Gly Xaa Xaa Gly Xaa Met Xaa Xaa Asp Pro Xaa Xaa
1               5                   10                  15

Leu Pro Glu Gly Val Xaa Xaa Xaa Xaa Xaa Arg Xaa Cys Ala
            20                  25                  30
```

US 8,415,119 B2

METHOD FOR INCREASING EXPRESSION YIELD OF A PROTEIN OF INTEREST

CROSS-REFERENCE TO RELATED APPLICATIONS

This application is a 35 U.S.C. 371 national application of PCT/EP2009/052056 filed Feb. 20, 2009, which claims priority or the benefit under 35 U.S.C. 119 of European application no. 08151903.5 filed Feb. 25, 2008 and U.S. provisional application No. 61/031,206 filed Feb. 25, 2008, the contents of which are fully incorporated herein by reference.

REFERENCE TO A SEQUENCE LISTING

This application contains a Sequence Listing in computer readable form. The computer readable form is incorporated herein by reference.

BACKGROUND OF THE INVENTION

1. Field of the Invention

The present invention relates to methods of increasing expression yield of a protein of interest. The present invention in particular relates to isolated polypeptides and isolated polynucleotides encoding polypeptides of the invention. The invention furthermore relates to nucleic acid constructs, vectors, and host cells comprising the polynucleotides as well as methods of producing and using the polypeptides.

2. Description of the Related Art

The use of recombinant host cells in the expression of heterologous proteins has in recent years greatly simplified the production of large quantities of commercially valuable proteins which otherwise are obtainable only by purification from their native sources. Currently, there is a varied selection of expression systems from which to choose for the production of any given protein, including bacterial and eukaryotic hosts. The selection of an appropriate expression system often depends not only on the ability of the host cell to produce adequate yields of the protein in an active state, but, to a large extent, may also be governed by the intended end use of the protein.

Typically improved yields have been obtained by improving the stability of the protein product by using different protease mutants or increasing the expression by using a strong promoter for controlling the expression or improving the secretion pathway by using the most efficient signal peptides.

Host cells used for heterologous protein expression are known to be in a state of stress since the protein synthsizing machinery will be pushed to the limit (Rutkowski, D. T., and Kaufman, R. J. (2004), "A trip to the ER: coping with stress", Trends in Cell Biology 14 (1): 20-28). Proteins involved in stress responses could therefore be advantageously manipulated leading to improved yield of protein products.

It is an object of the present invention to provide such polypeptides the expressions of which are induced or increased during stress conditions and provide methods for improving yield by modifying the expression.

SUMMARY OF THE INVENTION

The present invention relates to isolated polypeptides selected from the group consisting of:
(a) a polypeptide comprising an amino acid sequence having at least 66%, more preferably at least 70%, more preferably at least 75%, more preferably at least 80%, even more preferably at least 85%, most preferably at least 90%, and even most preferably at least 95% identity to the mature polypeptide of SEQ ID NO: 2;
(b) a polypeptide encoded by a polynucleotide that hybridizes under at least medium stringency conditions, even more preferably at least medium-high stringency conditions, and most preferably at least high stringency conditions with (i) the mature polypeptide coding sequence of SEQ ID NO: 1, (ii) cDNA sequence contained in the DNA sequence comprising the mature polypeptide coding sequence of SEQ ID NO: 1, or (iii) a full-length complementary strand of (i) or (ii);
(c) a polypeptide encoded by a polynucleotide comprising a nucleotide sequence having preferably at least 60%, more preferably at least 65%, more preferably at least 70%, more preferably at least 75%, more preferably at least 80%, even more preferably at least 85%, most preferably at least 90%, and even most preferably at least 95% identity to the mature polypeptide coding sequence of SEQ ID NO: 1;
(d) a variant comprising a substitution, deletion, and/or insertion of one or more (several) amino acids of the mature polypeptide of SEQ ID NO: 2.

The present invention also relates to isolated polynucleotides encoding the polypeptides of the invention.

The present invention also relates to nucleic acid constructs, recombinant expression vectors, recombinant host cells comprising the polynucleotides, and methods of producing a polypeptide of the invention.

The present invention in a further aspect relates to a method of producing the polypeptide of the invention, comprising: (a) cultivating a cell, which in its wild-type form produces the polypeptide, under conditions conducive for production of the polypeptide; and (b) recovering the polypeptide.

The present invention in a further aspect relates to a method of producing the polypeptide of the invention, comprising: (a) cultivating a host cell comprising a nucleic acid construct comprising a nucleotide sequence encoding the polypeptide under conditions conducive for production of the polypeptide; and (b) recovering the polypeptide.

The present invention also relates to a mutant fungal host, wherein the mutant has a reduced or no expression of an endogenous polypeptide selected from the group consisting of:
(a) a polypeptide comprising an amino acid sequence having at least 66%, more preferably at least 70%, more preferably at least 75%, more preferably at least 80%, even more preferably at least 85%, most preferably at least 90%, and even most preferably at least 95% identity to the mature polypeptide of SEQ ID NO: 2;
(b) a polypeptide encoded by a polynucleotide that hybridizes under at least medium stringency conditions, even more preferably at least medium-high stringency conditions, and most preferably at least high stringency conditions with (i) the mature polypeptide coding sequence of SEQ ID NO: 1, (ii) cDNA sequence contained in the DNA sequence comprising the mature polypeptide coding sequence of SEQ ID NO: 1, or (iii) a full-length complementary strand of (i) or (ii);
(c) a polypeptide encoded by a polynucleotide comprising a nucleotide sequence having preferably at least 60%, more preferably at least 65%, more preferably at least 70%, more preferably at least 75%, more preferably at least 80%, even more preferably at least 85%, most preferably at least 90%, and even most preferably at least 95% identity to the mature polypeptide coding sequence of SEQ ID NO: 1;

(d) a polypeptide induced during apoptosis and comprising the motif: EXXCGXXGXMXXDPXX-LPEGVXXXXXRXCA; and (e) a variant comprising a substitution, deletion, and/or insertion of one or several amino acids of the mature polypeptide of SEQ ID NO: 2.

The present invention also relates to a method of producing a protein of interest comprising: (a) cultivating a mutant cell under conditions conducive for production of the protein wherein the mutant has a reduced or no expression of an endogenous polypeptide compared to a parent host cell grown under the same conditions, and wherein the expression of said endogenous polypeptide commits the cell to apoptosis; and optionally (b) recovering the protein of interest.

The present invention also relates to methods of producing a protein of interest comprising: (a) cultivating the mutant cell according to the invention further expressing the protein of interest under conditions conducive for production of the protein; and optionally (b) recovering the protein.

BRIEF DESCRIPTION OF THE FIGURES

FIG. 1 shows the cDNA sequence and the deduced amino acid sequence of *Aspergillus oryzae* ZY082808 (SEQ ID NOs: 1 and 2, respectively).

DEFINITIONS

Polypeptide induced during apoptosis: The term "expression of said endogenous polypeptide commits the cell to apoptosis" is defined herein to mean that once the endogenous polypeptide has been expressed the host cell will eventually undergo apoptosis.

Apoptosis: The term "apoptosis" is defined herein as cell death resulting from induction of an internal suicide program which prior to the cell death includes cleavage of caspase substrates.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature polypeptide: The term "mature polypeptide" is defined herein as a polypeptide that is in its final form following translation and any post-translational modifications, such as N-terminal processing, C-terminal truncation, glycosylation, phosphorylation, etc. In a preferred aspect, the mature polypeptide is amino acids 20 to 79 of SEQ ID NO: 2 based on the SignalP3.0 program that predicts amino acids 1 to 19 of SEQ ID NO: 2 are a signal peptide.

Mature polypeptide coding sequence: The term "mature polypeptide coding sequence" is defined herein as a nucleotide sequence that encodes a mature polypeptide. In a preferred aspect, the mature polypeptide coding sequence is nucleotides 58 to 237 of SEQ ID NO: 1 based on the SignalP3.0 program that predicts nucleotides 1 to 57 of SEQ ID NO: 1 encode a signal peptide.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Homologous sequence: The term "homologous sequence" is defined herein as a predicted protein that gives an E value (or expectancy score) of less than 0.001 in a tfasty search (Pearson, W. R., 1999, in *Bioinformatics Methods and Protocols*, S. Misener and S. A. Krawetz, ed., pp. 185-219) with the *Aspergillus oryzae* ZY082808 polypeptide of SEQ ID NO: 2.

Polypeptide fragment: The term "polypeptide fragment" is defined herein as a polypeptide having one or more (several) amino acids deleted from the amino and/or carboxyl terminus of the mature polypeptide of SEQ ID NO: 2; wherein the fragment has retained its activity.

Subsequence: The term "subsequence" is defined herein as a nucleotide sequence having one or more (several) nucleotides deleted from the 5' and/or 3' end of the mature polypeptide coding sequence of SEQ ID NO: 1; wherein the subsequence encodes a polypeptide fragment having retained its activity.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic, or recombinant nucleotide sequence.

cDNA: The term "cDNA" is defined herein as a DNA molecule that can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

Modification: The term "modification" means herein any chemical modification of the polypeptide consisting of the mature polypeptide of SEQ ID NO: 2; or a homologous sequence thereof; as well as genetic manipulation of the DNA encoding such a polypeptide. The modification can be a substitution, a deletion and/or an insertion of one or more (several) amino acids as well as replacements of one or more (several) amino acid side chains.

DETAILED DESCRIPTION OF THE INVENTION

When fungi are used as expression host cells for the production of proteins the protein of interest should be produced in a sufficient amount. As discussed briefly above in order to improve yield of such proteins several factors have traditionally been studied. Host cells used in the production of such proteins, which could e.g. be a heterologous protein expressed recombinantly in the host or an endogenous protein produced in high quantities, will be in a stress situation (Rutkowski, D. T., and Kaufman, R. J. (2004), "A trip to the ER: coping with stress", Trends in Cell Biology 14 (1): 20-28). In the present invention expression yield have been improved by affecting the expression of specific factors the expression of which seems to be influenced by the level of stress the host cell is subjected to. Such factors have been identified using a cDNA library of *A. oryzae* expressed sequence tags (ESTs) in a DNA array. A number of genes were differentially regulated and among these the polypeptide according to the present invention.

Polypeptides of the Invention

In a first aspect, the present invention relates to isolated polypeptides comprising an amino acid sequence having a degree of identity to the mature polypeptide of SEQ ID NO: 2 of preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% (hereinafter "homologous polypeptides"). In a preferred aspect, the homologous polypeptides have an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NO: 2.

A polypeptide of the present invention preferably comprises the amino acid sequence of SEQ ID NO: 2 or an allelic variant thereof; or a fragment thereof. In a preferred aspect, the polypeptide comprises the amino acid sequence of SEQ ID NO: 2. In another preferred aspect, the polypeptide comprises the mature polypeptide of SEQ ID NO: 2. In another preferred aspect, the polypeptide comprises amino acids 20 to 79 of SEQ ID NO: 2, or an allelic variant thereof; or a fragment thereof. In another preferred aspect, the polypeptide comprises amino acids 20 to 79 of SEQ ID NO: 2. In another preferred aspect, the polypeptide consists of the amino acid sequence of SEQ ID NO: 2 or an allelic variant thereof; or a fragment thereof. In another preferred aspect, the polypeptide consists of the amino acid sequence of SEQ ID NO: 2. In another preferred aspect, the polypeptide consists of the mature polypeptide of SEQ ID NO: 2. In another preferred aspect, the polypeptide consists of amino acids 20 to 79 of SEQ ID NO: 2 or an allelic variant thereof; or a fragment thereof. In another preferred aspect, the polypeptide consists of amino acids 20 to 79 of SEQ ID NO: 2.

In a second aspect, the present invention relates to isolated polypeptides that are encoded by polynucleotides that hybridize under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) the cDNA sequence contained in SEQ ID NO: 1, (iii) a subsequence of (i) or (ii), or (iv) a full-length complementary strand of (i), (ii), or (iii) (J. Sambrook, E. F. Fritsch, and T. Maniatis, 1989, *Molecular Cloning, A Laboratory Manual*, 2d edition, Cold Spring Harbor, N.Y.). A subsequence of the mature polypeptide coding sequence of SEQ ID NO: 1 contains at least 100 contiguous nucleotides or preferably at least 200 contiguous nucleotides. In a preferred aspect, the complementary strand is the full-length complementary strand of the mature polypeptide coding sequence of SEQ ID NO: 1.

The nucleotide sequence of SEQ ID NO: 1; or a subsequence thereof; as well as the amino acid sequence of SEQ ID NO: 2; or a fragment thereof; may be used to design nucleic acid probes to identify and clone DNA encoding polypeptides from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may, therefore, be screened for DNA that hybridizes with the probes described above and encodes a functionally homologous polypeptide. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1; or a subsequence thereof; the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 1; the cDNA sequence contained in SEQ ID NO: 1; its full-length complementary strand; or a subsequence thereof; under very low to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NO: 1. In another preferred aspect, the nucleic acid probe is nucleotides 58 to 237 of SEQ ID NO: 1. In another preferred aspect, the nucleic acid probe is a polynucleotide sequence that encodes the polypeptide of SEQ ID NO: 2, or a subsequence thereof. In another preferred aspect, the nucleic acid probe is SEQ ID NO: 1.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 45° C. (very low stringency), more preferably at 50° C. (low stringency), more preferably at 55° C. (medium stringency), more preferably at 60° C. (medium-high stringency), even more preferably at 65° C. (high stringency), and most preferably at 70° C. (very high stringency).

For short probes that are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes that are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to isolated polypeptides encoded by polynucleotides comprising or consisting of nucleotide sequences that have a degree of identity to the mature polypeptide coding sequence of SEQ ID NO: 1 of preferably at least 65%, more preferably at least 70%, more preferably at least 75%, more preferably at least 80%, more preferably at least 85%, even more preferably at least 90%, most preferably at least 95%, and even most preferably 96%, 97%, 98%, or 99%, which encode an active polypeptide. See polynucleotide section herein.

In another aspect, the the isolated polypeptides comprise the following motif:
EXXCGXXGXMXXDPXXLPEGVXXXXXRXCA,
wherein x is any amino acid. In the above motif, the accepted IUPAC single letter amino acid abbreviation is employed.

In a still further aspect, the present invention relates to artificial variants comprising a substitution, deletion, and/or insertion of one or more (or several) amino acids of the mature polypeptide of SEQ ID NO: 2; or a homologous polypeptide thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, LeuNal, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223, 409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO: 2, such as amino acids 20 to 79 of SEQ ID NO: 2, is 10, preferably 9, more preferably 8, more preferably 7, more preferably at most 6, more preferably 5, more preferably 4, even more preferably 3, most preferably 2, and even most preferably 1.

Sources of Polypeptides

A polypeptide of the present invention may be obtained from microorganisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide of the present invention the expression of which commits the host cell to apoptosis may be a fungal polypeptide, and more preferably a yeast polypeptide such as a *Candida*, *Kluyveromyces*, *Pichia*, *Saccharomyces*, *Schizosaccharomyces*, or *Yarrowia* polypeptide; or more preferably a filamentous fungal polypeptide such as an *Acremonium*, *Agaricus*, *Alternaria*, *Aspergillus*, *Aureobasidium*, *Botryospaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *lrpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* polypeptide.

In a preferred aspect, the polypeptide is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* polypeptide.

In another preferred aspect, the polypeptide is an *Acremonium cellulolyticus*, *Aspergillus aculeatus*, *Aspergillus awamori*, *Aspergillus fumigatus*, *Aspergillus foetidus*, *Aspergillus japonicus*, *Aspergillus nidulans*, *Aspergillus niger*, *Aspergillus oryzae*, *Chrysosporium keratinophilum*, *Chrysosporium lucknowense*, *Chrysosporium tropicum*, *Chrysosporium merdarium*, *Chrysosporium inops*, *Chrysosporium pannicola*, *Chrysosporium queenslandicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora crassa*, *Penicillium funiculosum*, *Penicillium purpurogenum*, *Phanerochaete chrysosporium*, *Thielavia achromatica*, *Thielavia albomyces*, *Thielavia albopilosa*, *Thielavia australeinsis*, *Thielavia fimeti*, *Thielavia microspora*, *Thielavia ovispora*, *Thielavia peruviana*, *Thielavia spededonium*, *Thielavia setosa*, *Thielavia subthermophila*, *Thielavia terrestris*, *Trichoderma harzianum*, *Trichoderma koningii*, *Trichoderma longibrachiatum*, *Trichoderma reesei*, or *Trichoderma viride* polypeptide.

In another preferred aspect, the polypeptide is an *Aspergillus oryzae*, *Aspergillus niger*, polypeptide.

In a more preferred aspect, the polypeptide is an *Aspergillus oryzae* polypeptide. In a most preferred aspect, the polypeptide is an *Aspergillus oryzae* A1560 (NBRC4177) polypeptide, e.g., the polypeptide comprising the mature polypeptide of SEQ ID NO: 2.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL).

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques that are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide of the invention from the fusion protein. Examples of cleavage sites include, but are not limited to, a Kex2 site that encodes the dipeptide Lys-Arg (Martin et al., 2003, *J. Ind. Microbiol. Biotechnol.* 3: 568-76; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381), an Ile-(Glu or Asp)-Gly-Arg site, which is cleaved by a Factor Xa protease after the arginine residue (Eaton et al., 1986, *Biochem.* 25: 505-512); a Asp-Asp-Asp-Asp-Lys site, which is cleaved by an enterokinase after the lysine (Collins-Racie et al., 1995, *Biotechnology* 13: 982-987); a His-Tyr-Glu site or His-Tyr-Asp site, which is cleaved by Genenase I (Carter et al., 1989, *Proteins: Structure, Function, and Genetics* 6: 240-248); a Leu-Val-Pro-Arg-Gly-Ser site, which is cleaved by thrombin after the Arg (Stevens, 2003, *Drug Discovery World* 4: 35-48); a Glu-Asn-Leu-Tyr-Phe-Gln-Gly site, which is cleaved by TEV protease after the Gln (Stevens, 2003, supra); and a Leu-Glu-Val-Leu-Phe-Gln-Gly-Pro site, which is cleaved by a genetically engineered form of human rhinovirus 3C protease after the Gln (Stevens, 2003, supra).

Polynucleotides

The present invention also relates to isolated polynucleotides comprising or consisting of nucleotide sequences that encode polypeptides the expression of which commits the host cell to apoptosis of the present invention.

In a preferred aspect, the nucleotide sequence comprises or consists of SEQ ID NO: 1. In another preferred aspect, the nucleotide sequence comprises or consists of the mature polypeptide coding sequence of SEQ ID NO: 1. In another preferred aspect, the nucleotide sequence comprises or consists of nucleotides 58 to 237 of SEQ ID NO: 1. The present invention also encompasses nucleotide sequences that encode polypeptides comprising or consisting of the amino acid sequence of SEQ ID NO: 2 or the mature polypeptide thereof, which differ from SEQ ID NO: 1 or the mature polypeptide coding sequence thereof by virtue of the degeneracy of the genetic code. The present invention also relates to subsequences of SEQ ID NO: 1 that encode fragments of SEQ ID NO: 2.

The present invention also relates to mutant polynucleotides comprising or consisting of at least one mutation in the mature polypeptide coding sequence of SEQ ID NO: 1, in which the mutant nucleotide sequence encodes the mature polypeptide of SEQ ID NO: 2.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from a strain of *Aspergillus*, or another or related organism and thus, for example, may be an allelic or species variant of the polypeptide encoding region of the nucleotide sequence.

The present invention also relates to isolated polynucleotides comprising or consisting of nucleotide sequences that have a degree of identity to the mature polypeptide coding sequence of SEQ ID NO: 1 of preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the mature polypeptide coding sequence of SEQ ID NO: 1, e.g., a subsequence thereof, and/or by introduction of nucleotide substitutions that do not give rise to another amino acid sequence of the polypeptide encoded by the nucleotide sequence, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for maintained activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra; Smith et al., 1992, supra; Wlodaver et al., 1992, supra).

The present invention also relates to isolated polynucleotides encoding polypeptides of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) the cDNA sequence contained in SEQ ID NO: 1, or (iii) a full-length complementary strand of (i) or (ii); or allelic variants and subsequences thereof (Sambrook et al., 1989, supra), as defined herein. In a preferred aspect, the complementary strand is the full-length complementary strand of the mature polypeptide coding sequence of SEQ ID NO: 1.

The present invention also relates to isolated polynucleotides obtained by (a) hybridizing a population of DNA under very low, low, medium, medium-high, high, or very high stringency conditions with (i) the mature polypeptide coding sequence of SEQ ID NO: 1, (ii) the cDNA sequence contained SEQ ID NO: 1, or (iii) a full-length complementary strand of (i) or (ii); and (b) isolating the hybridizing polynucleotide, which encodes a polypeptide the expression of which commits the host cell to apoptosis. In a preferred aspect, the complementary strand is the full-length complementary strand of the mature polypeptide coding sequence of SEQ ID NO: 1.

Nucleic Acid Constructs

The present invention also relates to nucleic acid constructs comprising an isolated polynucleotide of the present invention operably linked to one or more (several) control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and Aspergillus nidulans triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence; a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding sequence that codes for an amino acid sequence linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

In one embodiment the signal peptide is the normal signal associated with the polypeptide of the invention.

In one aspect, the signal peptide comprises or consists of amino acids 1 to 19 of SEQ ID NO: 2. In another aspect, the signal peptide coding sequence comprises or consists of nucleotides 1 to 57 of SEQ ID NO: 1.

The control sequence may also be a propeptide coding sequence that codes for an amino acid sequence positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, xyl and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bargene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising an isolated polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred aspect, the yeast host cell is a *Candida*, *Hansenula*, *Kluyveromyces*, *Pichia*, *Saccharomyces*, *Schizosaccharomyces*, or *Yarrowia* cell.

In a most preferred aspect, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

In a most preferred aspect, the filamentous fungal host cell is an *Aspergillus awamori*, *Aspergillus fumigatus*, *Aspergillus foetidus*, *Aspergillus japonicus*, *Aspergillus nidulans*, *Aspergillus niger* or *Aspergillus oryzae* cell. In another most preferred aspect, the filamentous fungal host cell is a *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, or *Fusarium venenatum* cell. In another most preferred aspect, the filamentous fungal host cell is a *Bjerkandera adusta*, *Ceriporiopsis aneirina*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium keratinophilum*, *Chrysosporium lucknowense*, *Chrysosporium tropicum*, *Chrysosporium merdarium*, *Chrysosporium inops*, *Chrysosporium pannicola*, *Chrysosporium queenslandicum*, *Chrysosporium zonatum*, *Coprinus cinereus*, *Coriolus hirsutus*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Aspergillus*. In a more preferred aspect, the cell is *Aspergillus oryzae*.

The present invention also relates to methods of producing a polypeptide of the present invention, comprising: (a) cultivating a recombinant host cell, as described herein, under conditions conducive for production of the polypeptide; and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Removal or Reduction of ZY082808 Activity

The present invention also relates to a mutant of a parent cell, which comprises modifying, disrupting or deleting a polynucleotide sequence, or a portion thereof, encoding a polypeptide of the present invention, which results in the mutant cell producing less of the polypeptide than the parent cell when cultivated under the same conditions.

The mutant cell may be constructed by reducing or eliminating expression of a nucleotide sequence encoding a polypeptide of the present invention using methods well known in the art, for example, insertions, disruptions, replacements, or deletions. In a preferred aspect, the nucleotide sequence is modified so that the encoded polypeptide is inactivated. The nucleotide sequence to be modified may be, for example, the coding region or a part thereof essential for activity, or a regulatory element required for the expression of the coding region. An example of such a regulatory or control sequence may be a promoter sequence or a functional part thereof, i.e., a part that is sufficient for affecting expression of the nucleotide sequence. Other control sequences for possible modification include, but are not limited to, a leader, polyadenylation sequence, propeptide sequence, signal peptide sequence, transcription terminator, and transcriptional activator.

Thus in one embodiment the present invention relates to a mutant fungal host, wherein the mutant has a reduced or no expression of an endogenous polypeptide selected from the group consisiting of:

(a) a polypeptide comprising an amino acid sequence having at least 66%, more preferably at least 70%, more preferably at least 75%, more preferably at least 80%, even more preferably at least 85%, most preferably at least 90%, and even most preferably at least 95% identity to the mature polypeptide of SEQ ID NO: 2;

(b) a polypeptide encoded by a polynucleotide that hybridizes under at least medium stringency conditions, even more preferably at least medium-high stringency conditions, and most preferably at least high stringency conditions with (i) the mature polypeptide coding sequence of SEQ ID NO: 1, (ii) cDNA sequence contained in the DNA sequence comprising the mature polypeptide coding sequence of SEQ ID NO: 1, or (iii) a full-length complementary strand of (i) or (ii);

(c) a polypeptide encoded by a polynucleotide comprising a nucleotide sequence having [Edit accordingly] preferably at least 60%, more preferably at least 65%, more preferably at least 70%, more preferably at least 75%, more preferably at least 80%, even more preferably at least 85%, most preferably at least 90%, and even most preferably at least 95% identity to the mature polypeptide coding sequence of SEQ ID NO: 1;

(d) a polypeptide induced during apoptosis and comprising the motif: EXXCGXXGXMXXDPXX-LPEGVXXXXXRXCA; and (e) a variant comprising a substitution, deletion, and/or insertion of one or several amino acids of the mature polypeptide of SEQ ID NO: 2.

In one further embodiment the endogenous polypeptide of the invention, the activity of which is reduced or eliminated in the mutant host, comprises the amino acid sequence of SEQ ID NO: 2 or an allelic variant thereof; or a fragment thereof. In a preferred aspect, the polypeptide comprises the amino acid sequence of SEQ ID NO: 2. In another preferred aspect, the polypeptide comprises the mature polypeptide of SEQ ID NO: 2. In another preferred aspect, the polypeptide comprises amino acids 20 to 79 of SEQ ID NO: 2, or an allelic variant thereof; or a fragment thereof. In another preferred aspect, the polypeptide comprises amino acids 20 to 79 of SEQ ID NO: 2. In another preferred aspect, the polypeptide consists of the amino acid sequence of SEQ ID NO: 2 or an allelic variant thereof; or a fragment thereof. In another preferred aspect, the polypeptide consists of the amino acid sequence of SEQ ID NO: 2. In another preferred aspect, the polypeptide consists of the mature polypeptide of SEQ ID NO: 2. In another preferred aspect, the polypeptide consists of amino acids 20 to 79 of SEQ ID NO: 2 or an allelic variant thereof; or a fragment thereof. In another preferred aspect, the polypeptide consists of amino acids 20 to 79 of SEQ ID NO: 2.

In a preferred aspect the mutant host cell is a filamentous fungal cell or a yeast cell. In a more preferred aspect the filamentous fungal host is selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

Preferably the *Aspergillus* cell is selected from *Aspergillus awamori, Aspergillus fumigatus, Aspergillus foetidus, Aspergillus japonicus, Aspergillus nidulans, Aspergillus niger* or *Aspergillus oryzae*.

In another preferred embodiment the mutant filamentous fungal cell is an *Aspergillus oryzae* cell or an *Aspergillus niger* cell.

Modification or inactivation of the nucleotide sequence may be performed by subjecting the parent cell to mutagenesis and selecting for mutant cells in which expression of the nucleotide sequence has been reduced or eliminated. The mutagenesis, which may be specific or random, may be performed, for example, by use of a suitable physical or chemical mutagenizing agent, by use of a suitable oligonucleotide, or by subjecting the DNA sequence to PCR generated mutagenesis. Furthermore, the mutagenesis may be performed by use of any combination of these mutagenizing agents.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and screening and/or selecting for mutant cells exhibiting reduced or no expression of the gene.

Modification of the nucleotide sequence may be accomplished by introduction, substitution, or removal of one or more (several) nucleotides in the gene or a regulatory element required for the transcription or translation thereof. For example, nucleotides may be inserted or removed so as to result in the introduction of a stop codon, the removal of the start codon, or a change in the open reading frame. Such modification or inactivation may be accomplished by site-directed mutagenesis or PCR generated mutagenesis in accordance with methods known in the art. Although, in principle, the modification may be performed in vivo, i.e., directly on the cell expressing the nucleotide sequence to be modified, it is preferred that the modification be performed in vitro as exemplified below.

An example of a convenient way to eliminate or reduce expression of a nucleotide sequence by a cell is based on techniques of gene replacement, gene deletion, or gene disruption. For example, in the gene disruption method, a nucleic acid sequence corresponding to the endogenous nucleotide sequence is mutagenized in vitro to produce a defective nucleic acid sequence that is then transformed into the parent cell to produce a defective gene. By homologous recombination, the defective nucleic acid sequence replaces the endogenous nucleotide sequence. It may be desirable that the defective nucleotide sequence also encodes a marker that may be used for selection of transformants in which the nucleotide sequence has been modified or destroyed. In a particularly preferred aspect, the nucleotide sequence is disrupted with a selectable marker such as those described herein.

Alternatively, modification or inactivation of the nucleotide sequence may be performed by established anti-sense or RNAi techniques using a sequence complementary to the nucleotide sequence. More specifically, expression of the nucleotide sequence by a cell may be reduced or eliminated by introducing a sequence complementary to the nucleotide sequence of the gene that may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

The present invention further relates to a mutant cell of a parent cell that comprises a disruption or deletion of a nucleotide sequence encoding the polypeptide or a control sequence thereof, which results in the mutant cell producing less of the polypeptide or no polypeptide compared to the parent cell.

The polypeptide-deficient mutant cells so created are particularly useful as host cells for the expression of native and/or heterologous polypeptides. Therefore, the present invention further relates to a mutant cell according to the invention further comprising a gene encoding a native or heterologous protein and to methods of producing a native or heterologous polypeptide comprising: (a) cultivating the mutant cell under conditions conducive for production of the native or heterologous polypeptide; and (b) recovering the polypeptide. The term "heterologous polypeptides" is defined herein as polypeptides that are not native to the host cell, a native protein in which modifications have been made to alter the native sequence, or a native protein whose expression is quantitatively altered as a result of a manipulation of the host cell by recombinant DNA techniques.

In a further aspect, the present invention relates to a method of producing a protein of interest comprising: (a) cultivating a mutant cell under conditions conducive for production of the protein wherein the mutant has a reduced or no expression of an endogenous polypeptide compared to a parent host cell grown under the same conditions, and wherein the expression of said endogenous polypeptide commits the cell to apoptosis; and optionally (b) recovering the protein of interest.

In an even further aspect the present invention relates to a method of producing a protein of interest, comprising: (a) cultivating the mutant cell having a reduced or no activity of the polypeptide of the invention under conditions conducive for production of the protein; and (b) recovering the protein. Particularly the protein is a heterologous protein.

The methods used for cultivation and purification of the product of interest may be performed by methods known in the art.

The methods of the present invention for producing a protein product are of particular interest in the production of eukaryotic polypeptides, in particular fungal proteins such as enzymes. The enzyme may be selected from, e.g., an amylolytic enzyme, lipolytic enzyme, proteolytic enzyme, cellulytic enzyme, oxidoreductase, or plant cell-wall degrading enzyme. Examples of such enzymes include an aminopeptidase, amylase, amyloglucosidase, carbohydrase, carboxypeptidase, catalase, cellobiohydrolase, cellulase, chitinase, cutinase, cyclodextrin glycosyltransferase, deoxyribonuclease, endoglucanase, esterase, galactosidase, beta-galactosidase, glucoamylase, glucose oxidase, glucosidase, haloperoxidase, hemicellulase, invertase, isomerase, laccase, ligase, lipase, lyase, mannosidase, oxidase, pectinolytic enzyme, peroxidase, phytase, phenoloxidase, polyphenoloxidase, proteolytic enzyme, ribonuclease, transferase, transglutaminase, or xylanase. The mutant cells may also be used to express heterologous proteins of pharmaceutical interest such as hormones, growth factors, receptors, and the like.

It will be understood that the term "eukaryotic polypeptides" includes not only native polypeptides, but also those polypeptides, e.g., enzymes, which have been modified by amino acid substitutions, deletions or additions, or other such modifications to enhance activity, thermostability, pH tolerance and the like.

Methods of Inhibiting Expression of a Polypeptide

In the production method according to the invention the reduction or elimination of the polypeptide according to the invention is particularly achieved by random mutation, site specific mutation, deletion, or by inhibiting the expression by administering a double-stranded RNA (dsRNA) molecule, wherein the dsRNA comprises a subsequence of a polynucleotide of the present invention. In a preferred aspect, the dsRNA is about 15, 16, 17, 18, 19, 20, 21, 22, 23, 24, 25 or more duplex nucleotides in length.

The dsRNA is preferably a small interfering RNA (siRNA) or a micro RNA (miRNA). In a preferred aspect, the dsRNA is small interfering RNA (siRNAs) for inhibiting transcription. In another preferred aspect, the dsRNA is micro RNA (miRNAs) for inhibiting translation.

The present invention also relates to such double-stranded RNA (dsRNA) molecules, comprising a portion of the mature polypeptide coding sequence of SEQ ID NO: 1 for inhibiting expression of a polypeptide in a cell. While the present invention is not limited by any particular mechanism of action, the dsRNA can enter a cell and cause the degradation of a single-stranded RNA (ssRNA) of similar or identical sequences, including endogenous mRNAs. When a cell is exposed to dsRNA, mRNA from the homologous gene is selectively degraded by a process called RNA interference (RNAi).

Methods for making and using dsRNA molecules to selectively degrade RNA are well known in the art, see, for example, U.S. Pat. No. 6,506,559; U.S. Pat. No. 6,511,824; U.S. Pat. No. 6,515,109; and U.S. Pat. No. 6,489,127.

The present invention is further described by the following examples that should not be construed as limiting the scope of the invention.

EXAMPLES

Chemicals used as buffers and substrates were commercial products of at least reagent grade.
Plasmids
pDV8 is described in patent WO2001068864, example 8.
pJaL410 is described in patent WO2003008575, example 8.
pJaL419 is described in patent WO2003008575, example 8.
pJaL504 is described in example 1 and SEQ ID NO: 14.
pJaL554 is described in patent WO2001068864, example 8.
pJaL575 is described in example 1 and SEQ ID NO: 15.
pJaL729 is described in patent WO2003008575, example 12.
pJaL731 is described in example 1 and SEQ ID NO: 16.
pJaL736 is described in example 1 and SEQ ID NO: 17.
pJAL958 is described in example 1 and SEQ ID NO: 18.
pMT2786 is described in example 2 and SEQ ID NO: 19.
pMT3155 is described in example 2 and SEQ ID NO: 20.
pMT3296 is described in example 2 and SEQ ID NO: 21.
pMT3306 is described in example 2 and SEQ ID NO: 22.
pMT3328 is described in example 3 and SEQ ID NO: 23.
pMT3330 is described in example 3 and SEQ ID NO: 24.
pMT3332 is described in example 3 and SEQ ID NO: 25.
pMT3369 is described in example 4 and SEQ ID NO: 26.
pMT3376 is described in example 4 and SEQ ID NO: 27.
pMT3378 is described in example 4 and SEQ ID NO: 28.
pMT3431 is described in example 4 and SEQ ID NO: 29.
Strains
ToC1512 is described in patent WO2005070962, example 11.
JaL507 is described in example 1.
BECh2 is described in WO 00/39322, example 1, which is further referring to JaL228 described in WO 98/12300, example 1.

Example 1

Identification of the ZY082808 Transcript

Construction of a Lipase Producing Strain of *Aspergillus Oryzae*
Construction of the *Aspergillus Oryzae* niaD Deletion Plasmid pJaL736

The single restriction endonuclease sites BamHI and BglII in pDV8 were removed by two succeeding rounds of cutting with each of the restriction endonucleases and the free overhang-ends was filled in by treatment with Klenow polymerase and the four deoxyribonucleotides and ligated resulting in plasmid pJaL504 (SEQ ID NO: 14).

From pJaL504 a 2514 bp fragment were amplified by PCR with primer 172450 and 172449 (SEQ ID NO: 3 and 4) and cloned into the vector pCR®4Blunt-TOPO resulting in plasmid pJaL575 (SEQ ID NO: 15).

The repeat flanked pyrG selection marker from pJaL554 was moved as a 1998 bp Asp718-HindIII fragment where the ends were completely filled in by treating with dNTP's and klenow polymerase. The fragment was cloned into completely filled in BssHII-Asp718 site of pJaL419 resulting in plasmid pJaL731 (SEQ ID NO: 16). The pyrG gene thereby replaces a 2200 bp fragment encoding the 3' part of the niaD gene and the pyrG gene is then flanked by a 772 bp fragment of the 5' end of niaD and a 698 bp fragment of the 3' end of niaD. Finally, the deletion cassette of pJaL731 containing the two niaD flanks on either side of the pyrG selection marker was transferred as a 3500 bp HindIII fragment into the HindIII site of the tk counter selectable plasmid pJaL575 to give the deletion plasmid pJaL736 (SEQ ID NO: 17). Note that pJaL736 contains a unique NotI site, which were used to linearize the plasmid prior to transformation into *A. oryzae*.
Construction of niaD Deleted *A. Oryzae* Strain, JaL507.

20 microgram of pJaL736 was cut with NotI and subsequently the enzyme was heat inactivated as recommended by the manufacturer (New England Biolabs). The plasmid was then ethanol precipitated and re-dissolved in Tris buffer (10 mM pH 8.0) at a concentration suitable for transformation into *Aspergillus oryzae*.

The linearized plasmid DNA was transformed into *Aspergillus oryzae* ToC1512 with selection for pyrG and counter selection of the tk gene on FDU plates as previously described in WO 0168864. Transformants were re-isolated twice and finally grown up in liquid medium (YPD). Transformants were tested for there ability to grow on nitrate as the sole nitrogen source. Chromosomal DNA was prepared as previously described in WO 0168864 form transformants that were not able to grow on nitrate which indicate that the niaD gene was disrupted and used for Southern analysis of the niaD locus with the aim to identify transformants in which a clean double cross-over between the chromosomal niaD and the deletion cassette had occurred. The chromosomal DNA was digested with BamHI. The Southern blot was first probed with the whole niaD gene excised as a 3430 bp HindIII fragment from pJaL410. For the intact niaD locus, two bands of 2838 bp and 1820 bp respectively was appearing using this probe, while the niaD deleted derivative originating from the desired double cross-over resulted in a 4567 bp band. The Southern was stripped of the first probe and re-probed with a probe excised as a 2059 bp Asp718 fragment of pJaL410. For the intact niaD locus a 2838 bp and a 1820 bp BamHI band were appearing, while for the niaD deletion strain originating from the desired cross over no hybridization bands was obtained. A strain with the above characteristics was preserved as *A. oryzae* strain JaL507.
Construction of pJaL958

A variant of the *Humicola lanuginosa* lipase was cloned as a 901 bp BamHI-SalI obtained from digestion of p960 (described in EP0305216 example 1 and FIG. 4) into pJaL729 digested with BamHI-XhoI resulting in pJaL958 (SEQ ID NO: 18).
Construction of *A. Oryzae* Strain JaL731

Plasmid pJaL958 was transformed into *A. oryzae* strain JaL507 and transformants were screened for lipase activity as described in WO2003008575, example 13-15. Among the transformants one displaying high lipase activity was selected and named JaL731.

Primer 172450 (SEQ ID NO: 3)
5'-GACGAATTCTCTAGAAGATCTCTCGAGGAGCTCAAGCTTCTGTA-CAGTGACCGGTGACTC Primer 172449 (SEQ ID NO: 4)
5'-GACGAATTCCGATGAATGTGTGTCCTG Spores of JaL731 were subjected to mutagenesis using nitrosoguanidine (as described in Araujo, Ward and D'Souza. (1991). Biotechnology Techniques 5 (4): 283-288. Use of mutation strategies applied to *Aspergillus terreus* ATCC 52430 to obtain mutants with improved cellulase productivity). Mutants were screened for increased lipase expression in microtiter plates by using robotics, and a high yielding mutant, named 5-58, was selected. Lipase activity was measured as described by Haack et al., 2006 (Change in hyphal morphology of *Aspergillus oryzae* during fed-batch cultivation. Appl Microbiol Biotechnol 70: 482-487).

The two lipase producing strains, JaL731 and its high yield mutant 5-58, were compared by transcriptomic analysis of gene expression by using DNA microarray technique (Baldi and Hatfield, 2002 (DNA Microarrays and Gene Expression, Cambridge University Press, Cambridge); Knudsen, 2002 (A Biologist's Guide to Analysis of DNA microarray data. Wiley & sons, New York).

Spotted slides based on an inhouse cDNA library of *A. oryzae* expressed sequence tags were used. mRNA was extracted by the PolyATract® System 1000 (Promega Corporation, Madison, Wis.), starting with 1 g of cell material. cDNA synthesis and Cy3 and Cy5 labelling were performed with the aid of the CyScribe Post labelling Kit with CyScribe GFX purification kit (Amersham Biosciences, HiHerod, Denmark). Hybridization was performed using standard methods. Scanning of the slides was performed using a GMS 418 array scanner (Genetic MicroSystems Inc., Woburn, Mass.). The scanning images were quantified by using the ImaGene™ 5 Software (Biodiscovery Inc., Marina Del Rey, Calif., USA). Statistical analysis of differential expression was performed using Genesight Software (Biodiscovery Inc., Marina Del Rey, Calif., USA).

Laboratory tank fermentation was carried out for each of the two strains JaL731 and 5-58, and sampling of biomass was done at two time points. Eight successful hybridizations were carried out between the two strains. The transcriptomic analysis showed differential regulation of the transcript ZY082808. In the high yield mutant, 5-58, the ZY082808 transcript was down-regulated in.

A number of genes were differentially regulated. However, also microarray data from analyses of other *A. oryzae* lipase strain pairs suggested ZY082808 as an interesting gene for follow up. Thus, gene expression of a high producing recombinant lipase strain Amsp173-40a was compared to an analogous lower producing recombinant lipase strain Amsp165-28a by using the DNA microarray technique. The strain Amsp173-40a is described by Haack et al. (2006) supra. Amsp165-28a was constructed in the same way as Amsp173-40a and selected as a low producing strain by test in laboratory tank fermentation. For Amsp173-40a increased swelling of the hyphal tip was observed in the fed batch phase with high lipase productivity and assumed secretion stress conditions as described and discussed by Haack et al. (2006) supra. For Amsp165-28a no swelling of the hyphal tip was observed. The transcriptomic analysis showed differential regulation of ZY082808 also in these strains, and ZY082808 was up-regulated in Amsp173-40a in a number of independent array experiments as shown in table 1. The reverse regulation of ZY082808 in the two different strain pairs suggested ZY082808 as a particular interesting gene for follow up.

TABLE 1

| | Amsp173-40a ↔ Amsp165-28a Exp1 | | Amsp173-40a ↔ Amsp165-28a Exp. 2 | | Amsp173-40a ↔ Amsp165-28a Exp. 3 | | 5-58 ↔ JaL731 Exp. 4 | |
|---|---|---|---|---|---|---|---|---|
| | Fold Change | P value | Fold Change | P value | Fold Change | P value | Fold Change | P value |
| ZY 082808 | 2.8 | $7.7 \times 10^{-6}$ | 2.8 | $6.3 \times 10^{-5}$ | 3.2 | $4.9 \times 10^{-5}$ | −3.1 | < 0.001 |

Example 2

Expression Plasmids for Overexpression of the ZY082808 Encoded Peptide

Primers:

Primer 821 (SEQ ID NO: 5)
5'-TCTTGGTACCCTCAGCAAAGCCATCATTGC-3'

Primer 822 (SEQ ID NO: 6)
5'-TCTCTCTAGACTCCCTCTGGTT-TAATACTCCG-3'

Primer 829 (SEQ ID NO: 7)
5'-CATTTGGATCCACCATGAGACTCTCCC-3'

Primer 841 (SEQ ID NO: 8)
5'-TTCTCTCGAGCTAAGGAAACCACCTCGGC-3'

The *A. oryzae* chromosomal sequence encoding the ZY082808 transcript was PCR amplified from *A. oryzae* strain BECh2 using primers 821 and 822 (SEQ ID 5 and 6) to give a 2.0 kb fragment. This fragment was cut at the Asp718 and Xba1 sites introduced by the applification primers 821 and 822. The ZY082808 encoding Asp718-Xba1 fragment was inserted in the vector pMT3155 (SEQ ID NO: 20) which had been cut with BsiW1 and Bln1. The pMT3155 vector contains markers to allow for selection of leucine prototrophy in *E. coli* and for selecting resistance to the herbicide BASTA in *Aspergillus oryzae*. The resulting plasmid capable of directing expression of the ZY082808 encoded peptide from its own original promoter was named pMT3296 (SEQ ID NO: 21).

To construct a plasmid expressing the ZY082808 encoded peptide from a strong tandem NA2/TPI promoter described in WO 2003008575, the ZY082808 ORF was PCR amplified from pMT3296 using primers 829 and 841 (SEQ ID NO: 7 and 8) to give a 0.25 kb fragment.

This fragment was cut at the BamH1 and Xho1 sites introduced by the PCR primers, and inserted in the vector pMT2786 (SEQ ID NO: 19) (which is a modified version of pMT2188 described in WO 2006/050737 example 2; in pMT2786 the URA3 marker has been replaced with the *S. cerevisiae* LEU2 marker which can be selected for in *E. coli* leuB mutants (leucine requiring), and in addition there is an approximately 2 kb "stuffer" inserted in pMT2786 between the BamH1 and Xho1 used for cloning) cut with Bam and Xho. The pMT2786 vector contains markers to allow for selection of leucine prototrophy in *E. coli* and for selecting for ability to grow on acetamide as sole nitrogen source in *A. oryzae*. The resulting expression plasmid was named pMT3306 (SEQ ID NO: 22).

pMT3296 was transformed into *A. oryzae* mutant strain 5-58 selecting for resistance to BASTA. 12 transformants were isolated and subsequently re-isolated twice through sporulation. Likewise, pMT3306 was transformed into strain 5-58 selecting for the ability to grow on acetamide as sole nitrogen source. No transformants were obtained growing detectably better than the background untransformed *A. oryzae* strain. The transformation experiment was repeated but again no transformants could be isolated.

The 12 transformants as well as the strain 5-58 were inoculated on Cove-N agar slants and incubated for one week at 34° C. For all isolates 500 ml shake flasks with 2 baffles and with 100 ml G1-Gly substrate was inoculated with 5 ml spore suspension and incubated over night at 30° C., 250 rpm. The G1-Gly substrate contained 18 g/l yeast extract, 24 g/l glycerol 87%, 1 ml/l pluronic and 5 g/l CaCO$_3$. Tapwater was used. pH was adjusted to 7.0 before sterilization for 20 min at 121° C. From each G1-Gly shake flask 5 ml was transferred to two 500 ml shake flasks with 2 baffles and with 100 ml 1/5MDU2B substrate. The 1/5MDU2B substrate contained 9.0 g/l maltose, 0.2 g/l MgSO$_4$.7H$_2$O, 0.2 g/l NaCl, 0.4 g/l K$_2$SO$_4$, 2.4 g/l KH$_2$PO$_4$, 0.1 ml/l trace metal, 0.02 ml/l pluronic, and 1.4 g/l yeast extract. Tapwater was used. The trace metal solution contained 14.2 g/l ZnSO4.7H$_2$O, 2.5 g/l CuSO4.5H$_2$O, 0.5 g/l NiCl2.6H$_2$O, 13.8 g/l FeSO4.7H$_2$O, 8.5 g/l MnSO4.H$_2$O and 3.0 g/l citric acid H$_2$O. pH was adjusted to 5.0 before sterilization for 20 min at 121° C. After sterilization 0.2 ml 50% urea was added pr. 100 ml substrate. The 1/5MDU2B shake flasks were incubated at 34° C., 270 rpm. Every shake flask was sampled after 2 days. Samples were centrifuged for 10 min at 3000 rpm. Supernatants are frozen at −20° C. Samples were thawed and lipase activity (LU/ml) was measured by using standard protocol. Two independent shake flaks experiments were carried out.

Four out of twelve transformants had reproducibly 2-3 times reduced lipase expression compared to 5-58 as shown in table 2. This indicates a negative effect of over-expression of ZY082808 as suggested by transcriptomic analysis. It can be seen that for e.g. transformant 5-58pMT3296#3 an increased expression was observed, which could be due to some random variation, i.e. copy number increase of the lipase gene combined with low expression of ZY082808 in that particular transformant. The results should be compared to transformation by the vector alone. Twenty pMT3155-transformants were fermented by using the same protocol as for the 5-58pMT3296 transformants.

No significant negative effect on lipase expression was observed for the twenty transformants as shown in table 3. This confirms the suggested negative effect of ZY082808 overexpression from the data shown in table 2.

TABLE 2

| Strain | Experiment 1 Lipase expression in % of 5-58 | Experiment 2 lipase expression in % of 5-58 |
|---|---|---|
| 5-58pMT3296#1 | 126 | 109 |
| 5-58pMT3296#2 | 114 | 115 |
| 5-58pMT3296#3 | 138 | 140 |
| 5-58pMT3296#4 | 36 | 37 |
| 5-58pMT3296#5 | 27 | 33 |
| 5-58pMT3296#6 | 98 | 104 |
| 5-58pMT3296#7 | 33 | 38 |
| 5-58pMT3296#8 | 113 | 112 |
| 5-58pMT3296#9 | 144 | 119 |
| 5-58pMT3296#10 | 118 | 113 |
| 5-58pMT3296#11 | 93 | 87 |
| 5-58pMT3296#12 | 55 | 55 |
| 5-58 | 100 | 100 |

TABLE 3

| Strain | Experiment 1 lipase expression in % of 5-58 | Experiment 2 lipase expression in % of 5-58 |
|---|---|---|
| 5-58 | 100 | 100 |
| 5-58pmt3155#1 | 74 | 98 |
| 5-58pmt3155#2 | 83 | 76 |
| 5-58pmt3155#3 | 73 | 114 |
| 5-58pmt3155#4 | 52 | 112 |
| 5-58pmt3155#5 | 75 | 102 |
| 5-58pmt3155#6 | ND | 95 |
| 5-58pmt3155#7 | ND | 129 |
| 5-58pmt3155#8 | ND | 110 |
| 5-58pmt3155#9 | ND | 101 |
| 5-58pmt3155#10 | ND | ND |
| 5-58pmt3155#11 | ND | 96 |
| 5-58pmt3155#12 | ND | 106 |
| 5-58pmt3155#13 | ND | 124 |
| 5-58pmt3155#14 | ND | 126 |
| 5-58pmt3155#15 | 80 | 107 |
| 5-58pmt3155#16 | 94 | 102 |
| 5-58pmt3155#17 | 68 | 98 |
| 5-58pmt3155#18 | 70 | 104 |
| 5-58pmt3155#19 | 106 | 77 |
| 5-58pmt3155#20 | 78 | 105 |

Example 3

Construction of a Plasmid for Expression of a shRNA for ZY82808 Sequences

In order to have a visual marker by which to judge the degree of downregulation, a construct was made in which both ZY082808 and the wA gene needed for green spore development could be downregulated. Absence of the wA gene product leads to white spore color, and partial expression of the gene could be expected to lead to lighter shades of green than wt spore color.

Primers:

```
Primer 798
                                    (SEQ ID NO: 9)
5'-TCTTGGATCCGTCGACCTTGGGGAAGTCATCACCG-3'

Primer 868
                                    (SEQ ID NO: 10)
5'-GTCATTAATCATTGAATTCTCGTCGCGACTCTC-3'
```

-continued

Primer 865
(SEQ ID NO: 11)
5'-GTCGCGACGAGAATTCAATGATTAATGACCTTTTC-
CTAAATATAC-3'

Primer 867
(SEQ ID NO: 12)
5'-TCTTCTCGAGCCTAGGTATCCCAAAGTCAA-
GTACGTCAGG-3'

Primer 866
(SEQ ID NO: 13)
5'-TCTTCTCGAGCCTAGGCTCTCCCTCAACCTTCTACTG-3'

A fusion of the sequences encoding part of the wA (whiteA) product (Thomas et al., 1998, Microbiol and Mol Biol Reviews, 62(1): 35-54) and the ZY082808 sequence including part of the 5'UTR was made by SOE PCR: The wA sequences were amplified from *A. oryzae* strain BECh2 DNA using primers 798 and 868 (SEQ ID NO: 9 and 10, respectively) and fused to ZY082808 sequences amplified by primers 865 and 867 (SEQ ID NO: 11 and 12) from pMT3296 template. The SOE fusion product was cut by BamH1 and Xho1 at the sites introduced by primers 798 and 867, respectively. The resulting approx. 1.2 kb fragment was ligated into BamH1-Xho1 cut vector pMT2786 to give plasmid pMT3328 (SEQ ID NO: 23).

A similar fusion of wA to a shorter piece of ZY082808 sequence (lacking 5'UTR) was made by fusing the wA fragment amplified by primers 798 and 868 to the ZY082808 sequence amplified by primers 865 and 866 (SEQ ID NO: 11 and SEQ ID NO: 13). The resulting approx. 1.0 kb fragment was cut by BamH1 and Xho1 at the sites introduced by primers 798 and 866, respectively. The Bam-Xho fragment was inserted in BamH1-Xho1 cut vector pMT2786 to give plasmid pMT3330 (SEQ ID NO: 24). Finally the Asp718-Xho1 (5.5 kb) and the Asp718-Bln1 (2.5 kb) fragments of pMT3328 were ligated to the Bln1-SalI (1.0 kb) fragment to give plasmid pMT3332 (SEQ ID NO: 25). pMT3332 can be selected in *Aspergillus oryzae* by the ability to grow on acetamide as the sole source of nitrogen. pMT3332 is constructed such that the strong NA2/TPI promoter drives the transcription of a shRNA containing sequences from both wA and ZY082808. Transformants with pMT3332 will thus contain double stranded RNA for both wA and ZY082808 and expression of both wA and ZY082808 is expected in various degrees to be knocked down in *A. oryzae* strains transformed with pMT3332.

pMT3332 was transformed into *A. oryzae* strain JaL731 and 24 transformants selected by their ability to grow on acetamide as sole source of nitrogen. Transformants were twice reisolated as described above.

The 24 transformants were evaluated in two independent shake flask experiments. As shown in table 4, five to ten of the transformants seemed to have 10-25% increased lipase expression compared to JaL731 although there is some uncertainty due to a high variation from experiment to experiment. This is in line with the clear negative effect of over-expression of ZY082808 in 5-58.

In summary both microarray data for various independent lipase strains, follow up studies by over-expression and by attempted down regulation by shRNA show, that ZY082808 has significant influence on lipase expression.

TABLE 4

| Strain | Experiment 3 Lipase expression in % of JaL731 | Experiment 4 Lipase expression in % of JaL731 |
|---|---|---|
| JaL731pMT3332#1 | 125 | ND |
| JaL731pMT3332#2 | 106 | ND |
| JaL731pMT3332#3 | 123 | 124 |
| JaL731pMT3332#4 | 126 | 128 |
| JaL731pMT3332#5 | 105 | 105 |
| JaL731pMT3332#6 | 113 | 106 |
| JaL731pMT3332#7 | 133 | 124 |
| JaL731pMT3332#8 | 125 | ND |
| JaL731pMT3332#9 | 101 | 105 |
| JaL731pMT3332#10 | ND | ND |
| JaL731pMT3332#11 | 106 | ND |
| JaL731pMT3332#12 | 89 | 114 |
| JaL731pMT3332#13 | 108 | 102 |
| JaL731pMT3332#14 | 113 | ND |
| JaL731pMT3332#15 | 121 | 119 |
| JaL731pMT3332#16 | ND | ND |
| JaL731pMT3332#17 | 131 | 120 |
| JaL731pMT3332#18 | 139 | 157 |
| JaL731pMT3332#19 | 126 | 163 |
| JaL731pMT3332#20 | 50 | ND |
| JaL731pMT3332#21 | 94 | ND |
| JaL731pMT3332#22 | 118 | 166 |
| JaL731pMT3332#23 | 72 | 56 |
| JaL731pMT3332#24 | 123 | 95 |
| JaL731 | 100 | 100 |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Example 4

Construction of a ZY082808 Deleted *A. Oryzae* Strain MT3420 and Expression of a Variant *Humicula Lanuginose* Lipase First a ZY082808 deleted *A. oryzae* strain, MT3420, was constructed. The sequences flanking the ZY082808 ORF were PCR amplified with primers based on the published *A. oryzae* genomic sequence (Machida, M. et al. Nature 438 (2005)1157-1161) using genomic DNA from *A. oryzae* strain BECh2 as template. The 5' flank was amplified using primers 905 and 904 (SEQ ID NO: 31 and 30) to give a PCR fragment of 1162 bp, whereas the 3'flank was amplified by primers 907 and 906 (SEQ ID NO: 33 and 32) to give an 1150 bp fragment. Primers were designed to allow subsequent SOE PCR using primers 905 and 906 to join the fragments placing a Hind3 site between the two flanks. The SOE assembled fragment (2.2 kb) was cloned into the pCR4 TOPO blunt (InVitrogen) to give pMT3369 (SEQ ID NO: 26). The repeat flanked pyrG selection marker was inserted as a Hind3-Hind3 fragment (as described in example 1) into the unique Hind3 site of pMT3369 to give plasmid pMT3376 (SEQ ID NO: 27). Finally the deletion cassette of pMT3376 containing the two flanks of ZY082808 on either side of the pyrG selection marker was transferred as a Not1-Spe1 fragment into the Not1-Xba1 sites of the tk counterselectable plasmid pJaL504 to give the deletion plasmid pMT3378 (SEQ ID NO: 28). Note that pMT3378 contains a unique Not1 site immediately downstream of the 3' flank. This can be used to linearize the plasmid prior to transformation into *A. oryzae*.

The linearized plasmid pMT3378 was transformed into *A. oryzae* JaL355, as described in WO2007045248, by selection for pyrG and counter selection for the tk gene on FDU plates as previously described. 34 transformant colonies were twice reisolated and finally grown up on liquid medium (YPD). Chromosomal DNA was prepared and used in the first place for PCR analysis of the ZY082808 locus. Primers 995 and 996 (SEQ ID NO: 34 and 35) were used for the amplification. The amplified band is expected to have a size of 3.32 kb in the wt strain, while a band of 5.89 kb is expected when the pMT3378 derived deletion cassette has been inserted. Seven of the 34 selected colonies showed the band expected for the deletion strain.

Four potential deletion strains were chosen for Southern verification of the deletion. DNA from a non-deleted control *A. oryzae* strain was run in parallel. The genomic DNA was digested with either BamH1 or with BgI2 and probed with a PCR fragment generated from primers 999 and 1000 (SEQ ID NO: 36 and 37) (*A. oryzae* BECh2 template). In the BamH1 digested samples of the control strain the probe hybridized to the expected size band of 3.9 kb while three out of the four potentially ZY082808 deleted strains showed the predicted bands of 2.0 kb and 1.35 kb. In the BgI2 digest the hybridizing bands were 4.7 kb for the control and 6.4 kb plus 0.9 kb for the same three potentially deleted strains. The fourth deletion candidate strain showed a more complex pattern presumably due to a rearrangement during the integration event. This fourth strain was discarded. Two of the strains showing a clean ZY082808 disruption in the Southern were frozen to the strain collection as MT3420 and 3421.

MT3420 was transformed with pMT3431 (SEQ ID NO: 29) selecting for the amdS marker. pMT3431 is an expression plasmid for the variant *Humicola lanuginose* lipase described under construction of pJaL958, example 1. The main difference between pJaL958 and pMT3431 is the marker for selection which in pMT3431 is the *A. nidulans* amdS gene.

Transformants were obtained and twice reisolated through sporulation. The reisolated transformants were grown and tested for their expression level of the lipase variant.

Transformants of the parent strain *A. oryzae* Bech2 were obtained and tested for parallel comparisons.
Shake Flask Evaluation Two times ten lipase transformants made in respectively MT3420 and BECh2 were tested in shake flask experiments by measurement of lipase activity (LU/ml). The same set up as described in example 2 was applied except that both 1/5MDU2B and 1/5GDU2B shake flask medium were used for expression. 1/5GDU2B is composed as 1/5MDU2B apart from maltose has been substituted with glucose.

In the first experiment the series of transformants in MT3420 had an approx. 20% improved expression in maltose fermentations judged by average and median compared to the series in BECh2 as shown in Table 5. No difference between the hosts was observed in glucose fermentations, meaning that the maltose/glucose expression ratio was increased for transformants in MT3420.

Also in the second shake flask experiment a somewhat increased maltose/glucose expression ratio was observed for the series of transformants in MT3420 compared to the series in BECh2. The experiments have been hampered of variation originating from the none-robust lipase analysis and the nature of the transformants.

In conclusion, there is indication of improved performance for the host MT3420.

TABLE 5

Expression of 10 transformants in MT3420 and 10 transformants in BECh2 ranked after normalization proportionate to the highest expressing transformant in 1/5MDU2B in two independent experiments.

| | 1/5MDU2B | | 1/5 GDU2B | |
|---|---|---|---|---|
| | MT3420 | BECH2 | MT3420 | BECH2 |
| | Experiment 1 | | | |
| 1 | 100 | 68 | 150 | 141 |
| 2 | 92 | 60 | 128 | 141 |
| 3 | 69 | 56 | 122 | 130 |
| 4 | 61 | 53 | 109 | 121 |
| 5 | 59 | 52 | 96 | 91 |
| 6 | 51 | 52 | 95 | 87 |
| 7 | 45 | 44 | 89 | 83 |
| 8 | 45 | 34 | 71 | 65 |
| 9 | 40 | 33 | 41 | 25 |
| 10 | 33 | 26 | 38 | 8 |
| | Experiment 2 | | | |
| 1 | 85 | 100 | 86 | 128 |
| 2 | 77 | 98 | 85 | 109 |
| 3 | 75 | 95 | 82 | 102 |
| 4 | 73 | 82 | 80 | 72 |
| 5 | 71 | 75 | 75 | 65 |
| 6 | 58 | 39 | 62 | 65 |
| 7 | 57 | 38 | 60 | 58 |
| 8 | 52 | 34 | 53 | 35 |
| 9 | 51 | 21 | 44 | 19 |
| 10 | 40 | 7 | 23 | 5 |

The invention claimed is:

1. A mutant fungal host, wherein the mutant has a reduced or no expression of an endogenous polypeptide selected from the group consisting of:
   (a) a polypeptide comprising an amino acid sequence having at least 90% identity to the mature polypeptide of SEQ ID NO: 2;
   b) a polypeptide encoded by a polynucleotide comprising a nucleotide sequence having at least 90% sequence identity to the mature polypeptide coding sequence of SEQ ID NO: 1.

2. The mutant according to claim 1, wherein the endogenous polypeptide comprises the mature polypeptide of SEQ ID NO: 2.

3. The mutant according to claim 2, wherein the endogenous polypeptide consists of the mature polypeptide of SEQ ID NO: 2.

4. The mutant according to claim 3, wherein the endogenous polypeptide is encoded by a polynucleotide which comprises or consists of the nucleotide sequence of SEQ ID NO: 1.

5. The mutant according to claim 4, wherein the endogenous polypeptide is encoded by a polynucleotide which comprises or consists of the mature polypeptide coding sequence of SEQ ID NO: 1.

6. The mutant according to claim 2, wherein the mature endogenous polypeptide is amino acids 20 to 79 of SEQ ID NO: 2.

7. The mutant according to claim 1, wherein the mature endogenous polypeptide coding sequence is nucleotides 58 to 237 of SEQ ID NO: 1.

8. The mutant fungal host according to claim 1, wherein the fungal cell is a filamentous fungal cell.

9. The mutant fungal host according to claim 8, wherein the filamentous fungal host is selected from the group consisting of *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* and *Trichoderma* cell.

10. The mutant fungal host according to claim 9, wherein the *Aspergillus* cell is selected from the group consisting of *Aspergillus awamori, Aspergillus fumigatus, Aspergillus foetidus, Aspergillus japonicus, Aspergillus nidulans, Aspergillus niger* and *Aspergillus oryzae.*

11. The mutant cell claim 1, further comprising a gene encoding a native or heterologous protein.

12. A mutant *Aspergillus* host cell, wherein the mutant has a reduced or no expression of an endogenous polypeptide selected from the group consisting of:
   (a) a polypeptide comprising an amino acid sequence having at least 90% sequence identity to the mature polypeptide of SEQ ID NO: 2;

(b) a polypeptide encoded by a polynucleotide comprising a nucleotide sequence having at least 90% sequence identity to the mature polypeptide coding sequence of SEQ ID NO: 1.

13. The mutant host cell of claim 12, wherein the host cell is *Aspergillus oryzae* and the polypeptide comprises an amino acid sequence having at least 95% sequence identity to the mature polypeptide of SEQ ID NO: 2.

14. The mutant host cell of claim 12, wherein the host cell is *Aspergillus oryzae* and the polypeptide comprises an amino acid sequence having at least 99% sequence identity to the mature polypeptide of SEQ ID NO: 2.

15. The mutant host cell of claim 12, wherein the host cell is *Aspergillus oryzae* and the polypeptide consists of the mature polypeptide of SEQ ID NO: 2.

* * * * *